United States Patent
Purdie et al.

(10) Patent No.: US 11,735,309 B2
(45) Date of Patent: Aug. 22, 2023

(54) METHOD AND SYSTEM FOR AUTOMATED QUALITY ASSURANCE IN RADIATION THERAPY

(71) Applicant: UNIVERSITY HEALTH NETWORK, Toronto (CA)

(72) Inventors: Thomas G. Purdie, Oakville (CA); Christopher James McIntosh, Toronto (CA); Igor Svistoun, North York (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 127 days.

(21) Appl. No.: 15/927,414

(22) Filed: Mar. 21, 2018

(65) Prior Publication Data

US 2018/0211725 A1   Jul. 26, 2018

Related U.S. Application Data

(62) Division of application No. 14/898,060, filed as application No. PCT/CA2014/050551 on Jun. 12, 2014, now Pat. No. 10,475,537.

(Continued)

(51) Int. Cl.
  *G16H 20/40* (2018.01)
  *A61N 5/10* (2006.01)
  (Continued)

(52) U.S. Cl.
  CPC ............. *G16H 20/40* (2018.01); *A61N 5/103* (2013.01); *G16H 10/60* (2018.01); *G16H 20/10* (2018.01);
  (Continued)

(58) Field of Classification Search
  CPC ........ G16H 50/20; G16H 20/30; G16H 10/60; G16H 20/10; G16H 40/20; G16H 50/70;
  (Continued)

(56) References Cited

U.S. PATENT DOCUMENTS

| | | | |
|---|---|---|---|
| 6,546,073 B1* | 4/2003 | Lee | A61N 5/1031 378/65 |
| 2007/0041494 A1 | 2/2007 | Ruchala et al. | |
| 2010/0177871 A1 | 7/2010 | Nord | |
| 2011/0119212 A1* | 5/2011 | De Bruin | A61B 5/00 706/12 |

(Continued)

FOREIGN PATENT DOCUMENTS

| | | |
|---|---|---|
| CA | 2813643 A1 | 4/2012 |
| EP | 2575066 A2 | 4/2013 |
| WO | 2013080165 A1 | 6/2013 |

OTHER PUBLICATIONS

Jackie Wu, Knowledge Based Treatment Planning, Duke University Medical Center Dept. of Radiation Oncology AAPM Presentation (Year: 2012).*

Zhu et al, A planning quality evaluation tool for prostate adaptive IMRT based on machine learning, 38(2) Med. Phys. 719-726 (Feb. 2011) (Year: 2011).*

(Continued)

*Primary Examiner* — Evangeline Barr
*Assistant Examiner* — Jordan L Jackson
(74) *Attorney, Agent, or Firm* — Norton Rose Fulbright Canada LLP

(57) ABSTRACT

Methods and systems for evaluating a proposed treatment plan for radiation therapy, for evaluating one or more delineated regions of interest for radiation therapy, and/or for generating a proposed treatment plan for radiation therapy. Machine learning based on historical data may be used.

36 Claims, 47 Drawing Sheets

Related U.S. Application Data

(60) Provisional application No. 61/834,145, filed on Jun. 12, 2013.

(51) Int. Cl.

| | |
|---|---|
| *G16H 40/20* | (2018.01) |
| *G16H 20/30* | (2018.01) |
| *G16H 20/10* | (2018.01) |
| *G16H 30/40* | (2018.01) |
| *G16H 10/60* | (2018.01) |
| *G16H 50/70* | (2018.01) |
| *G16H 50/20* | (2018.01) |

(52) U.S. Cl.
CPC ............ *G16H 20/30* (2018.01); *G16H 30/40* (2018.01); *G16H 40/20* (2018.01); *G16H 50/20* (2018.01); *G16H 50/70* (2018.01); *A61N 5/1038* (2013.01); *A61N 5/1048* (2013.01); *A61N 2005/1041* (2013.01)

(58) Field of Classification Search
CPC .... A61N 5/103; A61N 5/1038; A61N 5/1048; A61N 2005/1041; G06F 19/3456; G06F 19/3481
See application file for complete search history.

(56) References Cited

U.S. PATENT DOCUMENTS

| | | | |
|---|---|---|---|
| 2012/0312961 A1* | 12/2012 | Raleigh | A61B 6/12 250/206 |
| 2013/0085735 A1* | 4/2013 | Vilsmeier | G06F 19/00 703/11 |

OTHER PUBLICATIONS

Drago, G.P., Setti, E., Licitra, L., Forecasting the performance status of head and neck cancer patient treatment by an interval arithmetic pruned perceptron, 49(8) IEEE Trans Biomed Eng 782-7 (Year: 2002).*

Geert Meyfroidt et al., Machine learning techniques to examine large patient databases, 23 Best Practice & Research Clinical Anaesthesiology 127-143 (Year: 2009).*

T. Shepherd et al., Comparative Study With New Accuracy Metrics for Target Volume Contouring in PET Image Guided Radiation Therapy, 31(11) IEEE Trans Med Imaging 2006-2024 (Nov. 2012) (Year: 2012).*

Tom Fawcett, An Introduction to ROC analysis, 27(8) Pattern Recognition Letters 861-874 (Jun. 2006) (Year: 2006).*

EPO, Extended European Search Report for EP Application No. 14811421.8 dated Nov. 28, 2016.

WIPO, International Search Report and Written Opinion for PCT Application No. PCT/CA2014/050551 dated Aug. 4, 2011.

* cited by examiner

FIG. 3a – Table 1

| Feature | Description | Equation |
|---|---|---|
| Geometrical Centroid | The centre of the ROI | $\mu = \dfrac{1}{|\Psi|} \sum_{i=1}^{|\Psi|} \Psi_i$ |
| Principle Component Analysis - Variance | Variance along the three primary modes of variation | $\text{Diag}(\Sigma)$ where $(\Psi-\mu)(\Psi-\mu)^T = W\Sigma\Sigma^T W^T$ |
| Principle Components | Primary modes of variation | $W$ where $(\Psi-\mu)(\Psi-\mu)^T = W\Sigma\Sigma^T W^T$ |
| Volume | Volume of the ROI | $\sum_{x \in \Omega} S(x)$ |

FIG. 3b – Table 1

| Feature | Description | Equation |
|---|---|---|
| SDF Histogram | Histogram of the shape of the ROI | $hist(S(x)\Phi(x))$ |
| Maximum Thickness | Thickness of the ROI computed from the SDF | $2\max_x(S(x)\Phi(x))$ |
| Mean Intensity | Mean image intensity within the boundaries of the ROI | $\frac{1}{|\Omega|}\sum_{x\in\Omega} S(x)I(x)$ |
| Mode Intensity | Mode image intensity within the boundaries of the ROI | $mode(S(x)I(x))$ |
| Standard Deviation of Intensity | Standard deviation of image intensity within the boundaries of the ROI | $stdev(S(x)I(x))$ |
| Minimum Intensity | Minimum image intensity within the boundaries of the ROI | $\min_x(S(x)I(x))$ |
| Maximum Intensity | Maximum image intensity within the boundaries of the ROI | $\max_x(S(x)I(x))$ |
| Intensity Histogram | Histogram of intensity values within the boundaries of the ROI | $hist(S(x)I(x))$ |

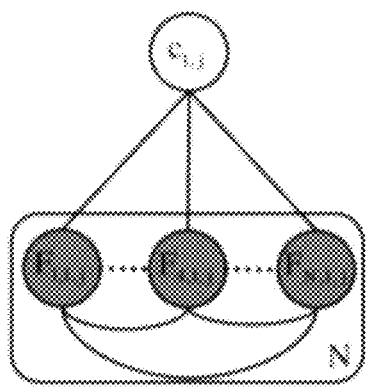 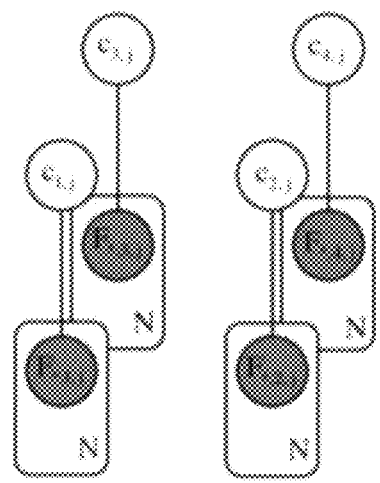
FIG. 4a
FIG. 4b

FIG. 5 - Table 2

| Notation | Meaning |
|---|---|
| P | Set of plans |
| $C_{i,j}$ | ROI i from plan $P_j$ |
| C | Set of ROI class labels (e.g. heart, breast, lung) |
| $c_{i,j}$ | ROI class label for ROI $C_{i,j}$ from plan $P_j$ |
| N | Number of features per ROI |
| $F_{h,i,j}$ | Feature h from ROI $C_{i,j}$ from plan $P_j$ |
| $F_{*,i,j}$ | Features 1...n from ROI $C_{i,j}$ from plan $P_j$ |
| $F_{*,*,j}$ | All features from all ROIs in plan $P_j$ |
| $F_{h,lung,*}$ | Feature h for all lung ROIs in P |

FIG. 6 - Table 3

| Feature | Description | Equation |
|---|---|---|
| Distance | The distance between ROI centres | $\left\| \frac{1}{\|\Psi_1\|} \sum_{i=1}^{\|\Psi_1\|} \Psi_{i,1} - \frac{1}{\|\Psi_2\|} \sum_{i=1}^{\|\Psi_2\|} \Psi_{i,2} \right\|_2$ |
| Volume Difference | Signed volume difference between ROIs | $\sum_{x \in \Omega} S_1(x) - \sum_{x \in \Omega} S_2(x)$ |
| Contains | Fraction of $S_2(x)$ contained in $S_1(x)$ | $\dfrac{\sum_{x \in \Omega} S_1(x) S_2(x)}{\sum_{x \in \Omega} S_1(x)}$ |
| Contained By | Fraction of $S_1(x)$ contained in $S_2(x)$ | $\dfrac{\sum_{x \in \Omega} S_1(x) S_2(x)}{\sum_{x \in \Omega} S_2(x)}$ |

FIG. 7a - Table 4a

| Classifier | Accuracy | Accuracy Std. Dev. | Accuracy OAR | Accuracy Targets | Avg. TPR | Avg. FPR | Min. TPR | Max. FPR |
|---|---|---|---|---|---|---|---|---|
| Artificial Neural Network | 65.31 | 11.34 | 76.18 | 53.55 | 46.95 | 0.46 | 0.00 | 4.11 |
| Naive Bayes | 73.16 | 0.82 | 89.26 | 55.70 | 74.27 | 0.36 | 2.43 | 2.58 |
| Support Vector Machines | 82.64 | 0.67 | 94.08 | 70.24 | 81.22 | 0.23 | 0.79 | 2.10 |
| Random Forest (RF) | 85.84 | 0.56 | 95.42 | 75.45 | 83.95 | 0.19 | 0.00 | 2.66 |
| Groupwise RF | 89.58 | 0.55 | 96.70 | 81.87 | 88.18 | 0.14 | 0.00 | 2.65 |
| Groupwise RF exact | 90.00 | 0.47 | 96.97 | 82.46 | 89.03 | 0.13 | 3.10 | 2.62 |
| Conditional RF | 91.08 | 0.48 | 97.32 | 84.31 | 90.18 | 0.12 | 7.19 | 2.56 |
| Groupwise Conditional RF | 91.43 | 0.50 | 97.31 | 85.06 | 90.91 | 0.12 | 28.15 | 2.64 |
| Groupwise Conditional RF exact | 91.58 | 0.48 | 97.38 | 85.29 | 90.99 | 0.11 | 28.55 | 2.60 |

FIG. 7b - Table 4b

| Classifier | Accuracy | Accuracy OAR | Accuracy Targets | Avg. TPR | Avg. FPR |
|---|---|---|---|---|---|
| Support Vector Machines | 77.49 | 85.38 | 51.81 | 38.97 | 0.07 |
| Random Forest (RF) | 82.99 | 90.06 | 59.97 | 44.76 | 0.06 |
| Groupwise RF | 88.69 | 94.23 | 70.63 | 53.59 | 0.04 |
| Conditional RF | 89.97 | 95.15 | 73.13 | 58.32 | 0.03 |
| Groupwise Conditional RF | 89.85 | 94.83 | 73.62 | 57.42 | 0.03 |

FIG. 13a - Table 5

| Plan Class | Number of Examples | True Positive Rate | False Positive Rate |
|---|---|---|---|
| Head+NeckLarynxIMRT [7000_35] | 16 | 1.000 | 0.001 |
| Head+NeckNasopharynxIMRT [7000_35] | 20 | 1.000 | 0.000 |
| Head+NeckOropharynxIMRT [7000_35] | 63 | 0.583 | 0.005 |
| Head+NeckTongueIMRT [7000_35] | 22 | 0.250 | 0.001 |
| Head+NeckTonsilIMRT [7000_35] | 38 | 0.286 | 0.002 |
| BreastLeftBreast+Supraclav+Axilla4F [5000_25+5000_25] | 93 | 0.588 | 0.005 |
| BreastLeftBreast+Supraclav4F [5000_25+5000_25] | 39 | 0.375 | 0.002 |
| BreastLeftBreastTangent [4240_16] | 835 | 1.000 | 0.000 |
| BreastLeftBreastTangent [5000_25] | 67 | 1.000 | 0.000 |
| BreastLeftCavityElectron_MV [400_2+600_3] | 119 | 1.000 | 0.000 |
| BreastLeftCavityIMRT [1000_5] | 412 | 0.987 | 0.001 |
| BreastLeftChestwall+Supraclav+Axilla4F [5000_25+5000_25] | 109 | 0.800 | 0.007 |
| BreastLeftChestwall+Supraclav4F [5000_25+5000_25] | 34 | 0.286 | 0.000 |
| BreastLeftChestwallTangent [5000_25] | 10 | 1.000 | 0.000 |
| BreastRightBreast+Supraclav+Axilla4F [5000_25+5000_25] | 104 | 0.789 | 0.004 |
| BreastRightBreast+Supraclav4F [5000_25+5000_25] | 32 | 0.000 | 0.000 |
| BreastRightBreastTangent [4240_16] | 826 | 1.000 | 0.000 |
| BreastRightBreastTangent [5000_25] | 76 | 1.000 | 0.002 |
| BreastRightCavityElectron_MV [400_2+600_3] | 119 | 1.000 | 0.000 |
| BreastRightCavityIMRT [1000_5] | 382 | 0.971 | 0.001 |
| Head+NeckNasopharynxIMRT [7000_35] | 20 | 1.000 | 0.000 |
| Head+NeckOropharynxIMRT [7000_35] | 63 | 0.583 | 0.005 |
| Head+NeckTongueIMRT [7000_35] | 22 | 0.250 | 0.001 |
| Head+NeckTonsilIMRT [7000_35] | 38 | 0.286 | 0.002 |
| BreastLeftBreast+Supraclav+Axilla4F [5000_25+5000_25] | 93 | 0.588 | 0.005 |
| BreastLeftBreast+Supraclav4F [5000_25+5000_25] | 39 | 0.375 | 0.002 |
| BreastLeftBreastTangent [4240_16] | 835 | 1.000 | 0.000 |
| BreastLeftBreastTangent [5000_25] | 67 | 1.000 | 0.000 |
| BreastLeftCavityElectron_MV [400_2+600_3] | 119 | 1.000 | 0.000 |
| BreastRightCavityIMRT [1000_5] | 382 | 0.971 | 0.001 |
| BreastRightChestwall+Supraclav+Axilla4F [5000_25+5000_25] | 106 | 0.900 | 0.008 |
| BreastRightChestwall+Supraclav4F [5000_25+5000_25] | 31 | 0.000 | 0.001 |

FIG. 13b – Table 5

| Plan Class | Number of Examples | True Positive Rate | False Positive Rate |
|---|---|---|---|
| BreastRightChestwallTangent [5000_25] | 11 | 0.500 | 0.000 |
| GI(Upper)PancreasIMRT [4500_25] | 12 | 0.667 | 0.000 |
| GI(upper)EsophagusIMRT [5000_25] | 26 | 1.000 | 0.002 |
| GI(upper)LiverIMRT [3000_6] | 21 | 0.750 | 0.000 |
| GI(upper)LiverIMRT [3300_6] | 26 | 1.000 | 0.001 |
| GI(upper)LiverIMRT [3900_6] | 12 | 0.667 | 0.000 |
| GI(upper)LiverVMAT [3000_6] | 14 | 1.000 | 0.000 |
| GI(upper)StomachIMRT [4500_25] | 33 | 1.000 | 0.001 |
| LungMesotheliomaIMRT [3000_5] | 33 | 1.000 | 0.000 |
| LungMesotheliomaIMRT [6000_25] | 12 | 1.000 | 0.000 |
| LungNon-SmallCellIMRT [3600_12] | 15 | 1.000 | 0.001 |
| LungNon-SmallCellIMRT [4500_25] | 27 | 0.800 | 0.000 |
| LungNon-SmallCellIMRT [6000_20] | 13 | 0.667 | 0.000 |
| LungNon-SmallCellIMRT [6000_30] | 55 | 0.900 | 0.001 |
| LungNon-SmallCellIMRT [6600_33] | 132 | 1.000 | 0.001 |
| LungNon-SmallCellVMAT [4800_4] | 96 | 0.944 | 0.000 |
| LungNon-SmallCellVMAT [5400_3] | 11 | 1.000 | 0.000 |
| LungNon-SmallCellVMAT [6000_8] | 27 | 1.000 | 0.001 |
| LungSmallCellIMRT [4500_30] | 13 | 0.667 | 0.000 |
| LungThymomaIMRT [4000_20] | 14 | 1.000 | 0.000 |
| GI(Lower)AnalCanalIMRT [1800_10] | 18 | 0.750 | 0.000 |
| GI(Lower)AnalCanalIMRT [2700_15] | 20 | 0.750 | 0.000 |
| GI(Lower)AnalCanalIMRT [3600_20+1800_10] | 32 | 1.000 | 0.000 |
| GI(Lower)AnalCanalIMRT [3600_20+2700_15] | 41 | 1.000 | 0.000 |
| GI(Lower)AnalCanalIMRT [3600_20] | 45 | 1.000 | 0.000 |
| GI(Lower)Rectum3F [4500_25] | 74 | 1.000 | 0.001 |
| GI(Lower)Rectum3F [5000_25] | 92 | 1.000 | 0.001 |
| GI(Lower)RectumIMRT [5000_25] | 82 | 1.000 | 0.000 |
| GUProstate+NodesIMRT [2800_24] | 56 | 1.000 | 0.001 |
| GUProstate+NodesIMRT [4600_23+2800_14] | 66 | 1.000 | 0.000 |
| GUProstate+NodesIMRT [4600_23] | 48 | 1.000 | 0.000 |
| GUProstate+NodesVMAT [5400_27+2400_12] | 52 | 1.000 | 0.000 |
| GUProstateBed+NodesIMRT [4600_23+2000_10] | 17 | 1.000 | 0.000 |
| GUProstateBedIMRT [6600_33] | 266 | 1.000 | 0.000 |
| GUProstateBedVMAT [6600_33] | 186 | 1.000 | 0.000 |
| GUProstateIMRT [6000_20] | 45 | 1.000 | 0.000 |
| GUProstateIMRT [7800_39] | 336 | 1.000 | 0.000 |
| GUProstateVMAT [6000_20] | 15 | 1.000 | 0.000 |
| GUProstateVMAT [7800_39] | 334 | 1.000 | 0.000 |
| GUSeminomaIMRT [2500_20+1000_25] | 11 | 1.000 | 0.000 |
| GyneGyne4F [4500_25] | 110 | 0.950 | 0.000 |

FIG. 13c – Table 5

| Plan Class | Number of Examples | True Positive Rate | False Positive Rate |
|---|---|---|---|
| GyneGyneIMRT [4500_25] | 48 | 1.000 | 0.000 |
| CNSBrainIMRT [4005_15] | 69 | 1.000 | 0.000 |
| CNSBrainIMRT [5000_25] | 64 | 0.833 | 0.001 |
| CNSBrainIMRT [5400_30] | 107 | 1.000 | 0.001 |
| CNSBrainIMRT [6000_30] | 206 | 0.974 | 0.000 |
| CNSParaspinalIMRT [2400_2] | 16 | 1.000 | 0.001 |
| CNSParaspinalIMRT [2400_3] | 20 | 0.750 | 0.000 |
| LymphomaBrainPOP [1200_8] | 43 | 1.000 | 0.001 |
| LymphomaMantlePOP [3000_20] | 20 | 1.000 | 0.000 |
| LymphomaMantlePOP [3500_20] | 11 | 0.500 | 0.000 |
| SarcomaAbdomen_PelvisIMRT [5000_25] | 44 | 0.875 | 0.001 |
| SarcomaChestIMRT [5000_25] | 14 | 0.667 | 0.001 |
| SarcomaLowerExtremityIMRT [5000_25] | 13 | 0.000 | 0.002 |
| SarcomaUpperExtremityIMRT [5000_25] | 30 | 0.167 | 0.001 |
| AbdomenAbdomenPOP [2000_5] | 32 | 0.333 | 0.001 |
| AbdomenLiverPOP [800_1] | 38 | 1.000 | 0.000 |
| BrainBrainPOP [2000_5] | 263 | 1.000 | 0.000 |
| BrainBrainPOP [3000_10] | 55 | 0.900 | 0.000 |
| Head+NeckEyePOP [2000_10] | 25 | 1.000 | 0.001 |
| PelvisHemipelvisPOP [2000_5] | 13 | 0.000 | 0.001 |
| PelvisHipPOP [2000_5] | 13 | 0.000 | 0.002 |
| PelvisHipPOP [800_1] | 11 | 0.500 | 0.001 |
| PelvisHip_FemurPOP [2000_5] | 11 | 0.500 | 0.000 |
| PelvisIlliumPOP [2000_5] | 15 | 0.333 | 0.001 |
| PelvisIlliumPOP [800_1] | 14 | 1.000 | 0.001 |
| PelvisMiddlepelvisPOP [2000_5] | 31 | 0.667 | 0.003 |
| PelvisMiddlepelvisPOP [3000_10] | 11 | 1.000 | 0.000 |
| SpineCSpinePOP [2000_5] | 24 | 1.000 | 0.000 |
| SpineCTSpinePOP [2000_5] | 25 | 1.000 | 0.000 |
| SpineLSSpinePOP [2000_5] | 56 | 0.818 | 0.005 |
| SpineLSSpinePOP [800_1] | 18 | 0.750 | 0.000 |
| SpineLSSpine_PelvisPOP [2000_5] | 18 | 0.250 | 0.001 |
| SpineLSpinePOP [2000_5] | 65 | 0.750 | 0.003 |
| SpineLSpinePOP [800_1] | 20 | 0.750 | 0.000 |
| ThoraxChestwallPOP [2000_5] | 23 | 0.000 | 0.001 |
| ThoraxLungPOP [2000_5] | 161 | 0.897 | 0.012 |
| ThoraxLungPOP [3000_10] | 67 | 0.846 | 0.003 |
| ThoraxLung_MediastinumPOP [2000_5] | 83 | 0.133 | 0.000 |
| ThoraxLung_MediastinumPOP [3000_10] | 20 | 0.000 | 0.001 |
| ThoraxRibPOP [2000_5] | 14 | 0.333 | 0.001 |

FIG. 14a - Table 6

| ROI Class | Plan Class of ROI | Num. Training | Num. Testing | TPR | FPR |
|---|---|---|---|---|---|
| Heart | Whole Breast | 352 | 232 | 99.79 | 0.08 |
| Left Lung | Whole Breast | 437 | 290 | 99.21 | 0.04 |
| Anal | Anal Canal | 152 | 101 | 92.29 | 0.09 |
| Right Lung | Whole Breast | 439 | 292 | 99.40 | 0.04 |
| Breast Wire | Whole Breast | 146 | 91 | 99.90 | 0.00 |
| Bladder | Anal Canal | 172 | 113 | 97.05 | 0.03 |
| Bladderwall | Prostate | 229 | 156 | 99.46 | 0.00 |
| Kidneys | Esophagus | 24 | 15 | 93.72 | 0.00 |
| Lungs | Whole Breast | 56 | 39 | 81.55 | 0.03 |
| Spinal Canal | Esophagus | 232 | 158 | 99.43 | 0.01 |
| Spinal Canal | Whole Breast | 219 | 150 | 99.72 | 0.01 |
| Spinal Cord | Whole Breast | 204 | 137 | 99.70 | 0.00 |
| Carina | Lung | 54 | 38 | 96.33 | 0.00 |

FIG. 14b - Table 6

| ROI Class | Plan Class of ROI | Num. Training | Num. Testing | TPR | FPR |
|---|---|---|---|---|---|
| Esophagus | Esophagus | 158 | 106 | 94.51 | 0.02 |
| External | Anal Canal | 74 | 49 | 100.00 | 0.00 |
| External | Esophagus | 23 | 15 | 86.01 | 0.01 |
| External | Lung | 53 | 33 | 97.33 | 0.03 |
| Genital | Anal Canal | 84 | 55 | 99.25 | 0.00 |
| Large Bowel | Anal Canal | 84 | 55 | 97.09 | 0.01 |
| Left Common | Anal Canal | 43 | 27 | 99.18 | 0.01 |
| Left External | Anal Canal | 44 | 29 | 100.0 | 0.01 |
| Left Femoral | Anal Canal | 45 | 28 | 98.68 | 0.01 |
| Left Femur | Anal Canal | 309 | 208 | 99.02 | 0.02 |

FIG. 14c - Table 6

| ROI Class | Plan Class of ROI | Num. Training | Num. Testing | TPR | FPR |
|---|---|---|---|---|---|
| Left Internal | Anal Canal | 43 | 27 | 100.0 | 0.00 |
| Liver | Esophagus | 28 | 19 | 92.59 | 0.00 |
| Left Kidney | Esophagus | 26 | 17 | 94.75 | 0.01 |
| Meso | Anal Canal | 143 | 92 | 94.64 | 0.06 |
| Lungs | Esophagus | 176 | 121 | 95.55 | 0.10 |
| Right Common | Anal Canal | 43 | 27 | 99.18 | 0.00 |
| Rectosigmoid | Rectum | 64 | 45 | 69.87 | 0.08 |
| Rectum | Anal Canal | 164 | 110 | 84.98 | 0.16 |
| Rectumwall | Prostate | 229 | 155 | 99.46 | 0.00 |
| Right External | Anal Canal | 44 | 29 | 100.0 | 0.00 |
| Right Femoral | Anal Canal | 45 | 28 | 98.68 | 0.01 |
| Right Femur | Anal Canal | 311 | 210 | 99.02 | 0.02 |
| Right Internal | Anal Canal | 44 | 29 | 98.91 | 0.00 |
| Right Kidney | Esophagus | 27 | 18 | 93.68 | 0.00 |
| Small Bowel | Anal Canal | 152 | 100 | 94.95 | 0.05 |
| Scar | Whole Breast | 91 | 58 | 100.0 | 0.01 |

FIG. 15a - Table 7

| ROI Class | Plan Class of ROI | Num. Training | Num. Testing | TPR | FPR |
|---|---|---|---|---|---|
| RCTV | Anal Canal | 86 | 55 | 97.36 | 0.03 |
| LCTV | Anal Canal | 85 | 54 | 97.68 | 0.02 |
| CTV | Anal Canal | 202 | 130 | 96.30 | 0.23 |
| modLPTV | Anal Canal | 73 | 47 | 94.01 | 0.07 |
| modRPTV | Anal Canal | 74 | 47 | 87.74 | 0.10 |
| modPTV | Anal Canal | 147 | 95 | 74.06 | 0.20 |
| GTV | Anal Canal | 75 | 48 | 95.10 | 0.06 |
| LPTV | Anal Canal | 78 | 51 | 92.08 | 0.04 |
| RPTV | Anal Canal | 78 | 51 | 87.10 | 0.07 |
| PTV | Anal Canal | 158 | 102 | 80.53 | 0.28 |
| Lx | Anal Canal | 51 | 32 | 98.22 | 0.01 |
| Rx | Anal Canal | 40 | 26 | 98.88 | 0.02 |
| LxCTV | Anal Canal | 33 | 20 | 94.74 | 0.03 |
| LxPTV | Anal Canal | 20 | 13 | 76.11 | 0.03 |

FIG. 15b - Table 7

| ROI Class | Plan Class of ROI | Num. Training | Num. Testing | TPR | FPR |
|---|---|---|---|---|---|
| modLxPTV | Anal Canal | 15 | 9 | 67.14 | 0.02 |
| LxGTV | Anal Canal | 9 | 9 | 100.00 | 0.00 |
| RxGTV | Anal Canal | 9 | 9 | 100.00 | 0.00 |
| RxCTV | Anal Canal | 11 | 7 | 93.23 | 0.01 |
| modRxPTV | Anal Canal | 6 | 4 | 82.22 | 0.00 |
| Cavity | Whole Breast | 223 | 144 | 91.07 | 0.17 |
| modCavity | Whole Breast | 221 | 143 | 91.25 | 0.17 |
| CTVcavity | Whole Breast | 220 | 142 | 98.19 | 0.03 |
| PTVcavity | Whole Breast | 220 | 143 | 98.24 | 0.03 |
| DEVcavity | Whole Breast | 220 | 142 | 95.58 | 0.07 |
| CTV | Whole Breast | 204 | 129 | 98.30 | 0.05 |
| CTV | Esophagus | 55 | 39 | 62.30 | 0.14 |
| GTV | Esophagus | 43 | 30 | 66.71 | 0.07 |
| PTV | Esophagus | 44 | 31 | 62.95 | 0.11 |
| CTV | Lung | 738 | 496 | 71.94 | 2.60 |
| PTV | Lung | 462 | 314 | 69.90 | 1.13 |
| GTV | Lung | 535 | 367 | 80.97 | 1.44 |

FIG. 15c - Table 7

| ROI Class | Plan Class of ROI | Num. Training | Num. Testing | TPR | FPR |
|---|---|---|---|---|---|
| CTV | Prostate | 231 | 156 | 99.43 | 0.00 |
| PTV | Prostate | 229 | 156 | 99.46 | 0.00 |
| CTV | Rectum | 7 | 5 | 28.55 | 0.00 |
| GTV | Rectum | 85 | 56 | 75.50 | 0.36 |
| Lx | Rectum | 61 | 36 | 86.31 | 0.10 |
| Rx | Rectum | 44 | 24 | 73.56 | 0.08 |

FIG. 17a - Table 8

| Feature | Description | Details |
|---|---|---|
| Beam Control Point Gantry Angle | Direction given beam in directed | Specified as an angle |
| Beam Control Point Source To Surface Distance | The distance between the treatment source and the patient surface | Specified as a distance in cm |
| Beam Control Point Couch Angle | Rotation of the couch for given beam | Specified as an angle |
| Beam Control Point Collimator Angle | Rotation of the collimation system of the used to shape the treatment beam | Specified as an angle |
| Beam Control Point Area | The area of the beam at a given control point, in plane perpendicular to the beam (beam's eye view) at the isocenter. | Specified as cm2 |
| Beam Control Point DRR | Digitally reconstructed radiograph from the beam's eye view. | |

FIG. 17b - Table 8

| Feature | Description | Details |
|---|---|---|
| Beam MCS | The overall score on a scale of [0..1] that describes complexity of the beam taking into account all the control points.<br><br>For static and IMRT beams: MCS = LSV*AAV<br><br>For VMAT beams: MCS = LSV*LTV*DRV | Specified as a score from 0 (highly complex) to 1 (open square field) |
| Beam LSV | Score from 0..1 describing the shape of a given beam aperture | Specified as a score from 0 (highly complex) to 1 (no variability) |
| Beam AAV (non-VMAT) | Score from 0..1 describing the relative area of the given aperture to the maximum area from all the apertures from a given beam direction. (non-VMAT) | Specified as a score from 0 (highly complex) to 1 (no variability) |

FIG. 17c - Table 8

| Feature | Description | Details |
|---|---|---|
| Beam LTV (VMAT only) | Score from 0..1 describing the variability in leaf position from one arc position to the next arc position | Specified as a score from 0 (highly complex) to 1 (no variability) |
| Beam Maximum Area | The maximum area of all the control points. See Beam Control Point Area feature. | Specified in cm2 |
| Beam DRV (VMAT only) | Score for 0..1 describing the fluctuation in the dose rate over a VMAT Arc. | Specified as a score from 0 (highly complex) to 1 (no variability) |
| Beam Number of Segments | Number of segments of the beam where the radiation is delivered, as opposed to control points that only shift the beam's geometry without radiation. | Specified as an integer |
| Beam Energy | Megavolt energy of the beam used. | Specified as an integer with units of MV |

FIG. 17d - Table 8

| Feature | Description | Details |
|---|---|---|
| Beam Energy Type | Photon, electron, proton | Specified as text |
| Beam Delivery Type | Static, IMRT, VMAT | Specified as text |
| Beam MU | Monitor Units delivered by the given beam. | Specified as a float |
| Fraction Group Unique Beams From Angle | Given all the beams in a fraction group, count how many are from a unique angle. | Specified as an integer |
| Fraction Group # Beams With Non Zero MU | Given all the beams in a fraction group, count how many deliver radiation i.e. exclude any beams that do not deliver radiation | Specified as an integer |
| Fraction Group MU | MU delivered by all the beams in this fraction group. | Specified as a float |
| Fraction Group LSV | LSV value taking into account all beams belonging to this fraction group. | Specified as a score from 0 (highly complex) to 1 (no variability) |

FIG. 17e - Table 8

| Feature | Description | Details |
|---|---|---|
| Fraction Group AAV | AAV value taking into account all beams belonging to this fraction group | Specified as a score from 0 (highly complex) to 1 (no variability) |
| Fraction Group LTV | LTV value taking into account all beams belonging to this fraction group | Specified as a score from 0 (highly complex) to 1 (no variability) |
| Fraction Group DRV | DRV value taking into account all beams belonging to this fraction group | Specified as a score from 0 (highly complex) to 1 (no variability) |
| Fraction Group MCS | MCS score taking into account all beams belonging to this fraction group | Specified as a score from 0 (highly complex) to 1 (open square field) |
| Fraction Group # of Fractions Planned | Number of fractions scheduled for the patient by this fraction group. | Specified as an integer |

FIG. 17f - Table 8

| Feature | Description | Details |
|---|---|---|
| Plan MU | Total MU delivered by the plan (all fraction groups) | Specified as a float |
| Plan Number of Fraction Groups | Number of fraction groups this plan contains. | Specified as an integer |

FIG. 21 – Table 9

| Feature | Description | Details |
|---|---|---|
| Image texture | Multi-scale, multi-rotation Gabor features extended to 3D computed across the image | Image convolution results from the Gabor filter bank [38] extended to 3D |
| Image intensity | Image values at corresponding voxel, or averaged over corresponding voxel patch | Numerical value obtained directly from the image data, or averaged over a patch of image data |
| Image position | Location of the pixel within an image | x,y,z location of a pixel within the image |
| Position inside patient | Location of a pixel (or patch) within the patient | External segmentation is automatically obtained via image thresholding or other suitable method or manually. Signed distance transform [39] is computed and used to encode distance from any voxel (patch) to the nearest patient external boundary. |
| Position inside ROI | Location of a pixel within a particular ROI | Same as position inside patient but for varied anatomy, segmentation may be provided by an automatic approach or manually. |

FIG. 22a    FIG. 22b    FIG. 22c
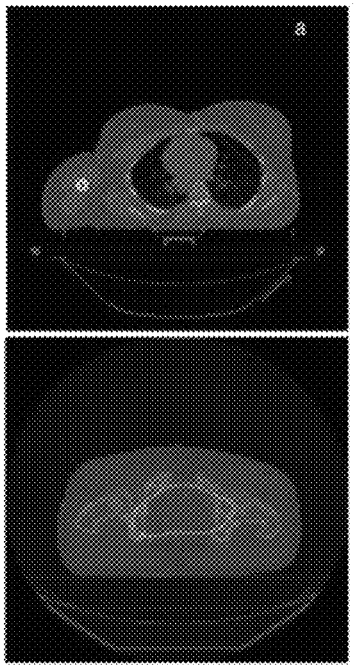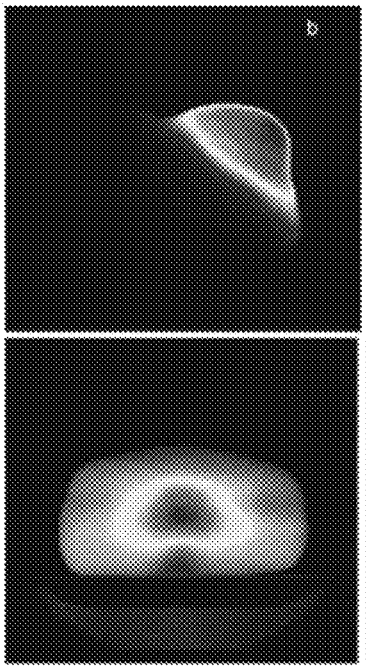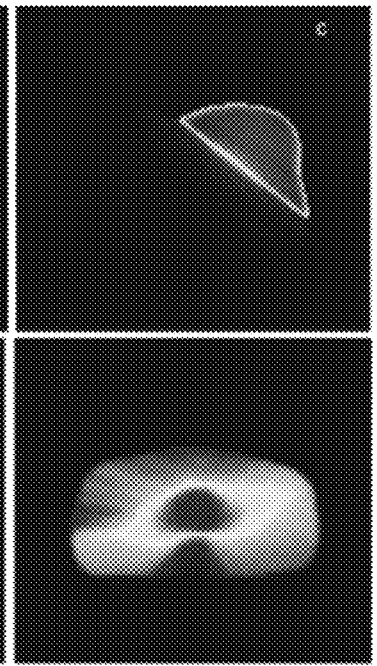

FIG. 23 – Table 10

|  | Number of RT Plans | | Correlation | | % Overlap of 60% Dose | |
| --- | --- | --- | --- | --- | --- | --- |
|  | Testing | Training | Mean | St Dev | Mean | St Dev |
| Breast | 20 | 95 | 0.940 | 0.044 | 0.847 | 0.122 |
| Prostate | 20 | 78 | 0.842 | 0.116 | 0.590 | 0.220 |

METHOD AND SYSTEM FOR AUTOMATED QUALITY ASSURANCE IN RADIATION THERAPY

TECHNICAL FIELD

The present disclosure relates to methods and systems for evaluating and generating radiation therapy (RT) treatment plans. In particular, the present disclosure relates to methods and systems for providing a calculated quality estimate for a proposed RT treatment plan and/or for a delineated region of interest and generating a proposed dose distribution for an RT treatment plan.

BACKGROUND

An estimated 187,600 new cases of cancer are expected in Canada in 2013 [1] with radiation therapy (RT) indicated as part of the patient's management in approximately 40 percent of cancer cases [2]. The delivery of RT for the treatment of cancer typically is a complicated process that requires both clinical and technical expertise in order to generate treatment plans that are safe and effective for the treatment of cancer.

For the RT process, patients are imaged with computed tomography (CT) imaging and optionally with multi-modality imaging (e.g. MR, PET) depending on the treatment site. Regions of interest (ROIs) i.e. targets (the locations radiation is directed to) and normal tissue structures (the locations radiation is minimized to) are delineated manually and/or semi-automatically on the acquired images (a). Treatment plans are generated manually, in which the direction of radiation beams and the clinical objectives of the treatment must be specified. An optimization algorithm is then used to generate the intensity and/or shape and/or modulation of radiation beams to achieve the treatment objectives (b). A dose distribution, a spatial representation of the radiation dose the patient will receive, can then be calculated. Therefore, the dose distribution (also referred to as a dose map) is directly connected with the anatomical imaging acquired from the RT process to relate the dose and spatial information specific to the patient.

In addition, the dose distribution is used to quantitatively evaluate the dose received by the delineated ROIs for assessing treatment plan quality and safety (c). The steps (a-c) are repeated until an acceptable plan is generated. Finally, the completed treatment plans are then reviewed by the multi-disciplinary RT team for quality, safety and compliance with established clinical protocols before the treatment plan will be delivered to the patient.

RT Quality Assurance

The RT treatment plan quality assurance (QA) process typically relies on the vigilance of the multi-disciplinary team to review and assimilate relatively complex data from different sources. Human vigilance has been found to be effective in the treatment plan QA process in about 80 percent of cases [3] and for preventing treatment incidents in about 98 percent of cases [4,5]. As a result, sub-optimal treatment plans, which have the potential to result in a significant detriment to the patient, may be used clinically. Several studies have shown treatment plans, which deviate from established QA guidelines, result in worse patient outcomes [6,7]. Therefore, the current RT process may require substantial multi-disciplinary QA resources to reduce the likelihood of errors and to ensure a high standard of patient care.

The multi-disciplinary RT team comprising radiation therapists, physicists and oncologists typically reviews each proposed treatment plan for clinical and technical merit. This review typically includes assessing safety (e.g., that the proposed plan does not exceed any normal tissue dose tolerances), deliverability (e.g., the dose calculated in the proposed treatment plan can be reproduced on the treatment unit), consistency in the transfer of data between databases (e.g., the parameters defining the proposed plan are the same parameters to actually treat the specific patient) and overall quality (e.g., the proposed plan is consistent with other plans for the given site and technique in terms of the dose prescription, the dose distribution, target coverage etc.) [8-19].

This process is typically largely manual and complex, as there may be numerous parameters that require human expert review. This has led to an interest in automated QA methods in order to reduce the reliance on human vigilance [20-23]. Methods developed to date have shown promise only in a limited clinical scope.

RT Planning

Technical innovations in RT have improved the quality of treatment plans usually at the cost of increased complexity. However, treatment planning still remains a highly manual process, which requires users to delineate numerous regions of interest (ROIs) for treatment planning and set treatment objectives for an optimization engine to solve. For example, optimization objectives may specify the target ROI must receive>95% of the prescription dose to >95% of the target volume while a healthy organ must receive<100% of the prescription dose to 1 cc of the organ volume.

The process almost always involves multiple iterations, as changes to the objectives and the ROIs themselves are required to generate an acceptable treatment plan. To date, conventional automated treatment planning methods have focused on setting objectives and then optimizing those objectives to generate the dose distribution (also referred to as a dose map). Such a process still requires ROI delineation, beam placement, and manual adjustment of the objectives.

In addition, the variation in ROI delineation and treatment plan quality is well-established [24,25]. The use of automation may help to improve consistency and add standardization to the process [26].

SUMMARY

In various examples and embodiments, the present disclosure incorporates automation into the multi-disciplinary RT treatment plan QA and treatment planning process. This may help to improve plan quality and/or patient safety above the 80 percent level attained by human vigilance alone.

In some examples, automation in the context of QA and treatment planning may employ computer-assisted methods such as machine learning (e.g., classification and regression) and/or registration (e.g., image processing). The present disclosure provides examples employing the machine learning techniques of automated classification and regression; however other computer-assisted techniques could be used to achieve an automated QA and/or treatment planning process.

An automated QA and/or treatment planning framework, such as that provided in some examples of the present disclosure, may help to reduce delays in patients receiving treatment due to errors necessitating plan re-work and re-optimization. Automated classification and/or regression algorithms may better utilize the vast clinical RT data available and/or may provide a mechanism for standardizing and/or continuously improving the quality of plans by correlating individual treatment planning with plans of known high quality and safety. The methodology may promote widespread dissemination to other institutions, which may benefit other patients receiving RT as part of their cancer management.

Compared to conventional simple automated QA and treatment planning methods, the present disclosure may employ more sophisticated algorithms and more data that may have the potential to have clinical impact across a much wider array of treatments.

In some examples, the present disclosure describes using a database of patients with corresponding high-quality treatment plans, which may help to enable one or more of: automatically inferring the quality of a novel proposed plan for a novel patient; automatically inferring the quality of delineated regions of interest (ROIs); automatically inferring the class label for each ROI; and automatically inferring a class label for the proposed treatment plan, estimating a dose distribution specific to a novel patient, inferring the treatment planning parameters to achieve the estimated dose distribution.

A basic mechanism of this approach may be to figure out which patients in a database of historical treatment plans and patients are most similar to the novel patient, and then 1) estimating a dose distribution and associated treatment plan or 2) compare the novel proposed plan with the corresponding historical patient plans from the database. Though it may be possible to manually encode distance metrics between patients, and/or distance metrics between plans, in order to evaluate similarity, in some examples machine learning methods may be used to automatically learn the relationship between different patients and/or different plans, and ultimately patients and plans.

In some example aspects, the present disclosure provides a method for evaluating a proposed treatment plan for RT, where the method may include: obtaining the proposed treatment plan defining treatment for at least one treatment site, and a set of patient data for a patient; automatically characterizing the proposed treatment plan according to one or more predefined features to determine a treatment plan characterization; calculating a quality estimate for the proposed treatment plan by evaluating the proposed treatment plan according to one or more rules (which may be predefined or learned by the system, for example, as discussed further below) defining expected relationships between the treatment plan characterization and one or more of: one or more plan features, and one or more patient features defined in the set of patient data; and providing output indicating the calculated quality estimate.

In some examples, the method may also include: obtaining a set of region of interest (ROI) data delineating at least one ROI in the set of image data; and automatically characterizing the at least one ROI according to one or more predefined features to determine at least one ROI characterization; wherein calculating the quality estimate for the proposed treatment plan includes evaluating the proposed treatment plan according to one or more rules defining expected relationships between the treatment plan characterization and the at least one ROI characterization.

In some example aspects, the present disclosure provides a method for evaluating at least one delineated region of interest (ROI) for RT, where the method may include: obtaining a set of ROI data delineating the at least one ROI for at least one treatment site in a set of image data, and a set of patient data for a patient; automatically characterizing the at least one ROI according to one or more predefined features to determine at least one ROI characterization; calculating a quality estimate for the at least one ROI by evaluating the at least one ROI according to one or more rules (which may be predefined or learned by the system, for example, as discussed further below) defining expected relationships between the at least one ROI characterization and one or more of: one or more ROI features, and one or more patient features defined in the set of patient data; and providing output indicating the calculated quality estimate.

In some examples, the method may include: obtaining a proposed treatment plan defining treatment for the at least one treatment site; and automatically characterizing the proposed treatment plan according to one or more predefined features to determine a treatment plan characterization; wherein calculating the quality estimate for the at least one ROI includes evaluating the at least one ROI according to one or more rules defining expected relationships between the at least one ROI characterization and the treatment plan characterization.

In some example aspects, the present disclosure provides a method for generating a proposed treatment plan for radiation therapy, where the method may include: obtaining a set of patient data for a patient including at least one set of image data for at least one treatment site; determining a treatment plan class, from a plurality of predefined treatment plan classes, each predefined treatment plan classes defining one or more treatment plan features relevant to treatment of a respective treatment site; calculating a proposed dose map (e.g., by performing dose inference) by determining a dosage over a volume depicted in the set of image data according to a first set of rules (which may include predefined rules or machine-learned rules, as discussed further below) including one or more rules defining expected relationships between applied dosage, the treatment plan class, and at least one feature of the image data; determining one or more treatment plan parameters for achieving the proposed dose map according to a second set of rules (which may include predefined rules or machine-learned rules, as discussed further below) defining expected relationships between dosage and treatment plans; and generating as output the proposed treatment plan including the one or more determined treatment plan parameters.

In some examples, the method may include displaying a visualization of the proposed dose map on a display device, the visualization comprising a voxel-by-voxel mapping of proposed dosages superimposed on the set of image data. Optionally, a user interface may be provided with the visualization to receive user input to modify at least one of: proposed dosage for at least one voxel of the proposed dose map, and one or more features of the image data. The proposed dose map may then be recalculated in accordance with any inputted modification.

In some example aspects, the present disclosure provides a system for evaluating a proposed treatment plan for RT, for evaluating at least one ROI for RT and/or for generating a proposed treatment plan for RT, where the system may include a processor configured to execute computer-readable instructions that, when executed, causes the system to carry out any of the above methods.

In some examples, the system may include a web client for providing the output (e.g., via a web-based portal). The system may include one or more databases for storing one or more rules and/or historical data, as described further below.

BRIEF DESCRIPTION OF THE DRAWINGS

Reference will now be made to the drawings, which show example embodiments of the present disclosure, and in which:

FIGS. 3a and 3b show a table of example ROI features;

FIGS. 4a-4d are diagrams illustrating progressively descriptive graph structures for examples of automatic ROI classification;

FIG. 5 is a table of notation used in the present disclosure;

FIG. 6 is a table of groupwise features calculated between ROIs;

FIGS. 7a-7b are tables of example results comparing different machine learning algorithms that may be suitable for carrying out classification of ROIs and treatment plans;

FIGS. 13a-13c show a table showing example results of classification of treatment plans;

FIGS. 14a-14c and 15a-15c show tables showing example results of classification of ROIs;

FIGS. 17a-17f show a table of example clinically relevant features that may be considered for evaluation of treatment plans;

FIG. 21 shows a table of example features that may be used for generating a proposed dose map (e.g., by performing dose inference);

FIGS. 22a-22c illustrate an example of generating a proposed dose map for automated treatment planning; and FIG. 23 shows a table showing example results of a generated proposed dose map for automated treatment planning.

DETAILED DESCRIPTION

Figure 1:
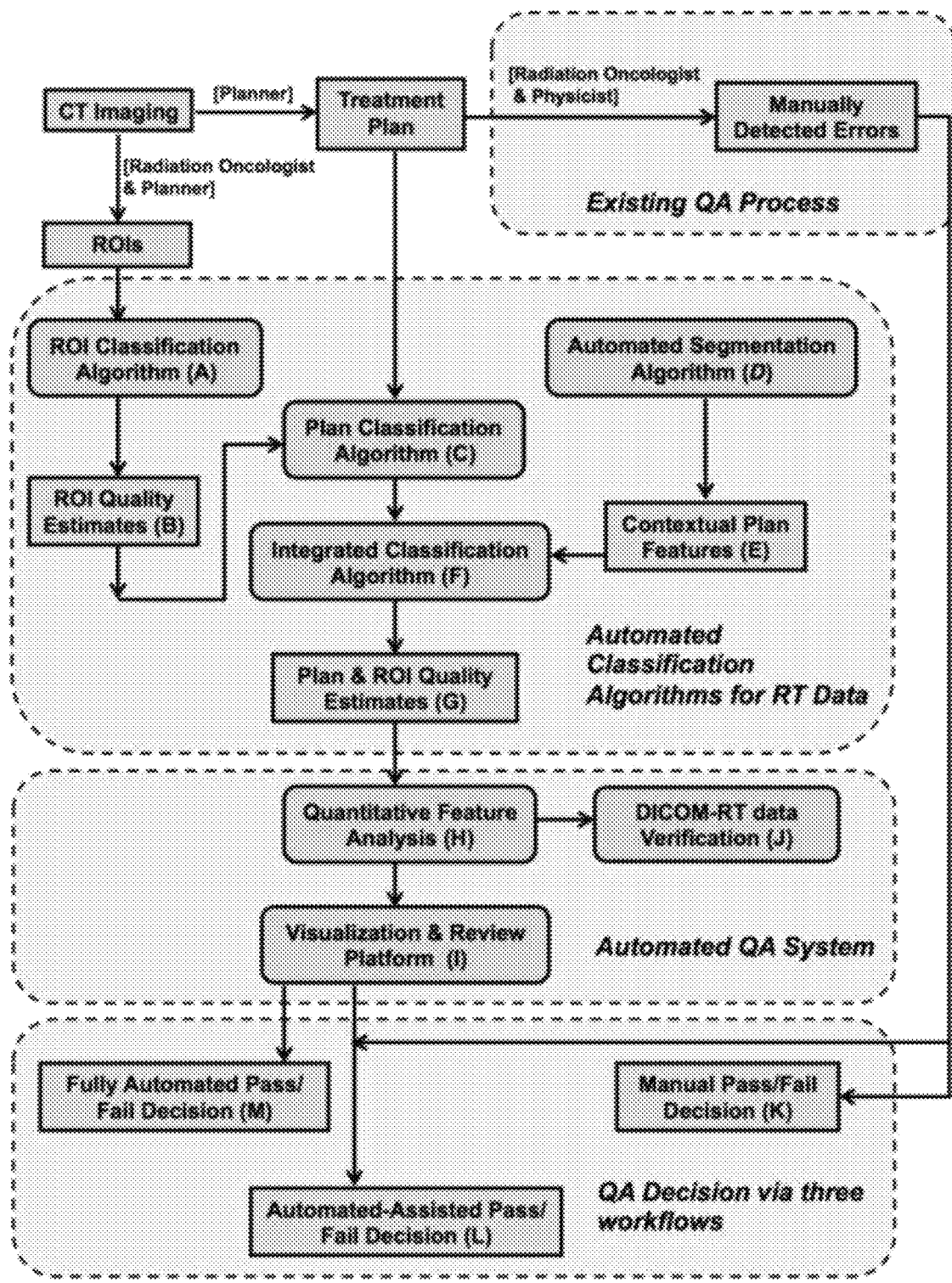
FIG. 1 is a flowchart showing an overview of an example method for automated quality assurance.

Reference will now be made to the accompanying drawings, which show example embodiments of the present disclosure. For simplicity and clarity of illustration, reference numerals may be repeated among the figures to indicate corresponding or analogous elements. Numerous details are set forth to provide an understanding of the example embodiments described herein. The example embodiments may be practised without some of these details. In other instances, suitable variations to the disclosed methods, procedures, and components have not been described in detail to avoid obscuring the example embodiments described herein, but are within the scope of the present disclosure. The description is not to be considered as limited to the scope of the example embodiments described herein.

Conventional methods of QA and treatment planning developed to date have shown promise in a limited clinical scope, however the use of more sophisticated algorithms and more data, as in various examples of the present disclosure, may have the potential to have clinical impact across a much wider array of treatments. This may include applicability across most or all treatment sites and treatment techniques.

To date there have been attempts to do simple classification of treatment plans for the purposes of establishing quality. These typically have been limited to single treatment plan classes, treatment sites and/or treatment techniques [19-23]. A possible challenge with conventional QA systems is that they typically do not have any learning component but rather compare data in treatment plans with hard-coded limits and data. Treatment site-specific templates can also be employed, however conventional templates typically cannot incorporate suitable deviations without accurate distributions of acceptable treatment planning data. As well, tools have been used to check for consistency between multiple sources of data, such as between the treatment planning system and the databases that contain data to treat the patient at the treatment unit (e.g., RT electronic medical record system and/or oncology information system).

Other conventional systems have been designed to automatically capture dose information from a novel proposed plan and compared the data with an established protocol template. Again, these conventional systems typically do not have any learning or classification components.

In some examples, the disclosed methods and systems include learning, classification, regression, and quality estimation components for ROIs and/or quality estimation that jointly consider patient and/or plan and/or ROI features. While the details vary between the key applications (ROI quality estimation, plan quality estimation), each method is a novel application for automated learning in the RT context.

Examples of the disclosed methods and systems can also improve themselves over time and repeatedly, for example using a framework for repeated training and learning. In some examples, the disclosed methods and systems may not be limited to a single site or technique but may generalize to multiple or all possible treatment sites and/or techniques, for example via the machine learning component with sufficient training data. This may be different from conventional approaches that are typically limited to single treatment sites and typically must be manually adapted to other sites, for example due to the lack of machine learning and/or generalized patient and plan features.

In some examples, the present disclosure may be extendable to include use of potentially multiple machine learning algorithms to learn different components of plans. For example, the present disclosure discusses automated QA for treatment plans and ROIs and automated treatment planning and dose inference, but the system may also consider other facets of patient care such as beams or other image features, among other possibilities. Characterization (e.g., classification) of different aspects (e.g., ROI, images, patient data and/or treatment plan) of RT treatment may be considered together in order to evaluate each based on consideration of each other aspect. This may provide a useful coarse-to-fine approach.

In some examples, the disclosed methods and systems may include learning features of the images, the treatment plans and also the ROIs, which are defined in the treatment plans, depending on what data is available in a given application. Dose inference, for example, may include zero or more ROIs to calculate features and may include zero or more previous plans for the patient or an estimate of the plan from a different source (e.g. different system, or user), but the final plan is not available. Treatment plan QA may also include a set of ROIs. This may provide more information and may also provide the ability to use ROI information that may enhance the features that can be applied. This may also allow dynamic multi-parameter evaluation incorporating both confidence levels. New data may automatically be used for future learning and testing in some examples. Therefore examples of the present disclosure may provide evaluation and also be adding to the database used for learning, which may result in a quality improvement cycle and may enable perpetual learning, to make the system more robust.

Conventional methods are typically limited in the factors that are considered when performing QA or treatment planning. The present disclosure may enable such factors to be taken into consideration. For example, in the case of dose prediction, this may include patient treatment history and genetic biomarkers that can be used as additional features. For automated treatment plan and/or ROI QA these may include, for example, delineated ROIs throughout an entire image(s) as opposed to the subset that is reviewed, the position of each leaf used to define treatment beams and segments in intensity modulated radiation therapy (IMRT) and volumetric modulated arc therapy (VMAT), and/or the joint association of the treatment plan features relative to ROI volume, location and shape, among others.

A classification and learning system may be able to incorporate one or more of these and other factors implicitly, without requiring a user to define specific parameters.

There have been conventional attempts to develop automated treatment planning based on limited anatomical and treatment plan data and applied to a single or particular treatment site/technique [27-34]. Conventional automated treatment planning methods using inverse planning approaches (e.g., IMRT and VMAT), often attempt to conform to the standard treatment planning paradigm by inferring optimization objectives based on the delineated ROIs. A possible challenge with these methods is that they always require the use of ROIs to facilitate the process and often require specific planning ROIs to be created in order to generate an acceptable treatment plan.

Optimization objectives are the clinical goals for an individual ROI specified by the user. Optimization objectives can be specified, for example, as the maximum, minimum or mean dose to a specific volume of an ROI. An optimization may specify the target ROI must receive>95% of the prescribed dose to >95% of the target volume. An optimization objective for a healthy organ ROI may specific the ROI must receive<100% of the prescription dose to 1 cc of the ROI volume, where the particular dose and volume have an associated complication or toxicity at that level.

The concept of optimization objectives for ROIs was introduced in the first implementation of IMRT, in which clinical goals were assigned for ROIs to drive the optimization process [35]. The use of ROIs allows the treatment planner (dosimetrist) the ability to articulate specific objectives to delineated structures in the plan. In addition, this enables the process to be iterated by adjusting existing objectives, adding objectives or deleting objectives. The optimization engines used to design treatment plans were predicated on this approach of specifying optimization objectives, which could readily be solved (although typically not optimally).

In the present disclosure, there is no absolute requirement on ROIs to be delineated to facilitate the automated treatment planning process. ROIs, if included, can be used to drive the learning and inference for automated treatment planning.

In addition, the optimization objectives used in conventional approaches were introduced by the clinical RT community, as optimization objectives such as these simplify the plan evaluation process, are related to relevant clinical goals and enable direct correlation with known clinical endpoints. However these optimization objectives are typically difficult to optimize, as objectives specified by dose and volume are percentiles of the dose distribution, which are non-convex from an optimization perspective. Optimization methods are better for dealing with mean and maximum doses and quadratic penalties.

In the present disclosure, the concept of optimization objectives are not required, as dose is not specified to the ROIs but rather the entire dose distribution is inferred. Therefore, instead of specifying optimization objectives for which there is a loss of spatial information, the present disclosure enable inferring the dose to each region of the patient image and encoding spatial information at the same time. Such an approach has not been implemented conventionally, possibly because it involves several components that are together complex. First, there is use of a database of previous treatment plans and imaging for the same treatment technique that can be trained and tested. Next, algorithms are used to estimate the dose distribution for a novel patient based on the previous treatment plans in the database. Finally, optimization methods are used to optimize the beam fluence required to reproduce the estimated dose distribution [36,37]. The beam fluence is the two-dimensional representation of the RT beam relating the spatial location in the beam to the beam intensity. Therefore the fluence defines the intensity modulation of a given beam, which is characterized by the shape and/or intensity of the RT beam(s) and/or the shape and/or intensity of the control point(s) for each RT beam. The optimization methods for optimizing the beam fluence in the present disclosure may present an easier problem for optimization algorithms, as there is no dependence on dose-volume objectives to be solved explicitly.

Example System Overview

Figure 2:
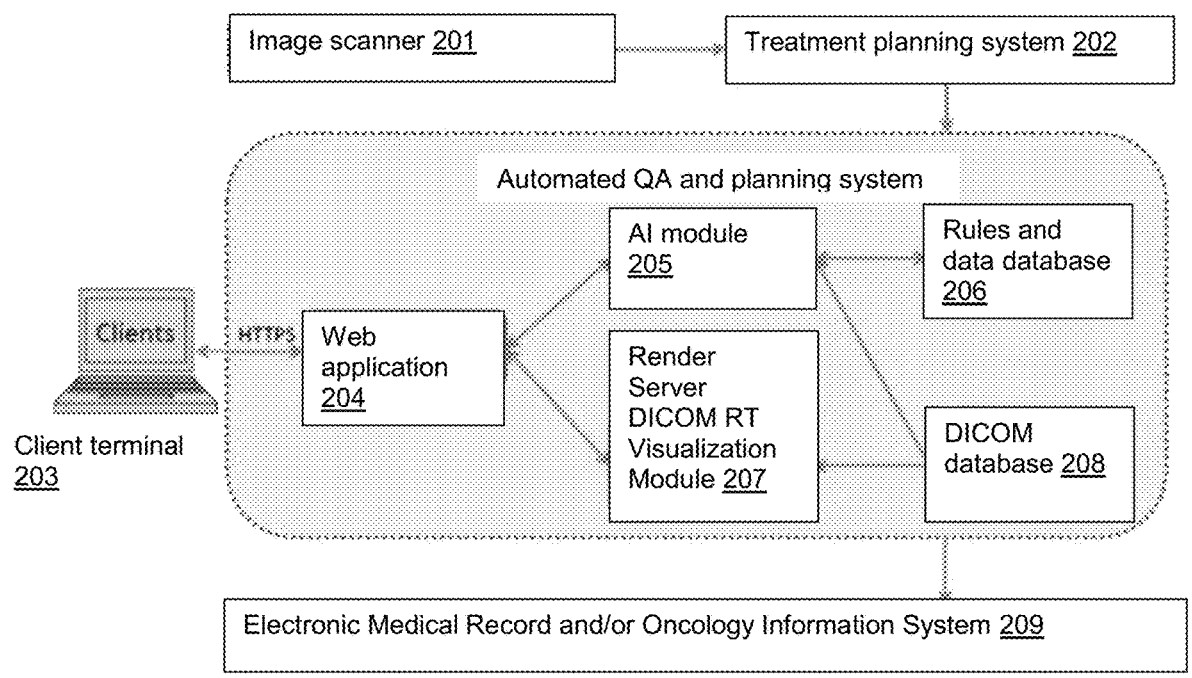
FIG. 2 is a block diagram of an example system for carrying examples of the disclosed methods.

FIG. 2 shows an overview of an example system suitable for carrying out examples of the present disclosure, as will be discussed further below. The example system may include any suitable computing devices including, for example, one or more servers and/or one or more mobile computing devices (e.g., handheld devices, tablets, mobile communication devices, laptops and smartphones). The example system may communicate with other systems (e.g., external databases or external servers). Although FIG. 2 illustrates scanners 201, treatment planning system 202, RT electronic medical record system 209 and/or oncology information system and clients 203 in addition to an automated QA and planning system, the example system may include only the automated QA and planning system, with the other components being separate from and external to the system.

The example system may include a processor that communicates with one or more memories storing data and computer-readable instructions that, when executed by the processor, causes the system to carry out the disclosed methods.

The system may include one or more databases 206 storing the one or more rules and/or historical data. The system may also communicate with one or more external databases (not shown) for accessing such information, for example. Information in the database(s) may be updated (e.g., as new patient data and new treatment plans are available).

The example of FIG. 2 may implement a web-based module and visualization engine. The modular design of the system may limit the scope of each module to a specific task. This may allow a module to be reused in other systems. For example, the Artificial Intelligence (AI) module 205 may be used by a web application 204 for plan quality review and/or for automated treatment planning. The same module can also be used by a treatment planning system (discussed further below) to aid in creating ROIs, for example.

Modular design of the example system may also allow it to scale to support a growing user base. Each piece can run on separate clusters of servers. Alternatively, to save on costs it can all run on the same server.

This modular design may enable separate presentation of various views of the data—which may be running on a client 203—from the massive amount of plan related data—which may be stored on a separate server. Money can be invested in high quality server hardware capable of storing and processing large volumes of data, while the client equipment can be relatively basic (such as a laptop or a tablet), to review portions of the data served to the client over the network.

In some examples, the system may include a web application 204 for receiving user input and providing the output, where the output is web-accessible. This web 2.0 application 204 may tie together various algorithms and technologies and may present them to the user via a web interface. The web application 204 may be an implementation of a workflow engine for a radiation treatment plan—e.g., data constituting a proposed treatment plan may be passed through a rigorous clinical approval process with artificial intelligence algorithms aiding each step of the process, and may require a human user to sign off. Through the web application 204, the user can see the automatic artificial intelligence algorithm quality assessment, visualize all the RT Plan elements including patient scans, delineated regions of interest, beams and computed dose, and finally mark the plan as approved or rejected for delivery, for example.

The web application may be stand-alone, or link to existing QA or planning software suites, for example.

The web application 204 may allow ubiquitous access. Users can use desktops, laptops and tablets, or any other suitable computing device to access the service. Users may have the ability to access the application 204 from anywhere in the world (e.g., using an internet connection).

All traffic may be encrypted (e.g., via HTTPS) and users may require to be authenticated, to ensure security and patient privacy.

The example system may include an artificial intelligence (AI) module 205. This module 205 may implement machine learning classification and quality assurance algorithms, such as described below. The module 205 may expose its functionality via a remote procedure that calls API.

The example system may include a render server DICOM RT visualization module 207. The DICOM RT Visualization module 207 may handle render requests for DICOM treatment plan data. Algorithms in this module 207 may be able to render various scanned images, beams, regions of interest, and dose. The module 207 may be also able to compute dose-volume histograms. The module 207 may expose its functionality via a remote procedure that calls API. This may allow web-based thin clients (such as the web application 204 running in a web browser) to render DICOM RT data for the user and may let the user to interactively visualize the data.

The example system may include one or more rules and data databases 206, which may store historical data (e.g., plan features and patient features) and rules for implementing automated QA and/or automated treatment planning, as discussed below. The machine learning algorithms may be trained on a relatively large set of features. This database(s) 206 may be a storage location for all those features. The database(s) 206 may include a collection of high quality training data extracted from tens of thousands of clinical plans.

The example system may include a DICOM database 208. This may be a repository for storing DICOM treatment plan data. A high performance, DICOM compliant storage system may need to be used here to handle the relatively large number (e.g., tens of thousands) of plans the system may be expected to handle.

Automated QA: Overview of Example Method and System

FIG. 1 shows an overview of an example method for quality assurance in greater detail, as will be discussed further below.

In some examples, the disclosed methods and systems may use machine learning to build an automated method for treatment plan QA. Imaging and treatment planning data may be grouped according to treatment site and treatment technique. Clinically relevant features (e.g., as shown in Table 8, FIGS. 17a-17f) may be selected by a multi-disciplinary RT team to ensure that the automated learning is based on diverse knowledge.

Features may be extracted from historical training data, and used to construct the learning algorithms and train the QA model. Additional features, not found directly in the treatment plan, may be automatically generated by applying segmentation algorithms which can delineate relevant organs in the RT image dataset.

Evaluation of proposed treatment plans may go through the following steps: 1) feature calculation; 2) classification and quality estimation; and 3) QA review. Retrospective plans that were classified as clinically unacceptable may be used to assess the ability of the algorithm to capture known errors and quantify expected deviations from clinical practice.

In some examples, the automated QA review process may be integrated with existing clinical QA functionality by adding the following components: i) an analysis mechanism to provide feedback to the team quantitatively detailing the underlying classification results; ii) a plan review and approval system that may be combined with a comprehensive DICOM-RT based image and visualization platform to provide a complete integrated solution; and iii) an interface to the DICOM-RT database that may be accessed by the radiation treatment machine (e.g., linear accelerator) for actually programming the delivery of radiation the patient is to receive in order to report any inconsistencies between databases, potentially contributing to errors in treatment delivery and patient safety.

Data verification may play a role in RT. Plans may be exported into and out of various different software packages, and/or transmitted across networks. In some cases bit level comparisons of the plans may be appropriate, but when plans are exported from different software packages this may not be appropriate. For example, at one point during the process the order of the beams could be changed in the DICOM file. This does not represent any change at all to treatment quality, but may change the bit-level comparison results, producing an erroneous result that the two plans are different. In some examples, the disclosed methods and systems may enable data verification at a higher level.

The inputs into the example of FIG. 1 have been simplified for illustrative purposes and may include: treatment planning data, imaging data and regions of interests (if delineated, either manually, semi-automatically or completely automatically). Other sources of data not represented in the figure may include previous outcomes data, including treatment related toxicity, survival data and recurrence data; data related to treatment delivery such as specifications of the treatment delivery unit; or any other data pertinent to patient treatment. Any patient information or plan feature useful for a physician to make an accurate decision about the treatment plan may be included, and that information may be considered jointly as opposed to independently [23].

In the example shown, the automated QA process may include various interconnected sub-components, including:
ROI classification and quality estimation algorithm (A),
treatment plan classification and quality estimation algorithm (C),
automated segmentation algorithms (D),
data comparison/integrity algorithm (J),
source of error algorithm (H),
visualization platform (I),
review and approval platform (I).

In the training phase, labelled ROIs and treatment plans may be used to train an algorithm for ROI and plan classification and quality estimation. This algorithm may be further broken into sub-components pertaining to ROI classification and quality assessment, plan classification and quality assessment, and finally an integrated ROI and plan algorithm (blocks K, L and M, in FIG. 1). The ROI classification algorithm may be trained on a database of example ROIs with known labels (e.g., heart, lung, etc.). The treatment plan classifier may be similarly trained on a database of example plans with known class.

Evaluation of a proposed treatment plan is now discussed. Once the proposed treatment plan, medical images, and ROIs are prepared the next phase may be to automatically classify the data and provide estimates of plan and ROI quality using the learned components and classifiers from the training phase. The basic pipeline may include the following:

Images may be first acquired. CT is predominately used in RT for treatment planning although other imaging modalities can also be used instead, or in addition to augment the information for treatment planning.

From the desired imaging datasets, ROIs may be delineated manually, semi-automatically or completely automatically. This task may be done by either the radiation oncologist or the planner. The treatment planner (dosimetrist) may then generate a treatment plan including the image dataset(s), ROIs, defined anatomical points to facilitate treatment planning, treatment beams to treat the patient, the prescription dose to establish the amount of radiation the target is to receive, and other such aspects.

The generated treatment plan may be then subject to technical and clinical review as part of the RT QA process. A medical radiation physicist and the radiation oncologist may review the plan and determine the clinical applicability of the plan.

The ROIs may be parsed and features extracted for the purposes of classifying each ROI in the treatment plan (block A). For each ROI, estimates of the quality may be provided for review and to establish the confidence with which the ROI corresponds to a known ROI class (block B). This may address both labelling errors (e.g., the planner labelled the heart ROI as lung) and quality errors (e.g., the heart ROI is very poorly contoured and contains a lot of lung, spinal column, etc.). These errors can negatively affect treatment planning. In different examples, this step may take place before an initial plan is generated, or after, for example depending on the desired work flow of the target hospital.

The treatment plans may be parsed and features extracted for the purposes of classifying the treatment plan with respect to the known treatment plan classes (block C). As previously noted, this step can optionally take place after the planner has reviewed ROI quality estimates to ensure there are no errors before generating the plan.

Automated segmentation algorithms may be run to ensure that a minimum number of ROIs exists in each treatment plan (block D). The automated segmentation may generate ROIs automatically using standard segmentation algorithms and the features from these ROIs may be extracted using the methods of the ROI classification algorithm (block E). For example, the external outline of the patient may always be segmented in addition to the lungs (e.g., in thorax images), the pelvis (e.g., in abdominal images) and the skull (e.g., in head images). The features from these ROIs may then be added to the classification algorithm to aid in plan classification and help ensure there is consistent data used for the classification process (block F).

An integrated plan and ROI algorithm may then prepare the final estimates of plan and ROI quality estimates using information from the plan, the ROIs, and any additional automated segmentations available (block D). Similar to the ROI classification and quality estimation algorithm, plan and ROI quality estimates may be generated from the integrated classification algorithm. This may also provide a confidence for the selected treatment plan class (block G).

In addition to providing an overall plan and ROI quality estimates, the example method may provide estimates of what caused the low quality score. This may help give the planner an idea of what to change. This may take place in the quantitative feature analysis box (block H). Any manually desired checks on the plan may also take place at this stage, ensuring, for example, if there is a known clinical tolerance for a healthy organ (e.g., the spinal cord dose must be less than a certain dose or the target must be covered by a dose greater than or equal to a given prescription dose).

In some examples, the output may also providing indication of quality estimates for the plan and/or ROI that fall in a particular value range, such as being particularly high, and what caused the high quality estimates. This may provide useful information to the user that certain parameters should be kept unchanged.

The plan and ROI quality estimates may be incorporated into the QA process in various ways such as:

The automated system may not be used and the RT team may render a clinical decision using only the visualization system alone (block K).

The system may be used to augment the current clinical process and provide the RT team with a review of data from the feature extraction and with confidence that the plan belongs to a particular plan class and achieves the desired clinical criteria (block L).

The system may be used to render a clinical decision based on the treatment plan class that has the highest confidence. From this point, the clinical criteria for that plan class may be used for further analysis without requiring input from the RT team (block M).

Optionally, the system may enable a direct comparison between treatment plan features that exist in the treatment plan and the same features that would be present in the record, and may verify a database accessed by the radiation treatment machine (e.g., linear accelerator) for actually programming the delivery of radiation the patient is to receive (block J).

Figure 18:
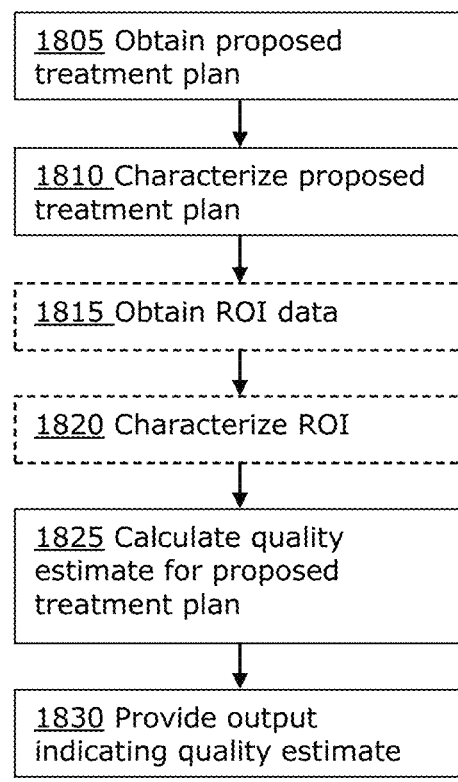
FIG. 18 is a flowchart of an example method for evaluating a proposed treatment plan.

An example method for evaluating the quality of a proposed treatment plan is illustrated in FIG. 18. This method may be carried out using any suitable computing system, such as the example system of FIG. 2.

At 1805, a proposed treatment plan is obtained (e.g., automatically, from another system or manually entered). The proposed treatment plan may define RT treatment for at least one treatment site. A set of patient data (e.g., including patient features, such as a patient characteristic, a patient history, a patient diagnosis, and an imaged feature, as discussed below) for the patient may also be obtained. There may also be one or more patient treatment requirements (e.g., limitation to permissible radiation dose, based on institutional guidelines) that may or may not be specific to the patient.

At 1810, the proposed treatment plan may be automatically characterized according to one or more predefined features to determine the treatment plan characterization.

Characterizing the proposed treatment plan may include determining a treatment plan class for the proposed treatment plan according to one of a plurality of predefined treatment plan classes. This may be carried out using an automated classification algorithm, as discussed below. In some examples, the automated classification algorithm may be developed by machine learning (e.g., based on Random Forest techniques, as discussed below) using historical data. Where machine learning is used, such learning may be ongoing, as additional historical data becomes available, such that the classification of a given treatment plan may be refined over time, for example.

Characterization of the proposed treatment plan, such as classifying the proposed treatment plan, may be based on determining the similarity (e.g., as calculated through distances) of features of the proposed treatment plan to features of known predefined treatment plan classes or characteristics.

Characterizing the proposed treatment plan may also include determining a quality estimate that the proposed treatment plan belongs to a given treatment plan characterization, based on predefined expected features of the given treatment plan characterization. The proposed treatment plan may be characterized according to various treatment plan features, for example, including one or more of: an anatomical site, a tumour histology, a prescription dose, a treatment technique, and a treatment intent.

Optionally, at 1815, ROI data may be obtained (e.g., from another system or manually entered). The ROI data may delineate at least one ROI in a set of image data, where the image data may be of the treatment site and may be included as part of the patient data. The ROI may be delineated manually, semi-automatically or fully automatically. In some examples, the ROI may be automatically segmented from the image data by the system, as part of the example method.

If there is ROI data, at 1820 the ROI may be automatically characterized according to one or more predefined features to determine at least one ROI characterization. Similarly to 1810, characterizing the at least one ROI may include determining at least one ROI class respectively for the at least one ROI, according to one of a plurality of predefined ROI classes, using the same or different automated classification algorithm. For example, the automated classification algorithm for classifying the ROI may be developed by machine learning using historical data. The automated classification algorithm may be based on determining similarity of features of the ROI to features of a predefined ROI class.

The ROI characterization may be determined based on shape and density value of a given ROI, for example. The ROI may be characterized according to ROI features including one or more of: anatomical correspondence, tumours, dosage, regions to avoid, regions for dose evaluation, reference structures and structures to facilitate treatment planning, for example, and as discussed further below.

At 1825, a quality estimate (or confidence level) for the proposed treatment plan may be calculated. The quality estimate may be calculated as a confidence value, a simple pass/fail determination, or any other suitable estimate of quality. The calculation may also include determination of how well certain plan features match with expected plan characteristics and may include generation of error and/or warnings if the quality estimate is below a certain threshold value.

The quality estimate may be calculated by evaluating the proposed treatment plan according to one or more rules defining expected relationships between the treatment plan characterization and one or more of: one or more plan features, and one or more patient features defined in the set of patient data.

The rule(s) may be defined (e.g., predefined manually) or machine-learned based on historical data of historical treatment plans, as discussed further below. Where machine learning is used, such learning may be ongoing, as additional historical data becomes available, such that the rule(s) may be refined over time, for example. The historical data of historical treatment plans may include treatment outcome data. Rules defining expected relationships may include, for example, one or more of: historical suitability of a given treatment plan characterization for historical patients; historical treatment outcome of a given treatment plan characterization for historical patients; historical treatment plans for a specific patient; historical treatment outcomes for the specific patient; a mathematical function; and a general rule governing treatment plans irrespective of the treatment plan characterization and irrespective of the patient data; among others.

Where there is ROI data, calculating the quality estimate for the proposed treatment plan may also include evaluating the proposed treatment plan according to one or more rules defining expected relationships between the treatment plan characterization and the at least one ROI characterization. Where there is ROI data, calculating the quality estimate may include calculating a quality estimate that a given ROI belongs to a given ROI characterization, based on predefined expected features of the given ROI characterization.

Where there is one or more patient treatment requirements, calculating the quality estimate may include evaluating whether the treatment plan characterization satisfies the patient treatment requirement(s).

At 1830, output indicating the calculated quality estimate may be provided. For example, a report may be generated and displayed to the user on a display device (e.g., display screen of any suitable computing device) and/or may be printed. The output may be provided via a web portal. For example, a user may access the example system through a separate client device (e.g., a mobile computing device, such as a tablet or a smartphone) via a web-accessible portable provided by the system. This may enable greater mobility and flexibility for user interaction with the system. The report may be stored for further processing and/or future reference in an internal or external memory of the system, for example.

The output may include one or more suggestions for modifying the proposed treatment plan (e.g., modifying ROI delineation, beam configuration, etc.) in order to improve the quality estimate. The output may also include one or more features of the treatment plan characterization that is relevant to the quality estimate. For example, if the proposed treatment plan was found to have low quality because of a mislabelled ROI, the output may include indication of the mislabelled ROI and that this error contributed to a low quality estimate.

Similarly, the output may include one or more suggestions for what parameter (e.g., a particular ROI or a particular beam geometry) should be kept unchanged. For example, a parameter that was determined to have contributed to an increase in the quality estimate may be indicated as a parameter that should be kept unchanged.

The output may include the calculated quality estimate and/or plan features and/or ROI features for the proposed treatment plan, as compared to the quality estimate and/or features from the historical plan class and/or ROI class of interest.

Thus, the example method for evaluating the proposed treatment plan may enable estimation of the quality of a proposed treatment plan based on an integrated consideration of plan features optionally together with ROI features, patient features, and other considerations (e.g., treatment requirements), for example.

Figure 19:
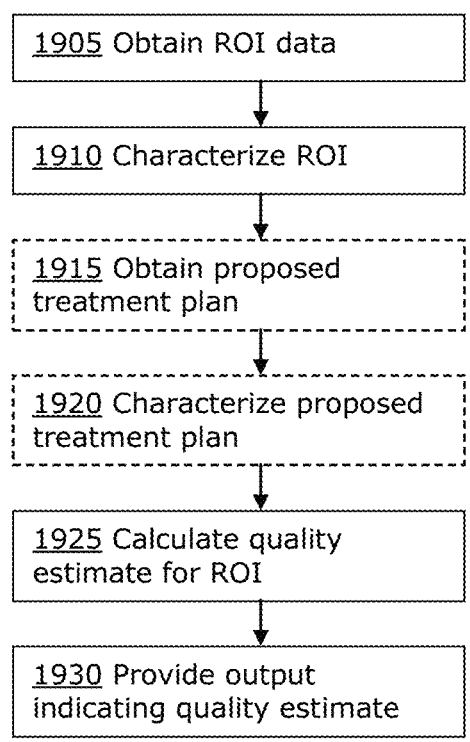
FIG. 19 is a flowchart of an example method for evaluating a ROI.

An example method for evaluating the quality of a delineated ROI is illustrated in FIG. 19. This example method may be similar to the example method of FIG. 18, and may be carried out using any suitable computing system, such as the example system of FIG. 2.

At 1905, a set of ROI data may be obtained (e.g., entered manually, obtained from another system or automatically segmented by the system from image data). The ROI data may delineate at least one ROI for at least one treatment site in a set of image data. A set of patient data (which may include one or more patient features, as discussed further below) for a patient may also be obtained. One or more patient treatment requirements may also be obtained, as discussed above.

At 1910, the ROI may be automatically characterized according to one or more predefined features to determine at least one ROI characterization. This may be similar to 1820 discussed above (e.g., using an automated classification algorithm or other characterization techniques), and such discussion need not be repeated here. Characterizing the ROI may include determining a quality estimate that the ROI belongs to a given ROI characterization, based on predefined expected features of the given ROI characterization. The ROI may be characterized according to one or more ROI features including one or more of: anatomical correspondence, tumours, dosage, regions to avoid, regions for dose evaluation, and a reference structure, among others, as discussed further below.

Optionally, at 1915, a proposed treatment plan may be obtained (e.g., entered manually or communicated from another system). The proposed treatment plan may define treatment for the at least one treatment site, as discussed above.

If there is a proposed treatment plan, then at 1920 the proposed treatment plan may be automatically characterized according to one or more predefined features to determine a treatment plan characterization. This may be similar to 1810 discussed above (e.g., using an automated classification algorithm or other characterization techniques; and optionally including determination of a quality estimate for the proposed treatment plan as discussed above), and such discussion need not be repeated here.

At 1925, a quality estimate may be calculated for the ROI by evaluating the ROI according to one or more rules. The rules may define expected relationships between the ROI characterization and one or more of: one or more ROI features, and one or more patient features defined in the set of patient data. Similar to 1825 discussed above, the rules may be defined (e.g., predefined manually) or machine-learned based on historical data of historical ROIs. Rule(s) may define expected relationships, for example including one or more of: historical suitability of a given ROI characterization for historical patients; historical treatment outcome of a given ROI characterization for historical patients; historical ROIs for a specific patient (this may include relationships based on ROI features, for example that heart ROIs are associated with a round shape, and this may be dependent on the context of the patient's image data); relationships between different ROIs within a specific patient (e.g., smaller lung ROIs may be expected to be associated with a smaller heart ROI); historical treatment outcomes for the specific patient; a mathematical function; and a general rule governing ROIs irrespective of the ROI characterization and irrespective of the patient data; among others.

The quality estimate may be calculated as a confidence value, a simple pass/fail determination, or any other suitable estimate of quality. The calculation may also include determination of how well certain ROI features match with expected ROI characteristics and may include generation of error and/or warnings if the quality estimate is below a certain threshold value.

Where there is a proposed treatment plan, calculating the quality estimate may include evaluating the ROI according to one or more rules defining expected relationships between the ROI characterization and the treatment plan characterization.

Where there are one or more patient treatment requirements, the quality estimate may be calculated based on evaluating the ROI according to one or more rules defining expected relationships between the ROI characterization and the patient treatment requirement(s).

At 1930, output indicating the calculated quality estimate may be provided, similar to 1830 above (e.g., output may include guidelines for improving the quality estimate, may include information relevant to the quality estimate, may be provided in the form of a report and/or accessible via a web portal, etc.). Such discussion need not be repeated here in detail. The above description may be implemented using the example system of FIG. 2. For example, the example system may include: 1) The classification and quality estimation algorithms described above providing quantitative analysis of the each treatment plan and ROI in the plan (e.g., to carry out block H in FIG. 1; and blocks 1810 and 1820 in FIG. 18); and 2) the visualization and review platform which may provide a user with the ability to interrogate treatment plans and may provide a mechanism for review to render a clinical decision as to the clinical acceptability of the plan (e.g., to carry out block I in FIG. 1; and block 1830 in FIG. 18).

Automated Treatment Planning: Overview of Example Method and System

As discussed above, the present disclosure enables automated treatment planning without the requirement for delineated ROIs in the patient's image data. However, it may be the case that ROIs have been delineated in the historical data stored in the system database. Additionally, the disclosed method may still be carried out where the image data do include ROIs.

If, for a particular treatment plan class to be planned, ROIs have been delineated in the training database then:
1) If there are ROIs for the novel patient image data, a dose distribution can be inferred based on ROI specific features and optionally also non-ROI specific features such as texture, density etc in the image as it relates to the dose distribution.
2) If there are no ROIs for the novel patient image data, a dose distribution can be inferred based on features that are not dependent on the ROIs.

If, for a particular treatment plan class to be planned, ROIs have not been delineated in the training database (e.g., in the case of simple treatment plans that are palliative in nature) then:
1) If there are ROIs for the novel patient image data, a dose distribution can be inferred based on features that are not dependent on the ROIs as there are no ROIs in the treatment plan class to calculate ROI-based features.
2) If there are no ROIs for the novel patient image data, a dose distribution can be inferred based on features that are not dependent on the ROIs.

In some examples, the disclosed method may be advantageous over conventional automated planning approaches in one or more ways, such as:
The entire dose distribution for the patient may be planned.
ROIs may not be required to infer the dose distribution.
Where ROIs are present in the patient image data, ROIs may be used to drive the inferred dose distribution using ROI-based features as they relate to the dose distribution.
Dose-volume objectives may not be required.
A dose distribution may be inferred for even simple cases that would not require an optimization engine for conventional treatment planning.

Figure 20A:
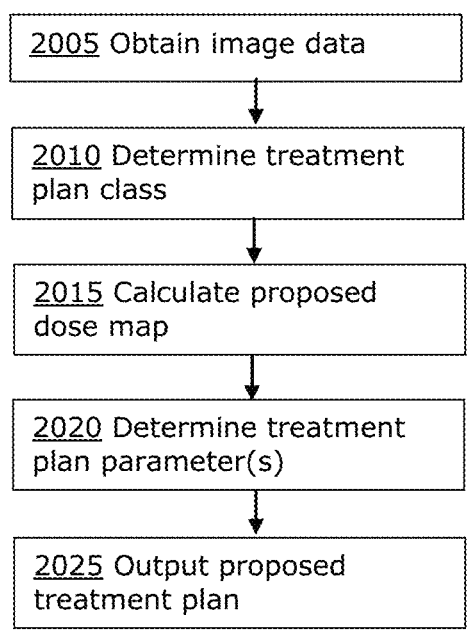
FIG. 20a is a flowchart showing an overview of an example method for automated treatment planning.
Figure 20B:
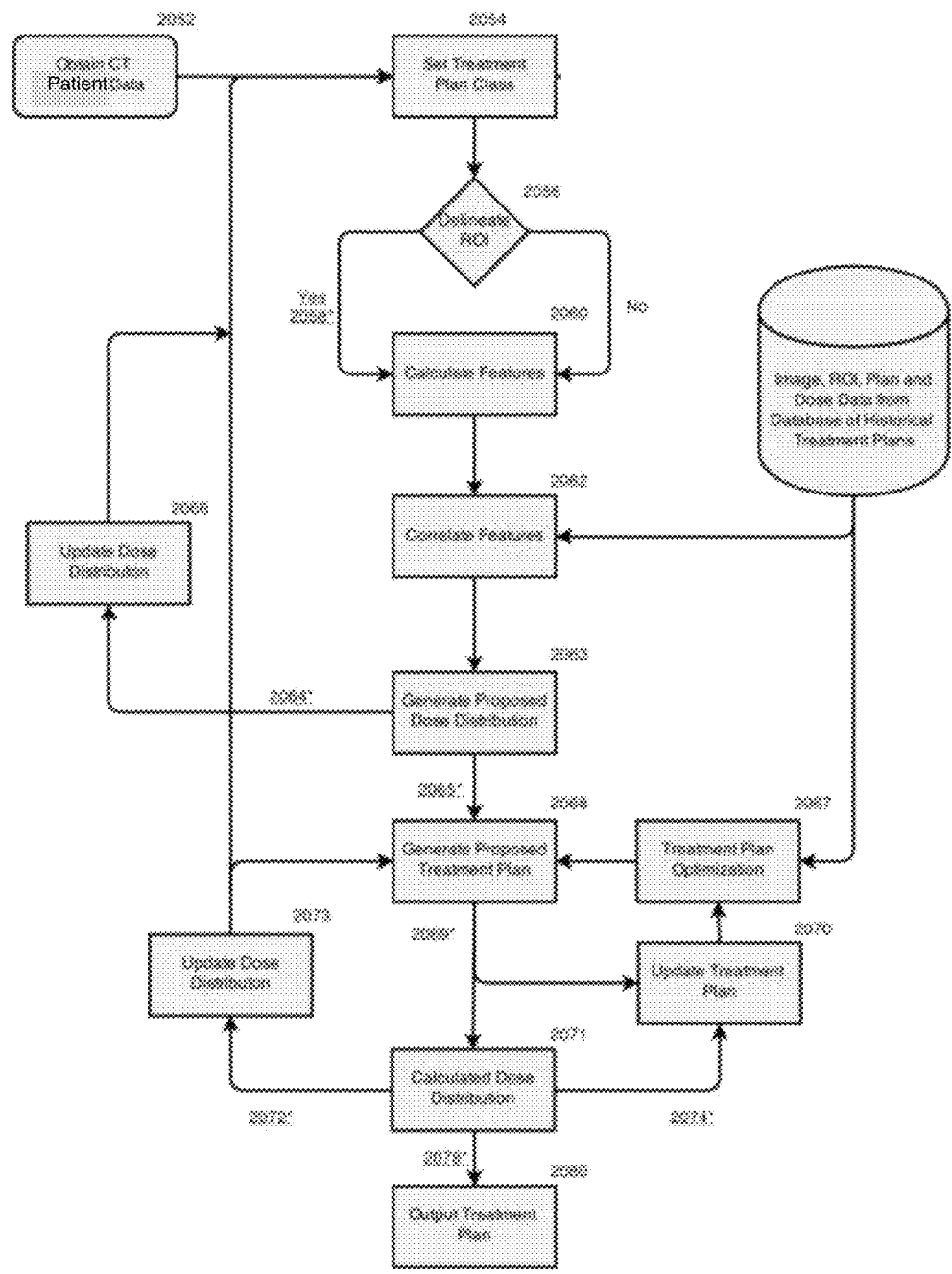
FIG. 20b is a more detailed flowchart of an example method for automated treatment planning.

An example method for generating a proposed treatment plan is shown in FIG. 20a. This method may be carried out using any suitable computing system, such as the example system of FIG. 2. FIG. 20b, discussed further below, illustrates further details of the example method.

At 2005, a set of patient data is obtained, including at least a set of image data for the patient. The patient's image data may or may not include delineated ROIs.

At 2010, a treatment plan class is determined. A treatment plan class is a broad categorization or characterization of the intended treatment. A plurality of treatment plan classes may be predefined (e.g., based on categorization of historical data). Each predefined treatment plan class may define one or more treatment plan features (e.g., tissues to avoid or dosage to use) for a respective treatment site. For example, a treatment plan class may be a breast treatment or a prostate treatment. The treatment plan class is used to determine the rules to be used for generating the proposed treatment plan, as discussed further below. Determination of the treatment plan class may be carried out at least based on the image data (e.g., using an automatic classification algorithm). Additionally or alternatively, the determination of a treatment plan class may be based on user input. For example, a user might provide input indicating that the treatment is to be a breast treatment; alternatively, the image data may be automatically analyzed to determine that the image is that of a breast with a tumour and accordingly the treatment should be a breast treatment.

At 2015, a proposed dose map is calculated. This calculation may be carried out using inference techniques, as discussed further below. The proposed dose distribution (also referred to as a dose map) may define the proposed dosage over a volume of the image data (e.g., on a voxel-by-voxel basis). The proposed dose map may be calculated in accordance with a set of rules defining relationships between applied dosage, the treatment plan class and at least one feature of the image data. These rules may include rules generated by computer learning based on historical data, may include mathematical functions, and may include hard rules that are manually inputted, for example.

The proposed dose map may be inferred on a voxel-by-voxel basis. Each voxel may be characterized based on one or more appearance features (e.g., density). Then, the set of rules may be used to relate the voxel feature(s) to the treatment plan class and optionally other patient features. For example, for a breast treatment plan class, a voxel may be characterized as breast tissue, and the patient data may indicate that the patient is a 24 year old. The set of rules may then include a rule indicating that, for a breast treatment plan, breast tissue for a young adult should receive a specified dose. Such a rule may have been learned based on historical data showing that similar patients undergoing breast RT received similar dosages for breast tissue, for example.

At 2020, one or more treatment plan parameters are determined in order to achieve the proposed dose map. The treatment plan parameters may be determined in accordance with another set of rules, which may include optimization algorithms, and may include manually inputted rules, for example. The treatment plan parameters may include beam parameters (e.g., beam shapes, beam intensities and beam modulation), for example, and may be determined in accordance with beam optimization algorithms.

At 2025, the proposed treatment plan is generated and outputted. The proposed treatment plan includes the one or more determined treatment plan parameters. The proposed treatment plan may be outputted visually (e.g., displayed on a screen) and/or may be transmitted to a database for future consideration.

FIG. 20b illustrates an example method for automated treatment planning in greater detail.

At 2052, the set of patient data, including the set of image data, such as CT imaging data, is obtained. The set of patient data may include, for example, patient features, such as a patient characteristic, a patient history, a patient diagnosis, and an imaged feature.

Optionally, in addition to the patient data, there may also be one or more patient treatment requirements (e.g., limitation to permissible radiation dose, institutional guidelines, clinical protocol, clinical trial criteria) that may or may not be specific to the patient.

Optionally, ROI data may be obtained (e.g., from another system or manually entered). The ROI data may be included in the image data or may be a separate set of data. The ROI data may delineate at least one ROI in the set of image data. The ROI may be delineated manually, semi-automatically or fully automatically. In some examples, the ROI may be automatically segmented from the image data by the system, as part of the example method. ROIs may be characterized using an automated classification algorithm, for example as discussed above with respect to the automated QA method and system. In some examples, the automated classification algorithm may be developed by machine learning (e.g., based on Random Forest techniques, as discussed below) using historical data.

At 2054, the treatment plan class is set. The treatment plan class may be one of several predefined treatment plan classes. The treatment plan class may set be based on manual input from the user (e.g., the user may manually enter input specifying the desired treatment plan class), based on an electronic medical record (e.g., the patient data may be referenced to a patient recording including information about the necessary treatment for the patient) and/or based on automated classification of the image data (e.g., using any ROIs, features of the image data, such as the pulse sequence used and/or physiological features in the image) and/or the imaging protocol used.

If the treatment plan class is automatically determined, this determination may be based on a comparison of the inputted patient data with historical data, to determine the similarity of the inputted patient data to previous patients and the treatment plans used. This automatic classification may be performed using machine learning. Where machine learning is used, such learning may be ongoing, as additional historical data becomes available, such that the classification of a given treatment plan may be refined over time, for example. Determining the treatment plan class may be based on determining the similarity (e.g., as calculated through distances) of features of the image data to features of historical image data which have historical treatment plans.

If the treatment plan class is determined based on the electronic medical record system and/or the oncology information system and/or based on automated classification, a prompt may be generated requesting the user to approve or reject the determined treatment plan class.

A treatment plan class would define, for example, the site of treatment i.e. prostate, breast, lung, and/or the histology of the disease i.e. non-small cell, mesothelioma, and/or the prescribed dose i.e. 7800 cGy in 39 fractions, 800 cGy in 1 fraction, and/or the treatment technique i.e. static beams, IMRT, VMAT, and/or the clinical intent i.e. radical, palliative, pain management, The proposed treatment may define RT treatment for at least one treatment site.

At 2056, after a treatment plan class has been set, it is determined whether there is ROI data.

Optionally, at 2058, if there is ROI data, the ROI may be manually or automatically characterized according to one or more predefined features to determine at least one ROI characterization, for example similarly to that described above for the automated QA method and system. In some examples, where ROI data is not provided as input data, ROI data may be automatically generated by automatically segmenting one or more ROIs from the image data. The ROI data, whether provided as input or automatically generated, may be evaluated for quality, for example as described above.

At 2060, one or more features that will serve as the basis for generating the proposed treatment plan may be calculated. The features that are calculated for the proposed treatment plan may be based on the determined treatment plan. For example, the features that would be calculated for a given set of patient data may be based on the set of image data (and ROI data if available).

The calculated features may include features extracted from the data provided at 2052 (e.g., images, ROIs, patient history, etc.). The set of features may or may not include features specific for the treatment plan class. Features of the image data may include non-ROI features, such as characterization of image portions (e.g., voxels) or the entire image. For example, the image data may be characterized according to the texture and/or intensity of portions of the image.

Intensity refers to the intensity (or magnitude) of an image signal in a given portion of the image. In the case of CT images, this quantity is also referred to as density. Texture is a feature extracted from an image by examining the intensity patterns. So, for example, an image region full of small circles would have a different texture than an image region full of small squares. Such characterization may enable characterization of the intensity patterns in an image portion or entire image. Techniques for characterizing intensity of image data include, for example, textures, localized histograms, gradients, or other pattern-recognition techniques.

This characterization may be used to measure, estimate and/or represent the different anatomies and geometries of image data. For example, this may enable a heart-like region in the image that is near the lung to be characterized as being different from a heart-like region in the image that is in the middle of the heart.

Use of non-ROI image features may complement ROI data, where available. For example, even if a heart ROI has been delineated in the image data, non-ROI characterization may still be used to characterize where a given voxel is within the heart.

At 2062, the features calculated in 2060 may be correlated with historical data (e.g., from a database of historical image data, historical ROI data and/or historical dosage data). This correlation may be carried out based on the treatment plan class, so that the most appropriate historical data is referenced.

Based on the correlation, at 2063, a proposed dose map (also referred to as a proposed treatment dose distribution) may be calculated. The proposed dose map may be calculated as a scalar voxel-by-voxel dose distribution corresponding to the input image data, or at a lower or higher spatial resolution, and may or may not include a confidence estimate or probability distribution at each location specifying the confidence of the estimation and/or the probability of different dose levels. The calculation may also include determination of how well certain image and/or ROI features match with expected characteristics and may include generation of error and/or warnings if the quality of the image data at a given location is estimated to be insufficient to determine dose at that given location.

The proposed dose map may be tailored according to a first set of one or more rules defining expected relationships between applied dosage, the treatment plan class, and one or more patient features defined in the set of patient data.

The rule(s) may be defined (e.g., predefined manually) or machine-learned based on historical data of historical treatment plans and the associated dose distribution of the treatment plans in the treatment plan class. Where machine learning is used, such learning may be ongoing, as additional historical data becomes available, such that the rule(s) may be refined over time, for example. The historical data of historical treatment plans may include treatment outcome data. Rules defining expected relationships may include, among others, one or more of:

historical suitability of a historical dose map for the treatment plan class (e.g., inferring the dose distribution for the patient based on historical treatment plans and their associated dose distributions);

historical treatment outcome of a given dose map for historical patients (e.g., considering the known outcomes of historical dose distribution to tailor the proposed dose map for achieving a desired outcome);

historical dose maps for a specific patient (e.g., where a previous treatment plan for the same patient is stored in the database, the same or slightly altered dose map may be suitable);

historical treatment outcomes for the specific patient (e.g., where a previous treatment outcome for the same patient is stored in the database, the dose map may be copied from the historical data if the currently desired treatment outcome is the same);

a mathematical function (e.g., a regression algorithm or function relating dose values to image features, such as f(x) where the output is a dose value and x is a set of image features); and a general rule governing dose maps irrespective of the treatment plan class and irrespective of the patient data (e.g., the patient cannot receive more than a specified dosage), which may be entered manually.

The proposed dose map may have an associated voxel-by-voxel variability (distribution of possible doses), which can be used to tailor the dose distribution on a plan class by plan class basis. Such variability may be expressed as a proposed range, a proposed likelihood distribution or a proposed value with confidence measure, for example. The specific dose to apply to a voxel may be selected from the dose range according to a third set of rules. For example, for a given plan class, the inferred voxel-by-voxel dose may be set to the median value for the distribution of inferred values and for another plan class the inferred voxel-by-voxel dose may be set to the maximum value for the distribution of inferred values, corresponding to the requirements of the particular treatment plan class.

The proposed dose map may provide a voxel-by-voxel mapping of proposed dose distribution over the image data. The voxel resolution of the proposed dose map may or may not correspond to the resolution of the image data. For example, a 256×256 proposed dose map may be generated for a 512×512 image, or vice versa.

In some examples, the proposed dose map may be outputted (e.g., displayed on a display device, such as a computer screen) for visualization by the user. This may be, for example, a voxel-by-voxel dose map superimposed on the image data. In some examples, the visualization of the proposed dose map may include visualization of a confidence measure (where the proposed dose map has variability, as discussed above) of each voxel of the proposed dose map, for example by color-coding the proposed dose map according to the confidence measure.

The outputted visualization may be provided with a user interface to enable the user to manually modify proposed dosages and/or image features, such as delineated ROI(s), used to calculate the proposed dose map. For example, the user interface may provide the user with editing tools (e.g., a paintbrush tool) to increase or decrease the proposed dose for voxel(s) of the proposed dose map and/or to add, remove and/or modify ROI(s) in the image. After any changes are made, the user may confirm the changes and the method may return to one or more of the above-mentioned steps (depending on the extent of the user's changes) to recalculate the proposed dose map.

Optionally, at 2064 and 2065, automated QA may be performed on the proposed dose map. This may be carried out using the automated QA method described above, for example. If the QA fails (e.g., the confidence level is below an acceptable threshold) the user may be prompted to manually change the proposed dose map (e.g., using the visualization and user interface described above) at 2066.

At 2067 and 2068, the proposed dose map may be used to generate treatment parameters for a proposed treatment plan, in accordance with a second set of one or more rules. The second set of rules may optionally include optimization algorithms for optimizing beam fluence 2067, for example. The second set of rules may include, among others, one or more of:

historical treatment parameters for a given planned dosage (e.g., three beams are used to reach given dose in dense tissue);

historical treatment parameters for a given treatment plan class (e.g., breast treatments always involve three beams);

a mathematical function (e.g., a regression algorithm or function relating beam angle to image features); and a general rule governing treatment parameters irrespective of the proposed dose map (e.g., defining the number of beams, the beam orientations, the beam intensities, the beam shapes, and the modulation complexity of the beams as specified by the resolution of the beam fluence generated via optimization algorithms).

Optionally, at 2069, a quality estimate (or confidence level) for the proposed treatment plan may be calculated. The quality estimate may be calculated as a confidence value, a simple pass/fail determination, or any other suitable estimate of quality. That calculation may result directly from the dose map inference process and/or the treatment plan generated following a suitable optimization method which defines the beams and/or beam shapes and/or beam intensities and/or beam modulation. The calculation may also include determination of how well certain plan features match with expected plan characteristics and may include generation of error and/or warnings if the quality estimate is below a certain threshold value. If QA fails (e.g., the confidence level is below an acceptable threshold), the user may be prompted to manually change the proposed treatment plan at 2070, to change the input data, to change the proposed dose map and/or to change optimization parameters.

At 2071, the expected dose distribution for the proposed treatment plan is calculated. Verification may be performed at this point. Verification may include, for example, checking whether the expected dose distribution matches with the proposed dose map, checking whether the expected dose distribution falls within acceptable dose guidelines, and/or checking whether the expected dose distribution is similar to historical dose distributions.

At 2072, if verification fails, the proposed dose map may be changed at 2073 (e.g., manually or automatically, such as using an iterative method), and the method returns to 2068 without generating the proposed dose map.

At 2072, if verification fails, the user may be prompted to manually change the input data at 2073 (e.g., input a different treatment plan class, add or remove ROIs, etc.), and the method returns to 2054 to generate the proposed dose map.

At 2074, if verification fails because the calculated expected dose distribution does not match the proposed dose map, the proposed treatment parameters may be changed and/or the beam optimization may be recalculated using different optimization parameters, and the method returns to 2068.

At 2078, if verification is successful, then the method proceeds to 2080.

Optionally at 2072, 2074 and 2078, a quality estimate (or confidence level) for the calculated expected dose distribution may be calculated using the example automated QA method described above. The quality estimate may be calculated as a confidence value, a simple pass/fail determination, or any other suitable estimate of quality. That calculation may result directly from the dose map inference process and/or the treatment plan optimization process and/or the treatment plan generation process, and may follow a suitable optimization method which defines the beams and/or beam shapes and/or beam intensities and/or beam modulation. The calculation may also include determination of how well certain features of the proposed treatment plan match with expected plan characteristics (e.g., based on historical data for the treatment plan class) and may include generation of error and/or warnings if the quality estimate is below a certain threshold value. If QA fails (e.g., the confidence level is below an acceptable threshold), the user may be prompted to manually change the calculated expected dose distribution at 2070 and/or 2073, to change the input data, to change the proposed dose map and/or to change optimization parameters, for example.

At 2080, the proposed treatment plan is outputted (e.g., presented to a user visually on a screen). The output may be provided via a web portal. For example, a user may access the example system through a separate client device (e.g., a mobile computing device, such as a tablet or a smartphone) via a web-accessible portable provided by the system. This may enable greater mobility and flexibility for user interaction with the system. The proposed treatment plan may also be transmitted to a database for future consideration and/or may be added to the historical data.

Optionally, output indicating the calculated quality estimate may also be provided. For example, a report may be generated and displayed to the user on a display device (e.g., display screen of any suitable computing device) and/or may be printed. The report may be stored for further processing and/or future reference in an internal or external memory of the system, for example.

The output may include any output of the automated QA system, and/or an estimate of confidence at each voxel of the dose map indicating where there is uncertainty or ambiguity as to whether or not to irradiate a patient at that location.

Thus, the example method generating the proposed treatment plan may also enable estimation of the quality of a proposed treatment plan based on an integrated consideration of plan features optionally together with ROI features, patient features, and other considerations (e.g., treatment requirements), for example.

In some examples, the disclosed methods and systems may use machine learning to build an automated planning method for treatment planning. Imaging and treatment planning data may be grouped according to treatment site and treatment technique. Relevant features (e.g., as shown in FIG. 21) for inferring the dose map may include, for example, image texture [38], image intensity, image position, position inside patient [39] and position inside ROI.

Features may be extracted from historical training data, and used to construct the learning algorithms and train the treatment planning model. Additional features, not found directly in the RT images and/or ROIs, may be automatically generated by applying segmentation algorithms, which can delineate relevant organs in the RT image dataset.

Automated inference of the proposed dose map may include the following steps: 1) image segmentation; 2) feature calculation; 3) plan generation 4) quality estimation; and 5) review. Retrospective plans that were classified as clinically unacceptable may be used to assess the ability of the algorithm to generate plans for patients who previously failed the standard treatment planning clinical practice.

In some examples, the automated dose mapping process may be integrated with existing clinical treatment planning functionality by providing an estimate of the plan that can be refined, or used as a starting point for the standard clinical practice.

The inputs into the example of FIG. 20b have been simplified for illustrative purposes and may include: existing treatment planning data, imaging data and regions of interests (if delineated, either manually, semi-automatically or completely automatically). Other sources of data not represented in the figure may include previous outcomes data, including treatment related toxicity, survival data and recurrence data; data related to treatment delivery such as specifications of the treatment delivery unit; or any other data pertinent to patient treatment. Any patient information useful for a physician to make an accurate decision about the treatment plan may be included, and that information may be considered jointly as opposed to independently [23].

In the example shown, the automated treatment planning process may include various interconnected sub-components, which may be similar to the components described above for the automated QA process, including:

Manual, semi-automatic, or automatic segmentation,
ROI classification and quality estimation algorithm,
Dose map confidence and/or quality estimations algorithm,
visualization platform,
review and approval platform In the training phase, labelled ROIs and previously approved treatment plans may be used to train an algorithm for automated treatment planning. The automated treatment planning algorithm may be trained on a database of example plans with or without known labelled ROI (e.g., heart, lung, etc.).

Automated treatment planning of a clinical RT treatment plan is now discussed. Once the plan is generated the next phase might be further refinement or review either manually or in an automatic setting (as in the next section). The basic automated treatment planning pipeline may include the following:

Images may be first acquired. CT is predominately used in RT for treatment planning although other imaging modalities can also be used instead, or in addition to augment the information for treatment planning.

From the desired imaging datasets, ROIs may be delineated manually, semi-automatically or completely automatically. This task may be done by the radiation oncologist or the treatment planner, for example. The automated segmentation may generate ROIs automatically using standard segmentation algorithms and the features from these ROIs may be extracted using the methods of the ROI classification algorithm. For example, the external outline of the patient may always be segmented in addition to the lungs (e.g., in thorax images), the pelvis (e.g., in abdominal images) and the skull (e.g., in head images).

The patient data is then processed into features which may, but are not limited to, image-based features, ROI features, patient history, and other biomarkers.

In some examples, the algorithm takes as input one or more images having elements which might include a single pixel at the fine-grain to groups of pixels at the coarser grain. Based on features of the image, elements, patient history, treatment intent, etc., or any combination thereof, the algorithm then establishes a correspondence (or matching) between elements in the input and elements in the database. The correspondence, or mapping, can be obtained implicitly (e.g., using machine learning algorithms such as regression) or explicitly (e.g., using image registration [40]). The correspondence can be between elements in a pair of patients (one patient to be planned, one historical patient), or to many patients (one or many patients to be planned, to one or many historical patients). In the case of adaptive planning, the historical data can also include the patient's own previous treatments. The dose can then be calculated from the known dose to corresponding elements in the database, e.g. via averaging over the dose of the most similar elements.

Approaching the problem as one of establishing correspondence or similarity in this manner allows for the interchangeability of registration, regression, and classification algorithms. The correspondence may be regularized spatially, as in the example of deformable image registration, to ensure a relatively consistent dose map is defined for neighboring image elements, e.g. the dose to be applied nearby voxels is relatively similar, or, for example, via a conditional random field (e.g., as used in the Conditional Random Forest algorithm eq. (2) and eq. (11), replacing F with features from Table 9 (FIG. 21) and c with dose-per-element).

The extracted features are then input into the learned dose prediction algorithm, which outputs a dose estimate for each voxel in the input image. The dose estimate might be, for example, a maximum-posterior estimate taken over a learned probability distribution of dose given features, or the output of a regression method [41,42] or estimated via atlas-based registration replacing the canonical atlas-segmentation with an atlas-dose map [43-45].

The dose estimate may include a probability distribution over all dose values that estimates the probability of a particular dose at that voxel given the observed features, or another form of confidence measure in the predicted output, such as a confidence interval.

The generated treatment plan may be then subject to technical and clinical review as part of the RT process using standard approaches or using the automated QA method described above.

In addition to providing an overall dose map and confidence and/or probability estimate, the example method may provide estimates of what caused uncertainty in the dose distribution. For example, in the case of extreme image noise the dose map will have a high degree of uncertainty and the corresponding image features will be reported.

The generated dose map may be incorporated into the treatment planning process in various ways such as:

The method and system may be used to augment the current clinical process and provide the RT team with a reference plan.

The dose map may be run through existing treatment planning systems to generate a full plan for clinical treatment.

Optionally, the system may be used to automatically adapt (e.g., using a deformable register) the patient's planned treatment to a treatment day image, or subsequent treatment day by including the planned treatment (or previous treatments) in the learning database with or without the previous plans from other patients.

The system of FIG. 2 may be used to implement the automated treatment planning system, and may include: 1) The automated dose map prediction algorithm described above; and 2) the visualization and review platform which may provide a user with the ability to interrogate the dose map. The user may be able to edit the dose map manually, such as through the addition of plan information such as adding ROIs, or automatically. The dose inference or treatment optimization may then be updated to generate an updated calculated dose map.

Example Algorithms

Various examples of the disclosed methods and systems may be implemented using one or more of the example algorithms discussed below. The algorithms may be customized depending upon the specific application, i.e. automated QA or automated treatment planning. The algorithms for automated QA may also be applied for automated treatment planning, for example using the ROI classification algorithm to classify ROIs to be used for feature calculation as input to the treatment planning algorithm. These are provided for the purpose of illustration only and are not intended to be limiting. The present disclosure is not bound by any theory or model discussed herein.

An example approach to perform the ROI and plan classification may be to treat them as separate classification algorithms, and rely on a third algorithm to integrate the results. In principle, all three algorithms could be the same exemplar classification algorithm (e.g. Support Vector Machines, Random Forest, K-means, etc.) [42,46], or each algorithm can be a customized classifier designed specifically for the problem at hand [47]. Customized classifiers may yield better performance (see example results comparing classification of ROI in Table 6, Table 7 (FIGS. 14a-14c and 15a-15c); and treatment plan in Table 5 (FIG. 13a-13c)). One such example is the ROI classification algorithm implemented in [47]. The ROI classification algorithm may be customized for ROIs by including groupwise features calculated between the different ROIs in a plan, and ensuring that the assignment of class labels across all ROIs in the plan is consistent.

Similarly, for automated treatment planning, a canonical regression algorithm [41,42,46] can be used, or a customized technique can be developed following that of the ROI classification algorithm [47].

For automated QA, the classifiers can be considered as blackboxes as in FIG. 1, blocks A and C. Each classifier may take as input a set of features, F, and may output a class label Y. Each classification algorithm may be augmented to further include a quality estimate, Q(F). For the case of ROIs, the quality estimate may be an estimate of each ROI's quality. For plans, the quality estimate may be an estimate of the overall plan quality. The quality estimate may be generically referred to as a function Q(F), where the features, F, can even include the class label itself. Quality estimates can be made through density estimates [47] which may be the probability of observing a given set of ROI features together with a specified ROI label, or the probability of observing a given set of geometrical patient features, in conjunction with particular beam geometry or dose distribution. This may capture, for example, the relationship that patients with large hearts typically have a different beam configuration than patients with small hearts. If a small heart patient is assigned the beam configuration of a large heart patient, the example system may return a very low likelihood of that being correct. The ability of the example system to jointly consider patient and plan information may be in contrast to conventional algorithms that considered only plan information [23].

For automated treatment planning, the regression algorithm, as well as the optional ROI classification algorithm, may also be considered black boxes in a similar fashion to automated QA. The algorithms are similar, where the automated treatment planning learns and makes use of, for example, the probability of observing a given dose at a given image (e.g. CT, MRI, etc.) patch using learned descriptors of the patch, in addition but not limited to optional ROI and patient history features for a particular RT class. Modelling, for example, that in radical breast RT patches with a heart-like appearance, or heart-based ROI features, are to be given no dose.

Different examples of the disclosure methods and systems can include different classifiers and/or regression algorithms, and different density estimation methods, or classifiers with built in estimates of quality and/or density, or avoid classification and perform density estimation directly on available features. Again, plan quality may be judged automatically by jointly examining plan and patient features, including ROI features if available. Similarly, automated planning by jointly examining patient features from the images and/or other sources, e.g. ROIs, patient history, treatment intent, etc. Instead of learning densities, distance metrics [49] between patients and distance metrics between plans may be learned or used, thereby matching a new patient to the most similar patient in the patient database. For automated QA, the plan for the new patient can then be compared to the plans of the most similar patients using calculated features and/or a learned distance. For automated treatment planning, the plan for the new patient can be copied from the existing similar patient, or fused from many similar patients, using one of the regression and/or registration algorithms. A density can be directly assigned (e.g. Gaussian with mean zero and standard deviation 1) or learned from the training data. These learned distances may be considered features, which can be used in the disclosed methods and systems just like any other feature discussed herein.

It is important to note that while the scale of the features, and items, processed can impact algorithm accuracy, it is variable and in no way limiting of the proposed systems. Automated QA or treatment planning can involve features and algorithms from the fine level (e.g. features per-pixel) to the moderately coarse (e.g. feature per image-patch or per-ROI) to the coarse (e.g. features per patient). For example, in automated treatment planning this could mean learning to predict dose for a particular image patch, or simply copying and/or registering the dose map from the most similar patient in the database (a nearest-neighbour method).

Classification may be relevant for applications to data mining, and when the plan class itself is used as a distinguishing feature for accurate quality estimation (for example, when identical patient features can correspond to two different treatment techniques).

Relationships that are known a priori (i.e., that do not require learning) may also be used. For example, examples of the disclosed methods and systems may include manually encoded (hard-coded) rules, such as to check that patients under the age of 25 do not receive more than a particular dose amount. Such manual encodings may be included in the quantitative feature analysis box (block H).

In some examples, classifiers and/or density estimation techniques may be replaced with regression algorithms. Regression algorithms may be related to classifiers, but they typically seek to predict a continuous output as opposed to a discrete class label. For example, a regression approach may attempt to learn Q(F) directly from the example quality estimates given for the training data. Similarly for automated treatment planning, the regression may be replaced with classification predicting dose or no dose, instead of a continuous dose value. These methods may require known estimates of plan quality, whereas density estimation methods may assume plan quality is proportional to how often a combination of plan and patient features are observed together.

Automated treatment planning can also be augmented by the methods and features used for automated QA. Automated QA, as disclosed herein, may enable planners to generate a plan, and then query the system to see if it meets clinical standards in a real-time fashion, and that feedback can be used to tweak the plan. If the planner is missing a beam, for example, the example system may report this to the user and the planner can then add another beam. Similarly, by learning a joint distribution over plan features and patient features, known variables may be integrated by the example system to provide the planner with the most likely values for unknown variables. For example, if the plan class, ROI labels, and number of beams are all known, the example system may calculate the most likely layout of beams. This may be thought of as the example system determining the typical beam configuration for a given kind of patient (e.g., defined by that patient's features in the system, such as organ geometry, etc.). The most likely beam configuration can then be used to assist the automated treatment planning algorithm with inferring the dose map.

Without loss of generality, some example embodiments of each main algorithm are discussed below. For brevity, only classifier-based embodiments are discussed for automated QA, as extension to regression-based methods is expected to be straightforward. Only regression-based examples are discussed for automated treatment planning. Each subsequent section is kept brief where details of the algorithm are not the focus of this disclosure.

Example ROI Classifier Algorithm

An example of the ROI classifier is described as follows. At a high level the example classier may use shape and density features calculated individually for each ROI as well as features between different ROIs to estimate the classes of a new set of ROIs.

Each RT plan considered may include one or more ROIs, and a corresponding CT image. In practice there may be no set number of maximum ROIs that might appear in a plan. For example, a plan might contain a heart ROI and two lung ROIs, a heart ROI with no lung ROIs, or an anal canal ROI with a rectum ROI. Which ROIs can and cannot appear together fluctuates across different cancer treatment centres, and so this relationship may need to be learned instead of set manually. CT images are typically used almost universally for treatment planning as they may provide a direct way to estimate the density of a given voxel, and therefore how much radiation dose will be delivered to a particular ROI. However, the present disclosure may be implemented with other modalities (e.g. MRI, cone-beam, etc.). An example of a suitable classifier algorithm is presented in [48], and briefly discussed below.

The individual features of ROIs may be first outlined, and a Random Forest (RF) classifier may work from just those features. Inference may then be performed using a learned prior distribution over which ROI classes can appear in a group together, thus building a Groupwise Random Forest (GRF) classifier. The RF may then be conditioned on features calculated between ROIs, or, groupwise features, thus building a Groupwise Conditional Random Forest (GCRF) classifier. The quality of a given group of ROIs may then be estimated.

Example Region of Interest Features

A notation for describing ROI features is first discussed. Each ROI may be loaded from a DICOM RT plan file as a set of 3-dimensional points along the ROI's surface, denoted by $\psi$ with $|\psi|$ points. There may be a corresponding DICOM CT image volume, I(x) where x∈Ω, the image domain, with |Ω| voxels. S(x) may be defined as a binary representation of the ROI, with 1 for object and 0 for background, and a corresponding signed distance function (SDF) representation $\varphi$(x), with positive values inside the object and negative outside [50].

Individual ROI features may be calculated for a single ROI, as opposed to a group of ROIs. They can be grouped into two broad categories: shape and intensity.

Shape features may involve both affine invariant and affine dependant features, and it may be left to the learning stage to automatically determine if affine dependant features are reliable for a given ROI class. Various treatment protocols may demand that a patient be scanned in a consistent pose, and thus affine dependant features may be useful for those resulting ROIs. Examples of ROIs features are summarized in Table 1, FIGS. 3a-3b. Vector valued features, e.g. histograms, may be concatenated with scalar features to create a single final feature vector per ROI. Though seemingly simplistic, ROIs of different classes may have the exact same shape, and so no set of shape features may be sufficient to distinguish between them. For these ROIs density information may be first used, and then groupwise information.

Intensity features may capture information about the density distribution for a given ROI, such as listed in FIG. 3b. They may enable distinguishing between two equally shaped objects that have different densities within their boundaries, such as an esophagus and spinal canal in CT, for example.

The task of classifying a single ROI given its individual features using RF is discussed below.

Random Forests for Region of Interest Classification

FIGS. 4a-4d show progressively descriptive example graph structures for automatic ROI classification. Dashed lines in (d) are used to indicate that only select features within the plates are linked to the class label variables, $c_{*,j}$. Connections between all feature, class label variable pairs are not shown to keep the graph more easily interpretable.

First introduced by Leo Breiman in 2001, RF are a generalization of decision trees that use a mode-based voting algorithm over a set or forest of decision trees [42]. A new sample may be classified by each decision tree, and then the mode of the output over the entire forest may be taken as the final output class. A detailed review of RFs is outside the scope of this disclosure, and a discussion may be found in [51]. The following summarizes the RF approach in its application to ROI classification and describes some details to assist in understanding the present disclosure.

Let $P_j$ be an individual RT plan from a set of plans P. Each plan contains one or more ROIs, denoted as $\{C_{1,j} \ldots C_{k_j,j}\}$ for plan $P_j$ with $k_j \in [1,\infty)$ROIs. Each ROI may take one of |C| class labels where $c_{i,j} \in C$ is the class label for ROI $C_{i,j}$, and C is the set of possible class labels (e.g. heart, breast, lung). A set of features, F, may be defined with N features per ROI. An individual feature $\{F_{h,i,j}:h \leq N\}$ may be calculated from plan $P_j$, and ROI $C_{1,j}$. Rather than always writing 1 . . . n for some set with n elements, * has been used to denote taking the entire set over a particular index, or group of indices. Therefore, $F_{*,1,1}$ is the same as $\{F_{1,1,1} \ldots F_{N,1,1}\}$. Indices have also been replaced by ROI names to indicate all ROIs of that class, as a list of ROIs for a given plan is unsorted. For example, $F_{*,heart,*}$ is the set of all features for all heart ROIs taken across all plans. Lastly, the relative complement of a set has been denoted by \. For example, $F_{*\backslash h,1,1}$ is equivalent to $\{F_{1,1,1} \ldots F_{h-1,1,1}, F_{h+1,1,1} \ldots F_{N,1,1}\}$. For ease of reference the notation used herein is summarized in Table 2, FIG. 5.

Given a set of features, $F_{*,i,j}$, the goal is to predict the class label $c_{i,j}$. Casting this as an inference problem, the goal is to learn $P(c_{i,j}|F_{*,i,j})$, denoting the probability of ROI $C_{i,j}$ being assigned class label $c_{i,j}$, given the jointly observed features $F_{*,i,j}$. Inference may be performed to obtain the class label using a maximum-a-posteriori (MAP) estimate as:

$$c^*_{i,j} = \operatorname{argmax}_{c_{i,j}} P(c_{i,j}|F_{*,i,j}) \qquad (1)$$

Various methods may be suitable to potentially learn $P(c_{i,j}|F_{*,i,j})$; in this example, RFs are used because the inference and learning are typically both reasonably fast [51]

RF Learning $P(c_{i,j}|F_{*,i,j})$ may be estimated from M training plans, $P_1 \ldots M$, with known ROI class labels $c_{*,1 \ldots M}$ and corresponding features $F_{*,*,1 \ldots M}$. The training may be a bootstrapping method using cross-validation to build a strong learner, the forest, from a combination of weaker learners, the decision trees [42]. Assume the training set consists of R ROIs, and that the forest will constitute a set of trees, T.

To build a particular tree, $T_t$, a subset of ROIs, r, may be chosen at random with replacement from the set of R training ROIs. This subset of ROIs may form the training set of an individual tree, and the test set for each decision tree may be all the ROIs not in the tree's individual training set (which may be referred to as the tree's out-of-bag samples). Out-of-bag samples effectively may give the RF method a built-in form of cross-validation, where each tree is trained on some of the set of R ROIs and tested on the remainder. For each node in the tree, a subset of ROI features, $F_{1 \ldots n,r,1 \ldots M}$, where n<<N, may be randomly chosen. Features $F_{1 \ldots n,r,1 \ldots M}$ may be used to make a classification decision at that node by calculating the best split based on Shanon entropy [51].

Every branch node now may represent a binary split over a particular subset of features. Given a particular feature sample, $f = F_{*,i,j}$, the tree can be traversed down to a leaf node. During training, for every class label, the number of training samples that reach the leaf node may be counted and used to estimate $P_t(c_{i,j}|F_{*,i,j}=f)$. This may be repeated for all leaf nodes, creating an empirical estimate of $P(c_{i,j}|F_{*,i,j})$, taken as the mode of $P_t(c_{i,j}|F_{*,i,j})$ overall trees in T.

RF Inference

Given a novel ROI, $C_{i,j}$, features, $f = F_{*,i,j}$ may be computed, and then every tree in the forest may be traversed and $P(c_{i,j}|F_{*,i,j}=f)$ may be computed as the mode across the forest. The assigned class label for $C_{i,j}$ maybe then calculated according to (1).

An observation is that (1) only considers a single ROI, whereas each plan can contain a group of ROIs. The graph structure thus far is depicted in FIGS. 4a and 4b. The joint probability may be estimated for an ROI and its observed features (FIG. 4a), but all new ROIs in a plan may be considered to be independent (FIG. 4b). In essence, though $P(c_{1,j}|F_{*,i,j})$ has been modelled thus far, the goal is to model $P(c_{*,j}|F_{*,*,j})$. The next two sections discuss how to approximate this model and perform inference.

Groupwise Random Forests

Though RFs are an increasingly popular learning algorithm, in their default incarnation they typically classify all input data independently [51]. In the context of the present disclosure, this may mean when encountering a group of ROIs the resulting classifications may make no attempt to ensure consistency across the ROI labels. For example, an anal canal ROI is unlikely to appear in the same plan as a breast ROI, and this relationship should be accounted for during learning and inference. At this point the set of output labels $c_{*,j}$ is of concern, and not the specific distribution $P(c_{*,j}|F_{*,*,j})$, thus it may be sufficient to ensure the distribution is considered in the inference, even if not directly calculated. The model becomes a CRF [52]. Note, however, that this is not what is referred to the conditional RF, as will become clear in the next section.

Figure 4C:
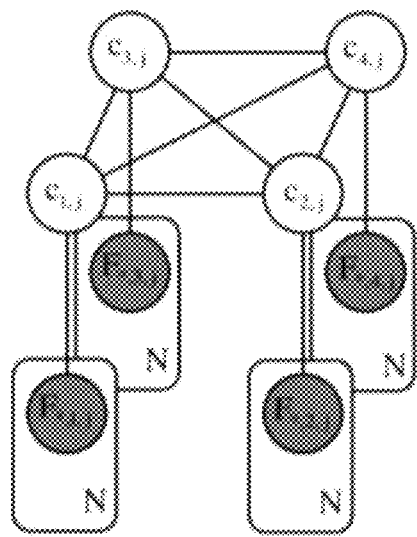

At this stage the CRF models the connections between unobserved ROI class labels, $c_{*,j}$. Rather than enforcing a particular degree of connectivity amongst the different classes, it has been learned which class labels are independent, and thus the graph topology. An example of the fully connected class labels, with corresponding conditional features, is shown in FIG. 4c. Consider the complete distribution in terms of potential functions, $\psi$, defined over the maximal cliques in the graph. Further below is a discussion of how to learn those potentials.

The groupwise potential function may take the form:

$$P(c_{*,j}, F_{*,*,j}) = \frac{1}{Z}\psi(c_{*,j})\prod_{i=1}^{k_j}\psi_i(c_{i,j}, F_{*,i,j}), \quad (2)$$

where Z is the partition function. $\psi_j(c_{i,j}, F_{*,i,j}) = P(c_{i,j}|F_{*,i,j})$, learned from the RF model, may be set. Application of the product rule is expected to lead to a conditional density of:

$$P(c_{*,j}|F_{*,*,j}) = \frac{1}{Z \times P(F_{*,*,j})}\psi(c_{*,j})\prod_{i=1}^{k_j}P(c_{i,j}|F_{*,i,j}). \quad (3)$$

The result is expected to be an inference problem of the form:

$$c^*_{*,j} = \operatorname{argmax}_{c_{*,j}} \psi(c_{*,j})\prod_{i=1}^{k_j}P(c_{i,j}|F_{*,i,j}), \quad (4)$$

where $\frac{1}{Z \times P(F_{*,i,j})}$ has been removed because it may be expected to have no effect on the maximization over $c_{*,j}$. Finally, taking the negative logarithm of the likelihood is expected to yield the minimization problem:

$$c^*_{*,j} = \operatorname{argmin}_{c_{*,j}}\left(-\log(\psi(c_{*,j})) - \sum_{i=1}^{k_j}\log(P(c_{i,j}|F_{*,i,j}))\right). \quad (5)$$

GRF Learning

In order to perform inference on (5), the class label potential function: $\psi(c_{*,j})$ should be learned. An aim may be to learn a binary potential function where $\psi(c_{*,j})=1$ for all valid class label assignment groupings, and zero otherwise. This may be a design choice to ensure that rare groupwise label configurations are not discounted simply because only a few patients need that particular set of ROIs for treatment. Essentially, this prior may describe all feasible group label configurations as equally probable, while all other group label configurations are infeasible. This choice may have the added benefit of reducing inference difficulty, as discussed shortly. In practise a less restrictive prior could be learned from class label histograms but this may increase inference difficulty and impose an undesired prior. Using the M training plans, $P_{1 \ldots M}$ discussed above, the set of all unique class label assignments groupings, G, may be learned, where $G_p$ denotes particular grouping. The groupwise class label potential function, $\psi(c_{*,j})$, may not in general be submodular. Exact optimization of (5) may be expected therefore to be NP-hard [53].

GRF Approximate Inference

The inference algorithm may be based on the popular graph cuts technique [54,55], but inference may be formulated as a generalized assignment problem. For the moment, the class label interaction potential function $\psi(c_{*,j})$ may be ignored. The cost of assigning a label to a ROI may be set as $-\log(P(c_{i,j}|F_{*,i,j}))$. The best assignment is expected to have minimal cost (although other optimization techniques may be possible, for example the best assignment may be expected to have maximal cost in some cases), while ensuring that each class only appears a set number of times. The problem can be expressed as the following linear program:

$$x^* = \operatorname{argmin}_x -\sum_{u \in C}\sum_{i=1}^{k_j} x_{u,i}\log(P(c_{i,j}=u|F_{*,i,j})) \quad (6)$$

subject to the constraints:

$$\sum_i x_{u,i} \leq 1 \text{ for } u \in C \quad (7)$$

$$\sum_{u \in C} x_{u,i} = 1 \text{ for } i \leq k_j$$

$$x_{u,i} \geq 0 \text{ for } u; i \in C; k_j.$$

The variable, $x_{u,i}$, may be a binary indicator variable that assigns ROI class label $u \in C$ to ROI $c_{i,j}$. As written this may be considered to be a standard assignment problem [56]. The first constraint may ensure that at most one instance of a given ROI label occurs in a single plan. The second constraint, in combination with the third constraint, may ensure that a single ROI is assigned only one label. Since the constraint matrix may be totally unimodular there may always be at least one integral valued solution, thus there may always be an optimal solution where x will be binary (i.e. assigning each ROI a single label instead of a fraction of labels). Since the program is linear, any optima may be expected to lie at the bounds of constraint space and those bounds are integral. This may be relevant because enforcing $x \in \{0,1\}$ may create a harder optimization problem [56].

An approximation to $\psi(c_{*,j})$ may be made by modifying the constraints of (6) to:

$$\sum_i^{k_j} x_{u,i} \leq L_u \text{ for } u \in C \quad (8)$$

$$\sum_{u \in C} x_{u,i} = 1 \text{ for } i \leq k_j$$

$$x_{u,i} \geq 0 \text{ for } u; i \in C; k_j.$$

This modification may ensure that at most $L_u$ instances of a given ROI class occur in a single plan. For example, a plan can only have one heart ROI, but can have multiple targets. $L_u$ can be readily computed by taking the maximum number of times a given ROI appears in the training set. This may be also a design choice, and in practise $L_u$ could be set to $\infty$ if no constraint is desired. Note, however, that this modification may partially model $\psi(c_{*,j})$ as it allows a heart and a lung, but not two hearts, for example. In essence this may model the groupwise potential function between all instances of the same class label. The groupwise potential between different classes is considered.

$\psi(c_{*,j})$ may be introduced by creating a quadratic program over the binary indicator variables, but the result may be a non-convex quadratic whenever $\psi(c_{*,j})$ is not submodular. The non-convexity may stem from trying to restrict groupings with non-empty intersects, such as trying to enforce an XOR relationship like {lung, heart, breast} and {lung, heart, esophagus}, but not {lung, heart, breast, esophagus}. Suppose, however, that it is known that a particular set of ROIs $c_{*,j}$ contained labels from $G_p$. The following unimodular constraint may be added to (6):

$$\sum_{u \notin G_p} x_{u;i} = 0 \text{ for } i \le k_j; \qquad (9)$$

which may ensure that the assigned class labels will be in $G_p$. This may lead to a natural, though approximate, inference algorithm for (5).

First, the most likely grouping may be determined as:

$$G_p^* = \operatorname{argmax}_{G_p} \sum_{u \in G_p} \sum_{i=1}^{k_j} \log(P(c_{i,j} = u \mid F_{*,i,j}),) \qquad (10)$$

which may be the expected group given the observed features. Then (6) may be optimized with added constraints (8) and (9).

GRF Exact Inference

Though exact inference of (5) may be expected to be NP-hard, taking advantage of the linear relaxation in combination with the problem structure can provide reasonable run times. Notice that $-\log(\psi(c_{*,j}))$ in (5) may be zero for any viable group configuration, and $\infty$ for all others. Any grouping outside of G may have infinite cost, and so only class label groupings in G may be optima. Provided there are a small number of feasible groups, one may need only optimize (6) with added constraints (8) and (9) for each group $G_p \in G$. The result may be a x* for every group $G_p \in G$, and the one with the minimal objective value according to (6) may be the global optima of (5). In practise there could be an exponential number of groups in G, and so no theoretical bound on running time may be broken.

Building from the previous section, the example model may now consider joint-wise potentials over class labels enabling a groupwise assignment of labels given the RF generated posterior distributions over features. However, consider the following example feature relationship: lungs are larger than hearts. Currently the model may have no way to learn this relationship, or to use it during inference. A challenge during inference may be that which ROI is the lung may be unknown, and therefore the feature itself may be a latent variable. The following section discusses how to calculate groupwise features, condition the RFs on these variables, and how to use the groupwise features during inference.

Groupwise Features and Groupwise Conditional Random Forests

Groupwise features may be defined as those calculated between groups of two or more ROIs. Although this example focuses on features calculated between pairs of ROIs, in practise larger groupings could be used. Examples of groupwise features are listed in Table 3, FIG. 6. These features can be calculated between pairs of ROIs, but a question may be which pairs of ROIs to calculate a feature for. So, for example, consider the distance between ROIs. When performing inference on a novel ROI the inference method may need to know if the pairwise distance is between the novel ROI and a lung or the novel ROI and an anal canal, for example. For example, a small distance to the lung ROI may indicate a possible heart label, while the anal canal may preclude the heart label. Essentially, both a groupwise feature and the class it is calculated with respect to may need to be known for inference. While being close to "some" other ROI may be a valid feature, it may not be nearly as discriminative as being close to an ROI with a known class label. In general, pairwise groupwise features can be written as $g(c_{b,j}, F_{*,a,j}, F_{*,b,j})$ for ROI $C_{a,j}$ calculated with respect to ROI $C_{b,j}$. Groupwise features may be restricted to at most one unobserved ROI label, but multiple observed ROI labels can be used. Discussion of this appear in [48].

Figure 4D:
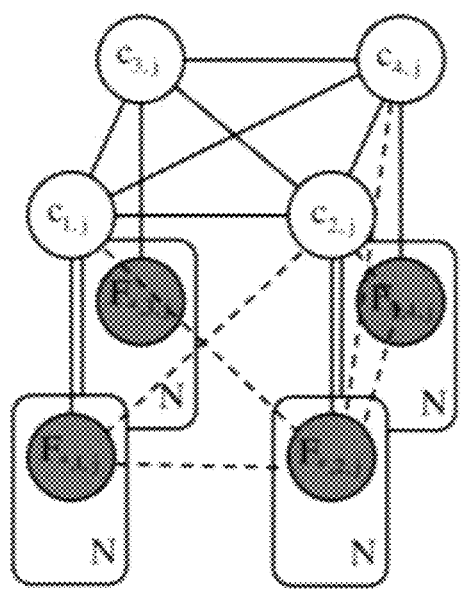
Figure 8A:
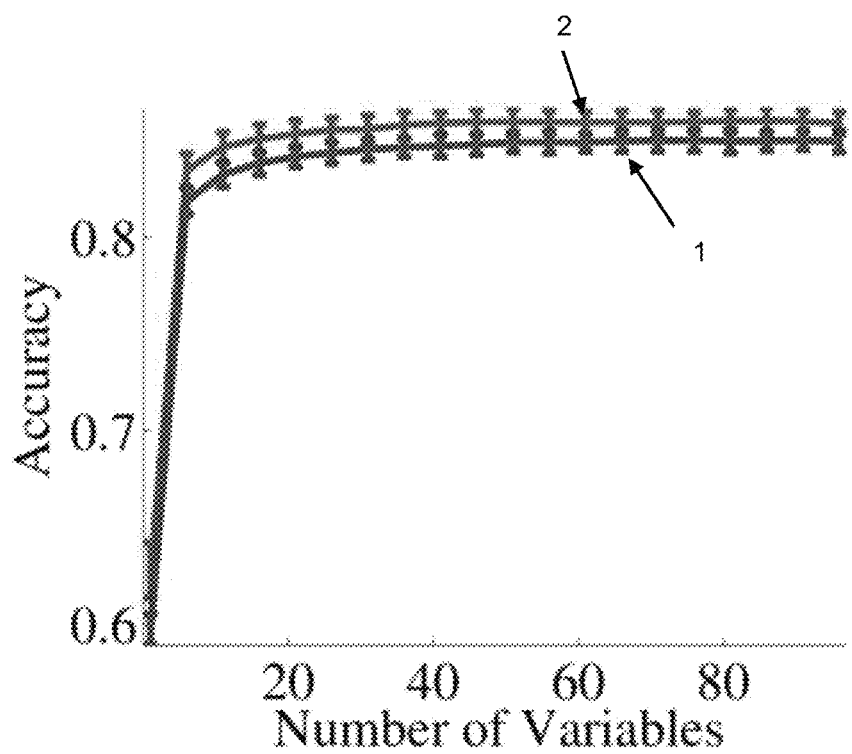
FIGS. 8a-8d are charts illustrating parameter sensitivity in example Random Forest and conditional Random Forest models.
Figure 8B:
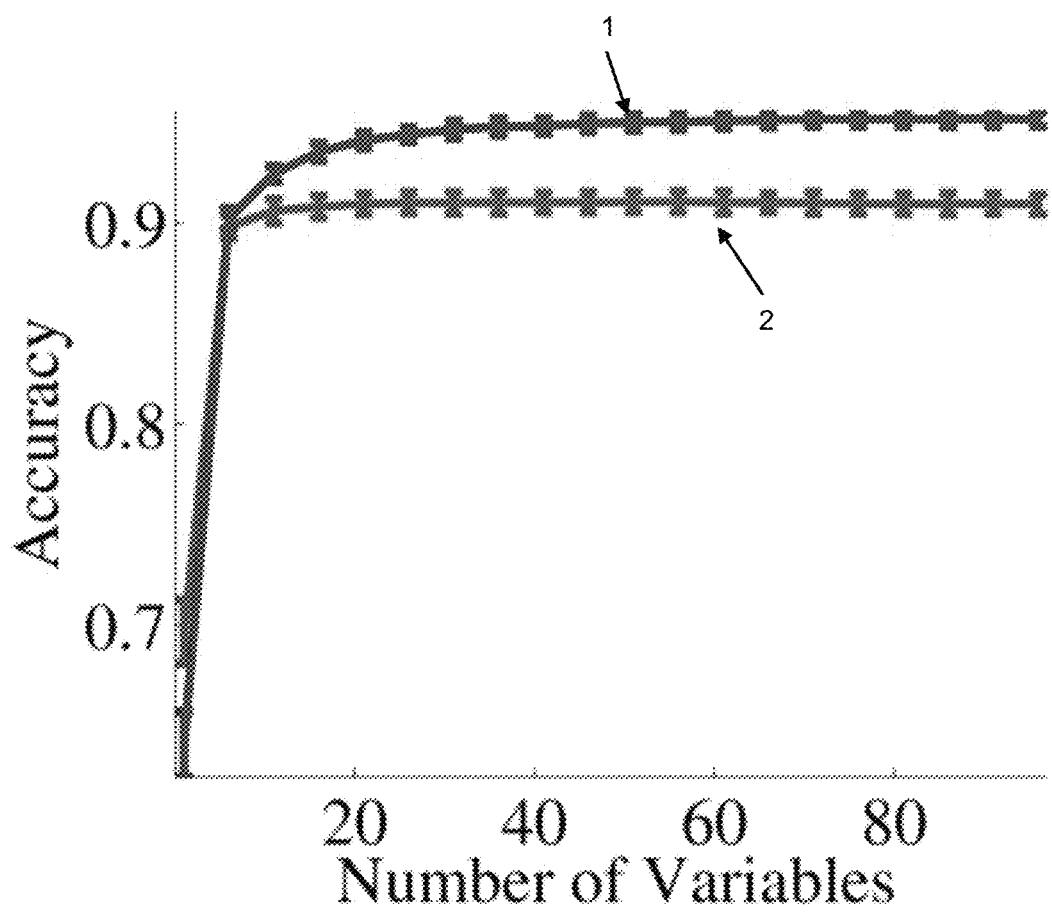
Figure 8C:
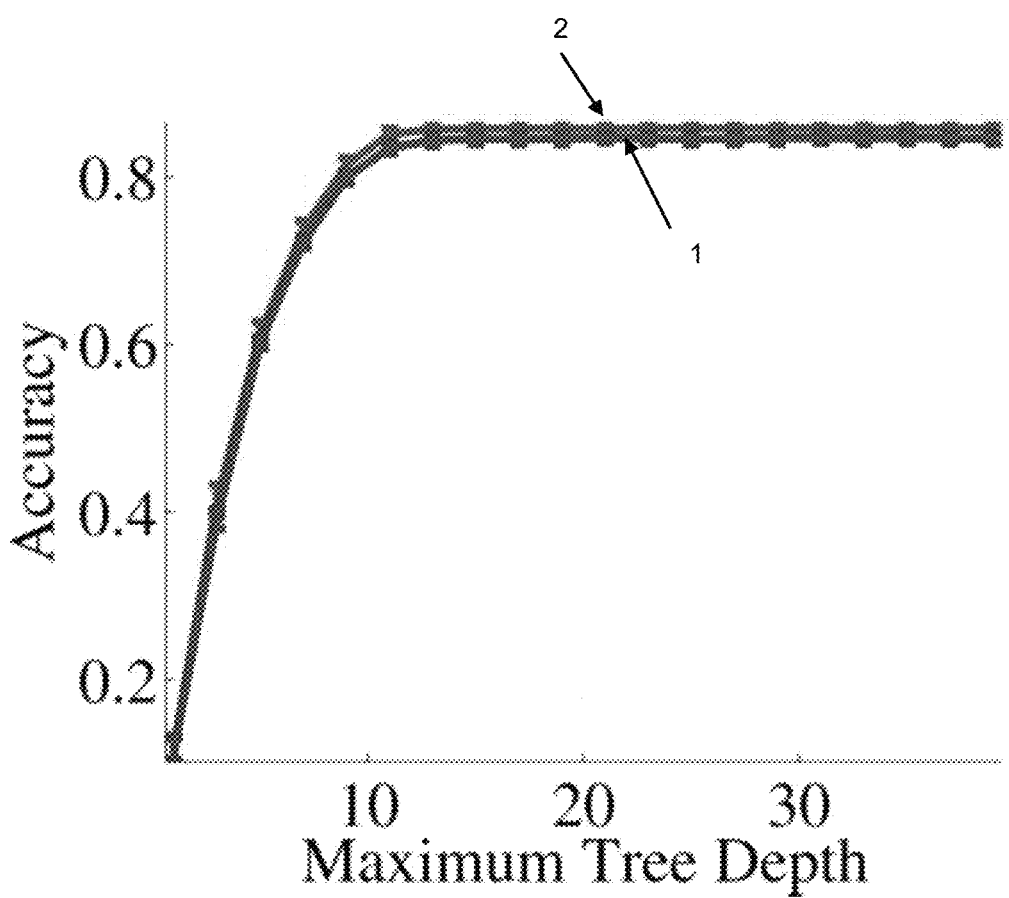
Figure 8D:
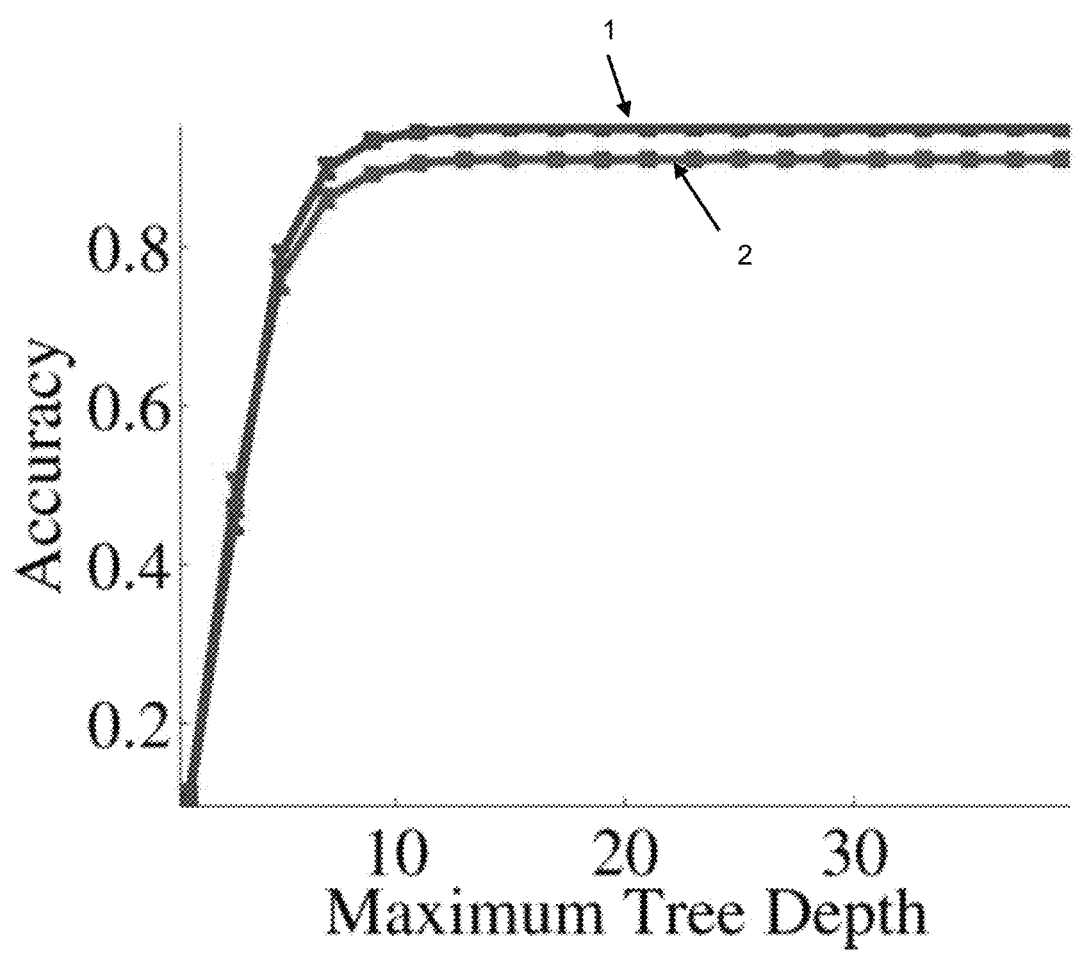

The remainder of this section discusses how to perform learning and inference on the graph in FIG. 4d, while also learning the structure of said graph (i.e. between which pairs of ROIs to build the features). As with the previous section, the complete distribution is first considered and then inference is discussed.

The groupwise potential function with groupwise features may take the form of:

$$P(c_{*,j}, F_{*,*,j}) = \frac{1}{Z} \psi(c_{*,j}) \psi(c_{*,j}, F_{*,*,j}). \qquad (11)$$

where $\psi(c_{*,j})$ is discussed above, and $\psi(c_{*,j}, F_{*,i,j})$ may be where $g(c_{*,j}, F_{*,*,j})$ is incorporated. The potential function, (11), may include the seemingly non-maximal clique $\psi(c_{*,j})$ to handle the graph pruning that may occur during learning (indicated by the missing dotted connections in FIG. 4d). Consider the conditional distribution assuming all but the ith ROI class label:

$$P(c_{i,j} \mid c_{*\setminus i,j}, F_{*,*,j}), \qquad (12)$$

where $c_{*\setminus i,j}$ denotes having observed all ROI class labels for plan $P_j$ except for the ith. This distribution can be learned by RFs, similar to how $P(c_{i,j} \mid F_{*,i,j})$ was learned in the above discussions.

GCRF Learning

During training the labels for all ROIs may be known, and thus the groupwise features can be calculated, and (12) can be learned. A challenge may be to learn which features can be reliably calculated during inference on novel data. A groupwise feature can be reliably calculated if its dependent class labels can be determined without groupwise features. For example, suppose $P(c_{1,j}=\text{lung} \mid c_2 \ldots _{k_j,j}, F_{*,*,j}) \approx P(c_{1,j}=\text{lung} \mid F_{*,1,j})$, then observing a lung ROI may be independent on all groupwise features and all other ROI labels. Thus it may be possible to infer if $c_{1,j}=\text{lung}$ with high accuracy using only $F_{*,1,j}$. How well this condition holds may be measured by checking how well (1) predicts a given class for out-of-bag samples, also known as the out-of-bag-error [42]. As this may only make use of ROIs from the training plans, $P_1 \ldots _M$, it may be effectively performing cross-validation of the RF over different random subsets of the training data. $P(c_{i,j}|c_{*\backslash i,j},F_{*,*,j}) \approx P(c_{i,j}|F_{*,i,j})$ may be assumed for all classes with out-of-bag error below a threshold. A threshold error rate of 5% may be used, for example. By learning where $P(c_{i,j}|c_{*\backslash i,j},F_{*,*,j}) \approx P(c_{i,j}|F_{*,i,j})$ the graph connectivity in FIG. 4d may be learned. The learned graph may only have groupwise feature connections for ROI classes for which $P(c_{i,j}|c_{*\backslash i,j},F_{*,*,j}) \approx P(c_{i,j}|F_{*,i,j})$ does not hold. The resulting set of ROI classes, which may be referred to as stable classes, are denoted by T. In order to learn (12) via RF the stable groupwise features may be substituted as:

$$P(c_{i,j}|c_{*\backslash i,j},F_{*,*,j}) = P(c_{i,j}|F_{*,i,j},g(c_{\tau\backslash i,j},F_{*,i,j},F_{*,\tau\backslash i,j})), \quad (13)$$

which may assume that $c_{i,j}$ is independent from all class labels not in τ, and that groupwise features involve at most one non-stable ROI. The groupwise relationship between class labels not in T may be modelled as discussed above by $\psi(c_{*,j})$. Modelling groupwise features between non-stable ROIs is not discussed in detail here, but may be carried out using suitable methods. Using the product rule, assuming all stable ROIs are observed, and substituting in (13), (11) may be approximated as:

$$P(c_{*\backslash\tau;j} \mid c_{\tau;j}; F_{*;*;j}) = \frac{1}{Z}\psi(c_{*,j})\prod_{i=1;}^{k_j}P(c_{i,j} \mid F_{*;i;j}; g(c_{\tau\backslash i;j}; F_{*;i;j}; F_{*;\tau\backslash i;j})). \quad (14)$$

GCRF Approximate Inference

An approximate inference may be based on the learned independence relationships involving the stable classes. The stable class labels may be estimated using (1), and then the groupwise features may be calculated. Inference can then be performed using approximate or exact methods, such as discussed above, but substituting in $P(c_{i,j}|F_{*,i,j},g(c_{\tau\backslash i,j},F_{*,i,j},F_{*,\tau\backslash i,j}))$ for $P(c_{i,j}|F_{*,i,j})$.

Table 4a, FIG. 7a, provides a summary comparing classification accuracy results for various example RF algorithms.

Table 4b, FIG. 7b, provides a summary comparing classification accuracy results based on a more comprehensive set of example data.

Inferring Contour Quality

Using the class posterior distributions [56], contour quality may be estimated, under the assumption that the contouring errors may be expected to represent a larger degree of feature variation than that introduced by anatomical variability. That is to say, a heart may be expected to generally look like a heart, but a mis-contoured heart may be expected to look far less like a heart than any natural heart would, and hence may be expected to have a low class posterior given its features. For example, a jagged heart ROI may be anatomically implausible and so its features may not strongly predict the heart class. $P(c_{i,j}|F_{*,i,j})$ may be used to directly estimate contour quality for the stable ROIs, since $P(c_{i,j}|c_{*\backslash i,j},F_{*,*,j}) \approx P(c_{i,j}|F_{*,i,j})$ for these classes. For the non-stable ROIs, $P(c_{i,j}|F_{*,i,j},g(c_{\tau\backslash i,j},F_{*,i,j},F_{*,\tau\backslash i,j}))$ may be used. Whether using stable or non-stable ROIs, the automatic quality estimate may be defined as s, scored between 0 and 1.

Example Plan Classification Algorithm

An example plan classifier may be built in a similar manner as the ROI classifier discussed above. Various suitable classification algorithms (e.g. Randon Forests, Support Vector Machines) may be used that do not assume independence between input variables, as opposed to other methods like Naïve Bayes. A challenge in plan classification may be that each plan can have 1 to many fractions, each fraction can have 1 to many beams, and each beam can have 1 to many control points. These relationships may need to be built into the classifier.

An example approach to deal with this may be to use dictionary learning [57-60], and histograms. Unsupervised learning methods (e.g. K-means, sparse coding, sparse auto-encoders, etc., as discussed in [46,47,57-59,61]) may be used to learn a dictionary for control points. Novel control points may be assigned to their most similar dictionary code word, and a histogram may be computed over all control points for each beam. A beam dictionary may be then learned using individual beam features along with the control point histogram for the respective beam. Similarly, a dictionary for fractions may be learned using a histogram over beams. Finally, using a histogram over fraction code words, in conjunction with other plan features, a plan classifier can be trained. In the example of a probabilistic classifier, this approach may model the probability of observing a particular plan class given a distribution of fractions, where fractions may be recognized based on fraction features and distributions of beams, and beams may be recognized based on beam features and distributions of control points. This method may recognize a plan based on its configuration of control points per beam, creating a configuration of beams per fraction, and finally a configuration of fractions. Example results for this example embodiment are discussed below.

A related approach may be to use deep learning structures like [62-65], with shared weights for all of the control points in a beam, beams in a fraction, and fractions in a plan.

A separate approach may be to consider fractions, beams and control points as independent features. A dictionary may be built for control points as discussed above. A dictionary may be then built for beams, but without including the control point histogram as an input feature. A dictionary may be also built for fractions, but without considering the beam histogram. Finally, the fraction, beam, and control point code word histograms for each plan may be used as features. In contrast to the above example, in a probabilistic classifier this example may estimate the probability of a class label given plan features in conjunction with a distribution of fractions, a distribution of beams, and a distribution of control points. This method may not model that a particular beam occurred within a particular fraction, for example.

Another example approach may be to consider individual beams, fractions, and control points independently, rather than modelling joint distributions.

Regardless of the particular embodiment, a set of plan features may be computed for each plan, and may be used to build a classifier and perform quality estimation (via density estimation, or regression, etc.) in addition to the patient features.

Patient features can be taken directly from a patient's chart (e.g. age), or from the acquired CT image and associated plan dose map. Patient features can be as rudimentary as a histogram over image intensity, or more advanced patch-based image features with dictionary learning [57-60, 66], of any other such feature. An aim may be to calculate features that may ensure similar treatment sites have similar features, and that patients with similar geometry have similar features. When those features are combined with plan and dose-map features they may ensure that the new patient is receiving treatment in-line with how similar historical patients (e.g., from an organ geometry and appearance stand-point) have been treated in the past.

Another approach may be that of OVH [33], and other approaches in the field of content-based image retrieval. Using a new patient's geometric features (e.g., organ geometry and appearance) to find similar patients in a database of historical treatments may ensure that the new patient is treated with a plan in-line with his/her most similar historical counterparts.

Example of Automated Segmentation Algorithm

Calculating patient geometry features may be made easier with labelled image data (e.g., segmentations or ROIs). Various suitable automated segmentation techniques (such as discussed in [67,68]) may be used to segment additional image structures automatically and enable the calculation of additional features relating to how much dose certain structures are receiving, or the geometry of the structures (e.g. features used for ROI classification algorithm). Just as with the ROIs in the plan already, these ROIs can be processed through the ROI classifier and quality estimates algorithms to help ensure they are of sufficient quality prior to plan classification and quality estimation.

Example of Plan Error Detection

An example plan error detection algorithm can be designed in a similar manner as the ROI error detection algorithm, directly measuring quality from the probabilistic classifier output as in the case with Random Forest results used for ROI quality estimation.

Alternatively, using density estimation algorithms may provide a direct quality estimate in the form of a probability of observing a particular treatment plan given a combination of patient and treatment features. An example of this algorithm was used for the GUProstateVMAT results, described further below.

When both accepted and rejected treatment plans are available as historical data for training, then a classifier or regression algorithm (e.g., using a setting of 0 for acceptable plans, and 1 for rejected plans) such as Random Forest can be used to directly classify treatment plans and/or output a quality estimate (e.g., using Random Forest regression). An example of this algorithm was used for the BreastLeftCavitylMRT results, described further below.

Example of Integrated Classification Algorithm

Integrating ROIs and plans can be performed in any of the previous examples. A plan may have zero to many ROIs. Using the ROI classifier, all ROI labels may be known, and a distribution of ROIs can be calculated as a plan feature. This may model that a chest plan should typically include a left and right lung ROI, for example. The ROI classifier may already ensure that the heart ROI is smaller than the lung ROI, for example. Running the ROI classifier prior to integration may allow this phase to include specialized ROI based features, for example, the dose to the heart specifically. This feature may not be calculated prior to knowing which ROI is the heart. This method may thus provide a more natural workflow. A planner may first create ROIs, and then may check their quality using the ROI classifier. Once the ROIs are approved the planner may generate a plan. The plan classifier may then use ROI-based features as additional information to determine plan quality (e.g., dose to ROI, ROI shape, etc.). An aim of this may be to ensure that similar patients result in similar patient features. The quality estimation algorithm may then check how well the patient features pair up with the plan features, based on whether similar historical patients received historical treatment plans planned in a similar manner.

Another suitable method may be to build an integrated classifier that may use plan features to assist with ROI classification, and vice versa.

Various other approaches to detecting errors in ROIs and plans may also be suitable. An example approach may model any set of features rarely observed as a potential error using the learned probabilities in the classifier or a density estimation technique $P(F|class)$. For example, this approach is used in the ROI classifier detailed in TMI [48]. Another example approach may be to expressly train a classifier or regression algorithm on erroneous ROIs and plans. These other approaches can be used separately or together for greater flexibility.

Example of Quantitative Feature Analysis

Quantitative feature analysis may include estimating which features of a plan are erroneous, and performing any manual boundary checks on the plan (for example ensuring that the dose is less than a maximum hard-coded safe level for a particular patient age group). These features and rules can be taken directly from established medical treatment guidelines, for example.

The method for estimating which feature is responsible for a low plan quality may be dependent on which specific quality estimation algorithm is used. For example, with density estimation techniques, Bayes rule can be applied to estimate the probability of observing a particular plan feature (e.g. number of beams) given all other features. Or the probability of observing a plan feature (e.g. number of beams) can be calculated assuming patient features are observed, and summing out over all possible values for other plan features. This may, for example, report that 10 beams are rarely if ever used for these types of patients, and the planner should instead use 6.

Example of DICOM-RT Data Verification

An example of data verification may be paired with the Random Forest classifier (e.g., as discussed above) to help ensure that both plan versions end up at the same leaf of the trees. An alternative approach may be to ensure that the feature vectors match, and flag any step of the plan production pipeline that accidently change a feature.

Example Automated Dose Inference Algorithm for Automated Treatment Planning

In some examples, the automated treatment planning may build upon state-of-the-art methods from machine-learning and image processing. Image features, i.e. radiomic data, may be computed from a patient CT imaging and then mathematical regression may be used to infer what the personalized RT dose map should look like for that patient. The basic technological premise is that a given patient whose treatment is being planned would be expected to have a similar treatment plan to an existing similar patient in the historical database of treated patients. However, the disclosed method operates on a finer-grain level than simple patient-to-patient matching and learns more specific details relating the dose and anatomy. For example, the algorithm can learn that the corner of a lung with particular appearance (size, density) should be irradiated a particular way. In essence, the inference may match a novel image patch representing a 1×1×1 cm cubic region of the patient to millions of other patches in the database and then use the dose level from the most similar patches.

Radiomic features may be used to describe the image patches, and machine learning may be used to learn how to judge similarity between patches in a way that will accurately predict dose. In this way, it may be possible to recognize the difference between regions to avoid and target regions without requiring the standard approach of diligently delineating ROIs of the anatomy beforehand. For example, in breast RT, regions of the image recognized as the heart should typically be avoided and the proposed dose for these regions will be low, but regions at the interface between the lung and the breast and typically should be irradiated with a predicted dose close to the prescribed dose.

Inference of the proposed dose map may include the steps: i) Access a mass of exemplar historical data in the form of clinical treatment plans with corresponding CT images, and optionally divide the set into a training set and independent testing set (in some examples, an independent testing set may not be necessary); ii) Extract meaningful image features, i.e. radiomic data, from the CT data (e.g. texture, local image appearance, gradient); iii) Use a regression algorithm (e.g. Decision Forests [42]) to learn a non-linear multivariate regression model from the data that is capable of predicting the dose for novel CT images; and iv) Optionally, validate the predicted dose using the clinically delivered treatment plans for the testing data.

Example Automated Dose Inference Algorithm for Adaptive RT

The methodology described in the previous section may be expended to include information about previous treatment plans for use in a personalized adaptive RT context. The disclosed treatment planning methods may use imaging acquired during the course of treatment to adapt to anatomical changes that may result from treatment.

In some examples, the present disclosure may provide an automated, personalized adaptive RT method that involves training a suitable regression model [41,42,46] for the specific patient after the initial treatment planning has been approved, and that incorporate the delivered dose from each treatment thereafter. When changes in anatomy occur (e.g., rigid and/or deformable changes), these may be detected based on imaging acquired for each treatment day. The predicted dose may then be automatically updated for the current imaging data by determining the corresponding image patches in the context of the training database augmented with the imaging and the dose map from the previous treatment plans for that patient.

Adaptive RT may include the steps: i) adding the patient's treatment plan and corresponding repeat imaging to the historical database to re-train the machine learning algorithm to incorporate time-specific data to tailor to this specific patient; ii) calculate new time-dependent features based on repeat patient imaging; iii) infer an updated dose to account for anatomical changes; and iv) optionally validate for each imaging time point.

Example Validation and Results

The examples below discuss validation of an example embodiment of both the ROI and plan classification algorithms for an example automated QA method.

Example ROI QA Results

In this example, data consists of 17,579 ROIs from 1574 delivered treatment plans with 77 ROI classes. The data was gathered over one year from the Princess Margaret Cancer Centre in Toronto, Ontario. Each plan, created by a treatment planner (dosimetrist), contained a set of expert labelled ROIs, and had a corresponding DICOM CT image. ROIs may have resulted from manual or semi-automatic segmentation, but not fully automatic segmentation. Every plan was reviewed by multiple experts before being used for treatment in accordance with health and safety standards for RT. There are expected to be errors in the data. Some ROIs have been incorrectly labelled, and others have been incorrectly drawn. The example disclosed method was found to learn in-spite of these errors, and detect these errors.

Contour mislabelling errors may be directly detected via automated ROI classification. If the automatic ROI class label disagreed with the ROI class label in the input treatment plan, a mislabelling error may be reported. Contour quality assessment may be based on the posterior probabilities, as outlined above. This example study includes two types of experiments, those dealing with automatic ROI classification, and those relating to automatic quality assessment.

In order to evaluate the automatic quality assessment, a subset of 303 ROIs from 41 ROI classes was specifically re-evaluated by an expert to check for contouring errors. Only ROI classes for which the out-of-bag-error was lower than 10% were used.

Automatic Contour Classification

All classification experiments were performed using repeated random sub-sampling validation. The data was randomly split into two disjoint classes, with 941 (60%) for training plans and 639 (40%) testing plans. All learning and parameter tuning was done using the training data only, and then accuracy was evaluated on the testing set. Parameters included the maximum depth of each tree, and the number of variables examined per splitting node, n (e.g., as discussed above). The validation process was repeated for 40 random sub-samplings and the reported results were averaged across the random splits. Note that because plans and not ROIs were split into training and testing groups, the resulting ROI training and testing percentages were different.

Figure 9A:
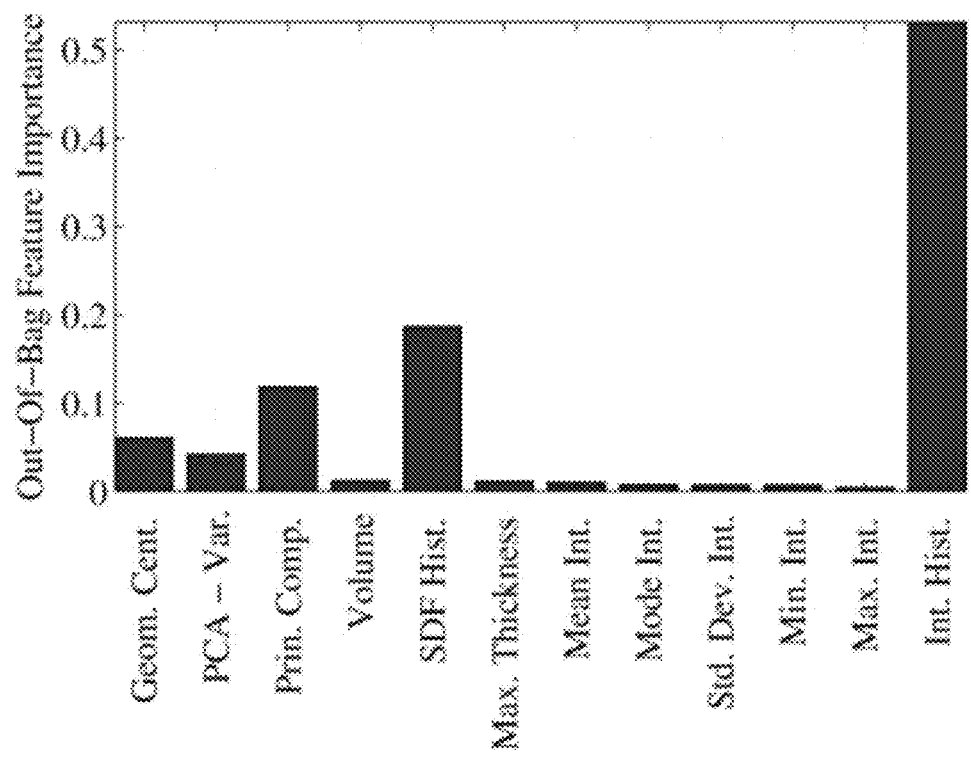
FIGS. 9a-9b are charts illustrating feature importance learned in example Random Forest and conditional Random Forest models.
Figure 9B:
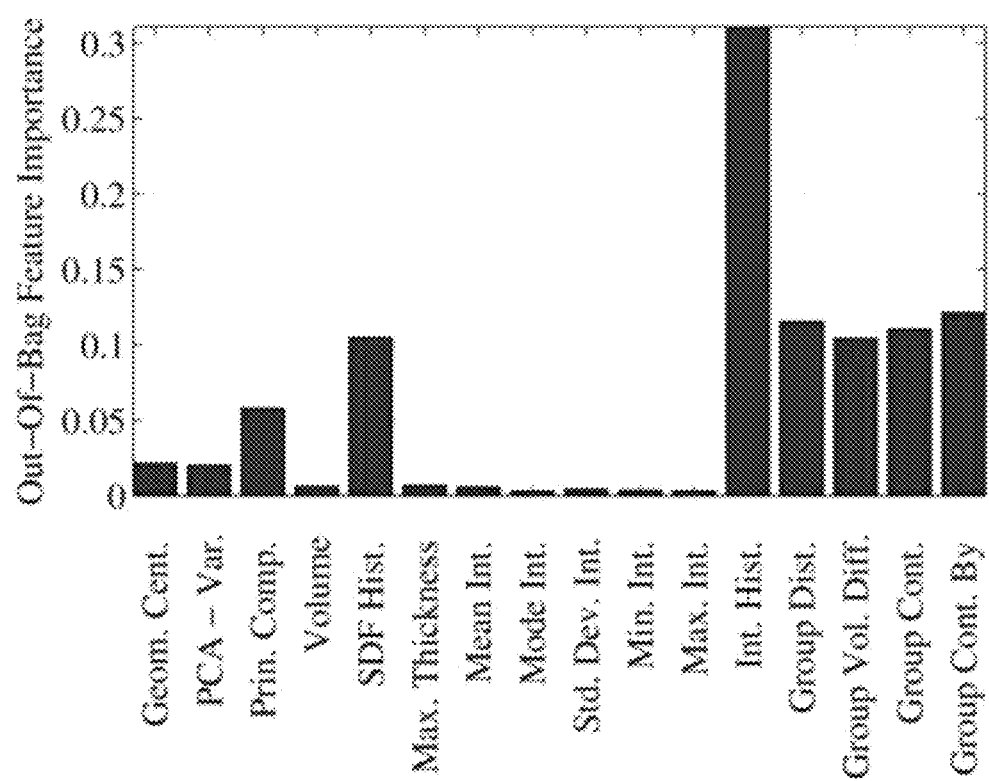

Parameter sensitivity of the example method studied is depicted in FIGS. 8a-8d, and learned feature importance is shown in FIGS. 9a-9b.

FIGS. 8a-8d illustrate parameter sensitivity in the example RF (8a, 8c) and conditional RF models (8b, 8d). Error bars are presented across the 40 random sub-samplings of training and testing data. Out-of-bag accuracy is presented in blue (indicated as "1"), with accuracy for the testing data in red (indicated as "2"). The example models were found to be stable over a relatively wide range of parameters and did not exhibit any strong evidence of over-fitting.

FIGS. 9a-9b illustrate feature importance learned in the example RF (9a) and conditional RF models (9b). The groupwise features in (9b) indicate a relatively strong influence. Vector valued features appear as a summation over the entire feature vector.

Maximal tree depth and the number of splitting variables were learned automatically for each of the 40 random sub-samplings by finding where the out-of-bag-error flattens out as a function of the dependent parameter. For this example RF the average learned maximal depth was 17, and the number of splitting variables was 37. For this example conditional RF, the maximal depth was 16, and the number of splitting variables was 43. The intensity histogram contained 160 bins, and the SDF histogram contained 30. These values were set manually by examining random ROIs and then fixed for all experiments.

This example learning method was compared with the canonical RFs, naive Bayes (NB), artificial neural network (ANN), support vector machine (SVM) classification algorithms. Each competing method's parameters were estimated via cross-validation. NB and ANN implementations used built-in MATLAB toolboxes, and libSVM was used for SVM with a radial basis kernel function [69]. The example learning method was considered both with and without groupwise conditional features and groupwise inference. Where applicable results for the example learning method were reported using both approximate and exact inference. The complete set of organs at risk and other reference structures considered in this example study is listed in Table 6 (FIGS. 14a-14c), while clinical targets are listed in Table 7 (FIGS. 15a-15c). In cases where ROI classes (e.g., Heart) appeared in multiple treatment plan classes, only one treatment plan type has been listed. Average training and testing set sizes for each class are presented.

Example results are listed in Table 4a (FIG. 7a) and Table 4b (FIG. 7b). The total accuracy of a classifier was defined as the percentage of correct classifications across all classes (i.e., total number of correct classifications divided by total number of testing ROIs), in comparison to the ROI labels provided by the treatment planners (dosimetrist). Total accuracy across all classes is presented, for OARs, and for targets. Results were averaged across the 40 random sub-samplings. The "Accuracy Std. Dev." is the standard deviation of the total accuracy across all 40 random sub-samplings of the training and testing data. The true positive and false positive classification rates were calculated for each ROI class. True positive rates (TPR) and false positive rates (FPR) are presented for each individual ROI class in Table 6 and Table 7 (FIGS. 14a-14c and 15a-15c) for the example Groupwise Conditional RF method. Statistics for TPR and FPR in Table 4a (FIG. 7a) were computed across all ROI classes unless otherwise noted. The "Avg. TPR" was calculated for each individual ROI class as an average over the 40 random sub-samplings, and then the average TPR was calculated across all 77 classes. These measures may indicate the accuracy of the system in data mining applications, or in fully automatically re-labelling of ROIs.

The results for flagging potential labelling errors for expert review may be related, but somewhat different. The overall TPR for detecting ROI mislabelling errors across all classes was lower bounded by the total accuracy of the classifier, 91.58%. The FPR for mislabelling errors was one minus the total accuracy, or 8.42%. The system was found to correctly identify any ROI mislabelling error for which it correctly classifies the ROI, and may miss any mislabelling for which it incorrectly classifies the ROI. The TPR was lower bounded by the total accuracy because the example classifier flagged an error wherever it disagreed with the input plan, even if it is also wrong about the ROI label in question. When the classifier outputted the same incorrect label as the input plan, a ROI mislabelling may go un-noticed. In other words, a mislabelling error false negative for a given ROI class may only occur when a classifier false positive is of the same class. Left lung had a mislabelling error detection TPR of 99.96%, or one minus the FPR from Table 6 (FIGS. 14a-14c). The average TPR across all ROI classes for mislabelling error detection was, therefore, one minus the "Avg. FPR" from Table 4a (FIG. 7a), or 99.89%. The expected value of the TPR for mislabelling error detection across all ROI classes given observed class distributions was 99.65%. An example of a mislabelling error may be where the left lung has been labelled as the right, and vice versa. The example disclosed method was able to correctly identify the mistake and accurately relabelled each lung.

Using the same analysis, a more comprehensive dataset was used in Table 4b (FIG. 7b). The dataset consisted of 59,400 ROIs from 6,199 delivered plans and compromised 307 distinct ROI classes. The overall TPR for detecting ROI mislabelling errors across all 307 classes was lower bounded by the total accuracy of the classifier, 89.85%.

Automatic Quality Assessment

Whereas the previous section detailed example results for detecting mislabelled ROIs, this section deals with detecting errors relating to contouring quality itself. A poorly drawn heart ROI is an example of an actual contouring error that, while missed during rigorous treatment plan review, may be automatically detected by the example disclosed method. During treatment plan review it may be impractical for a medical expert to manually review every slice of every contour, and so errors like this can often go un-noticed.

Figure 10:
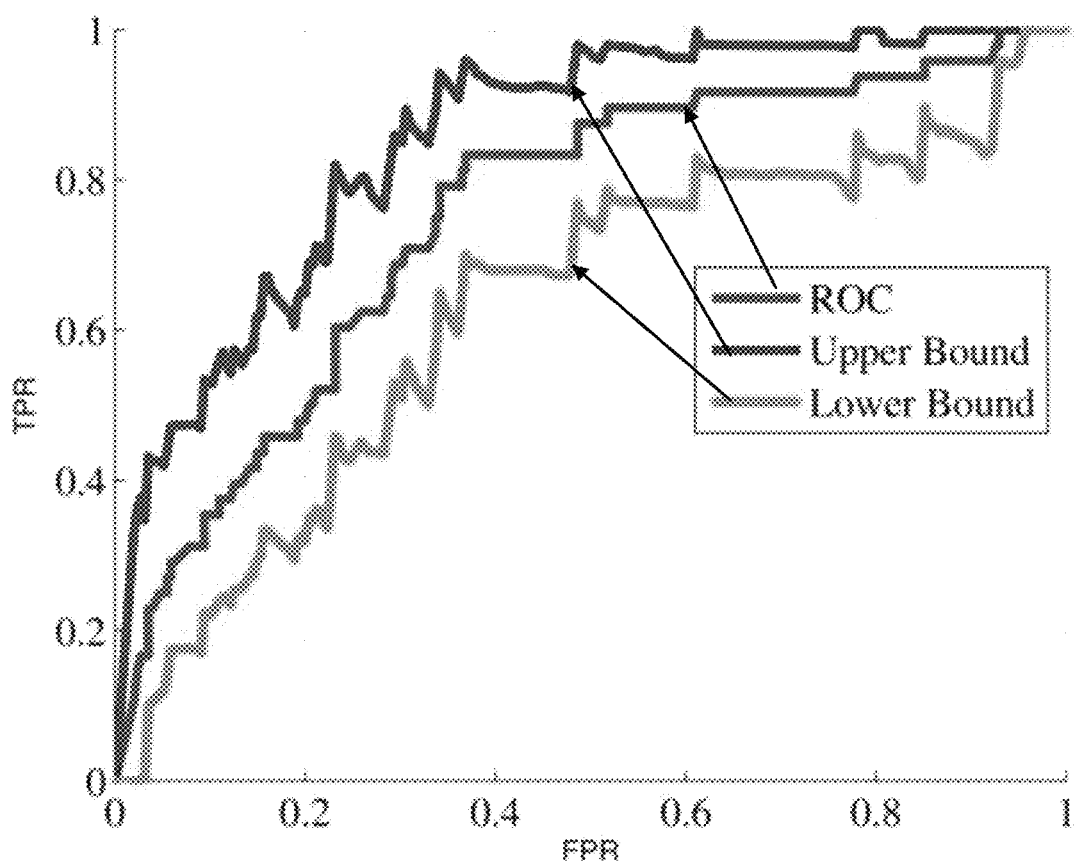
FIG. 10 is a chart illustrating confidence interval for detection of contour drawing errors in ROIs, in an example of the present disclosure.

For these example experiments training was using all plans except those containing one or more of the 303 manually re-evaluated ROIs. Of the 303 ROIs, 48 had contouring errors, as determined by an expert. For all 303 ROIs it was predicted whether or not a contouring error has occurred by thresholding the class posterior s. The ROC curve for different thresholds, using an example of the disclosed method, is shown in FIG. 10, using bootstrapping and averaging over the FPR to compute a 95% confidence band. The area under the curve (AUC) was 0.75 with a 95% confidence interval of [0.67, 0.82] with bootstrapping or [0.63, 0.87] using another standard method [70]. Based on the ROC curve a threshold of 63% was selected for illustrating example true and false positives.

Figure 11A:
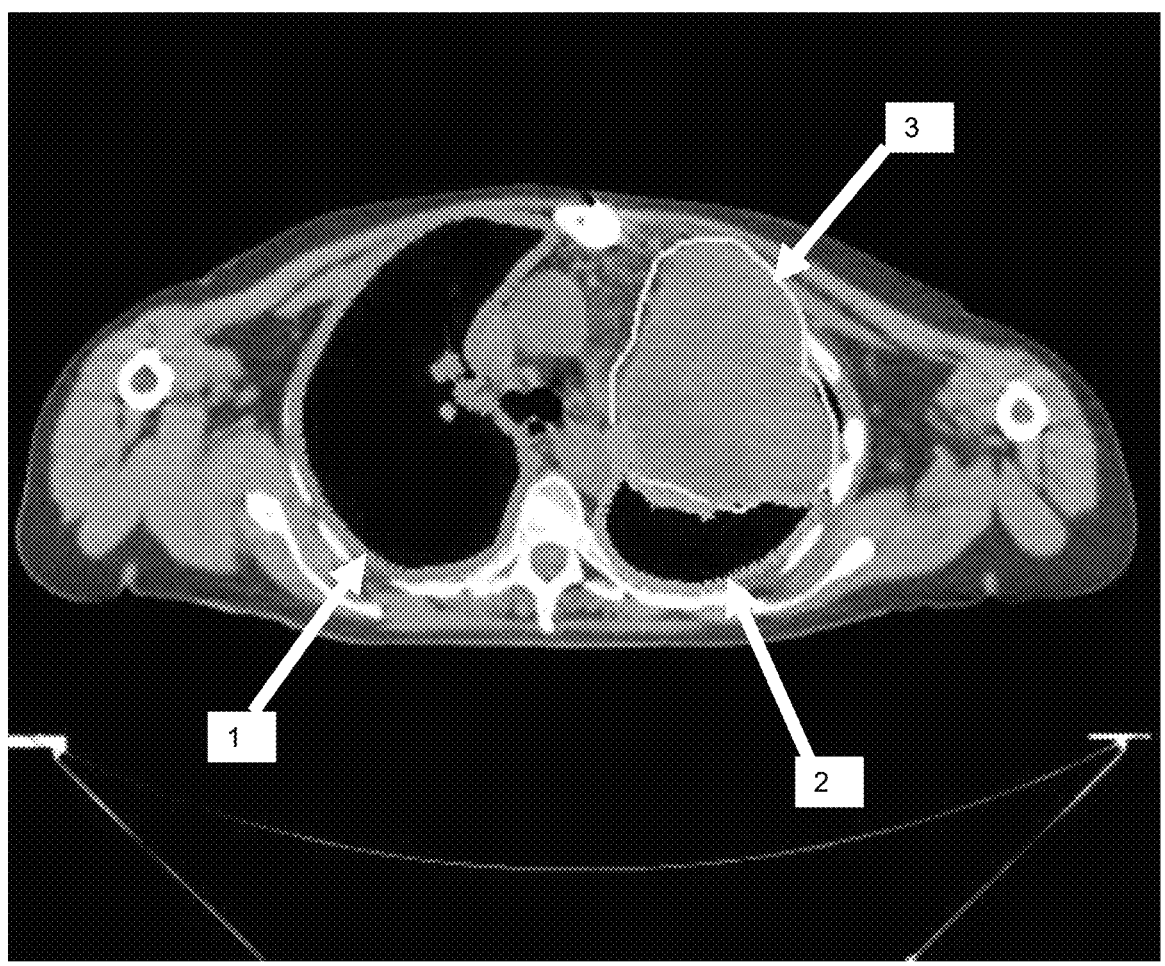
FIGS. 11a-11c illustrate an example of a false positive in a delineation of lung ROI.
Figure 11B:
Figure 11C:
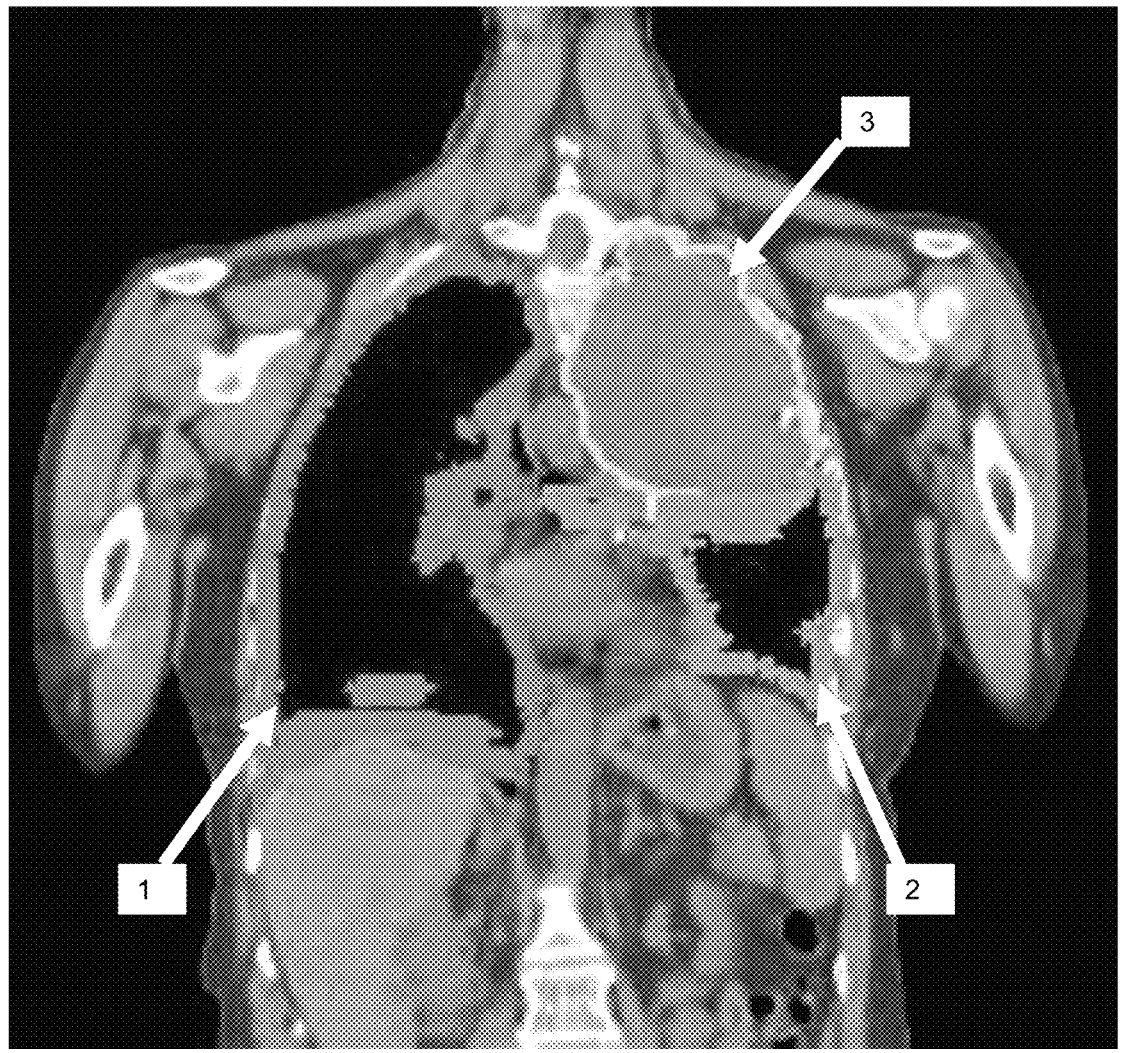

FIGS. 11a-11c show an example false positive for lung ROIs in the presence of a large tumour. The size of the left lung, in orange (indicated as "2"), has been reduced by the large tumour in yellow (indicated as "3"). The automatic quality estimate for the left lung is $\varepsilon=0.44$ in comparison to the right lung (indicated as "1") with $\varepsilon=0.88$.

Figure 12A:
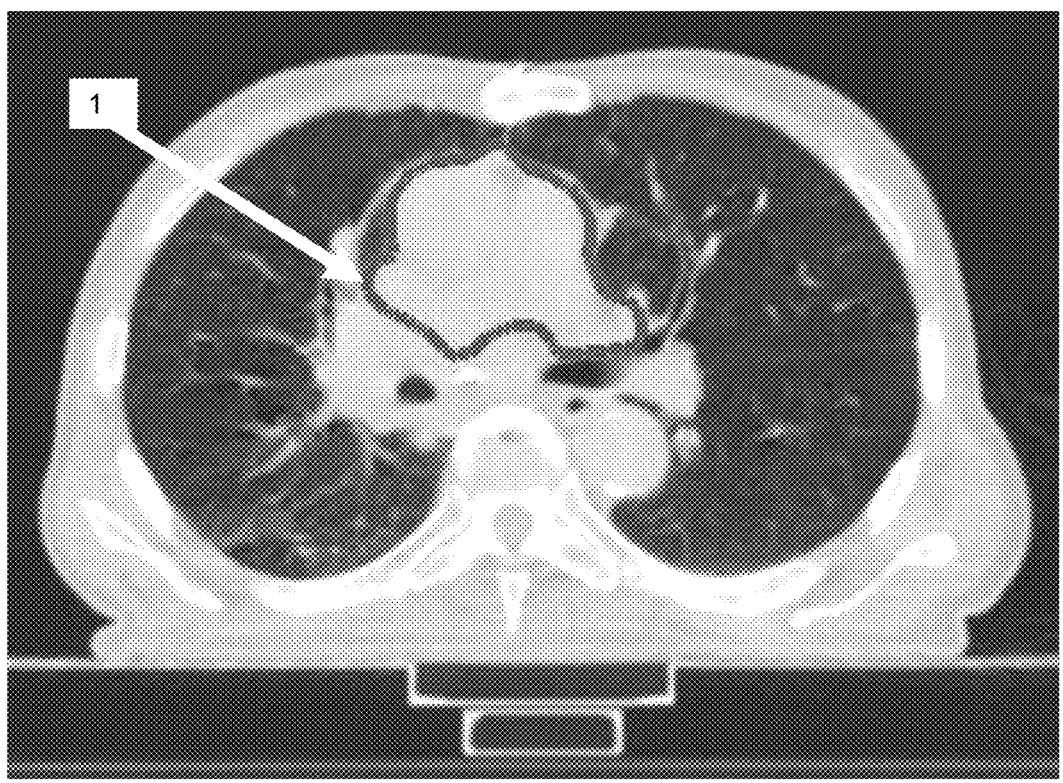
FIGS. 12a-12c illustrate an example of a false negative in a delineation of heart ROI.
Figure 12B:
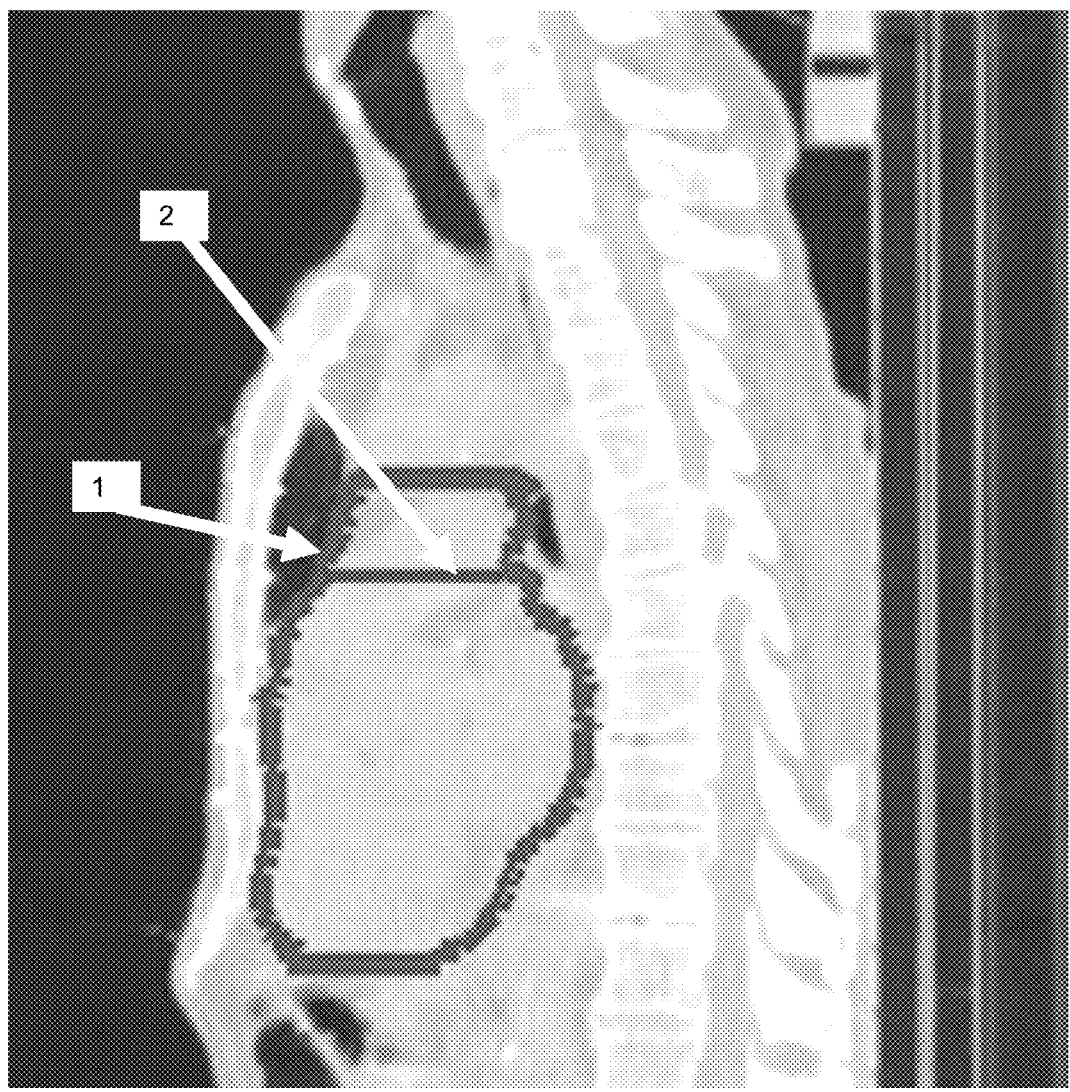
Figure 12C:
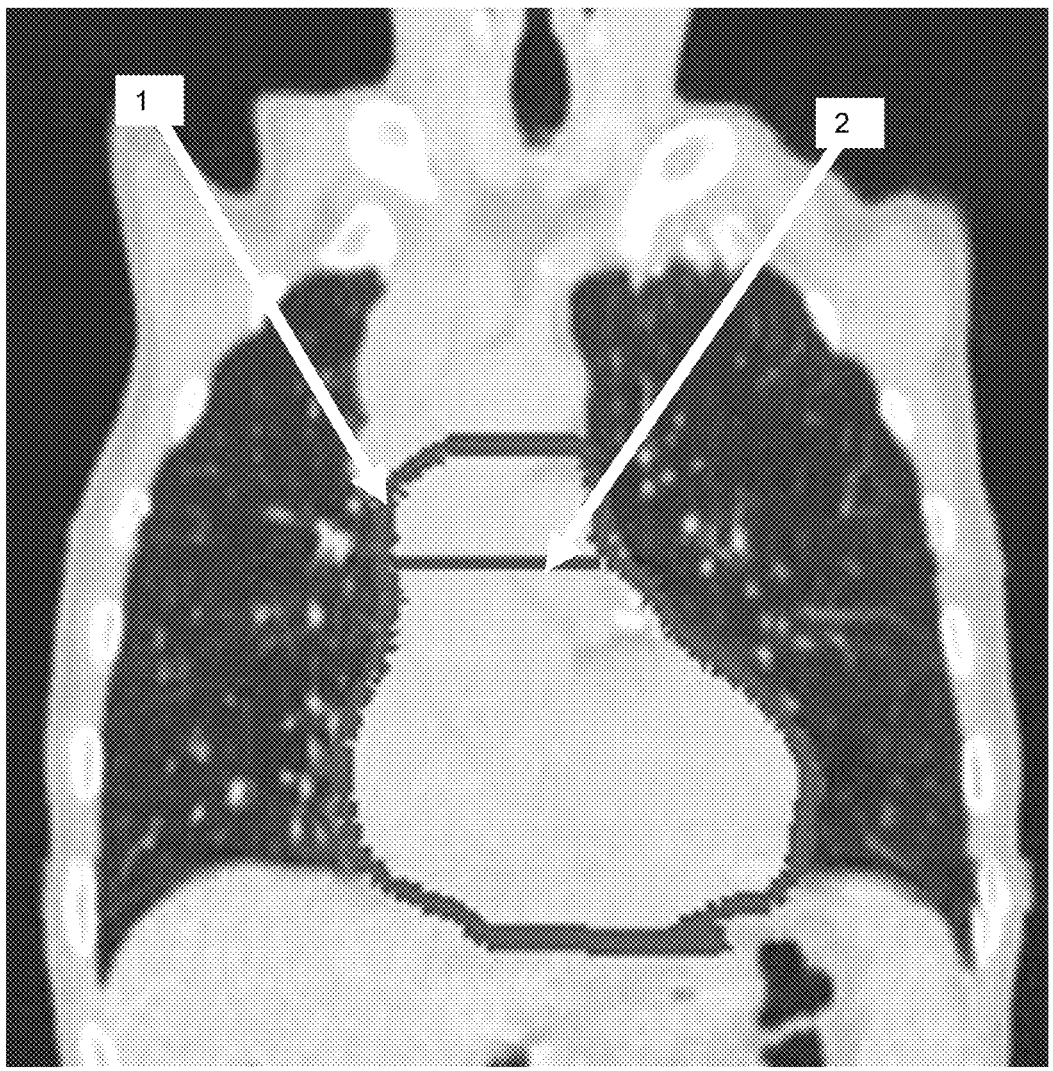

FIGS. 12a-12c show an example false negative in a poorly contoured heart ROI. The heart ROI in green (indicated as "1") was mistakenly drawn to include part of the aorta. Red lines (indicated as "2") in FIG. 12b and FIG. 12c show approximately where the contour should have ended. The automatic quality estimate for this heart ROI was $\varepsilon=0.72$. In comparison, an example jagged heart contour was found to have $\varepsilon=0.54$, indicating that the type of contouring abnormality shown in FIGS. 12a-12c may be more common in the historical data.

Example Plan Classification Results

For validation of the example plan classification method, collected 7933 clinical treatment plans were collected from 103 different treatment plan classes over two years. The accuracy using the example embodiment discussed above, RF with histograms of fraction, beam, and control point features over dictionaries, was found to be 78.01% (See Table 5, FIGS. 13a-13c).

Example Automated Treatment Plan Error Detection Results

Figure 16A:
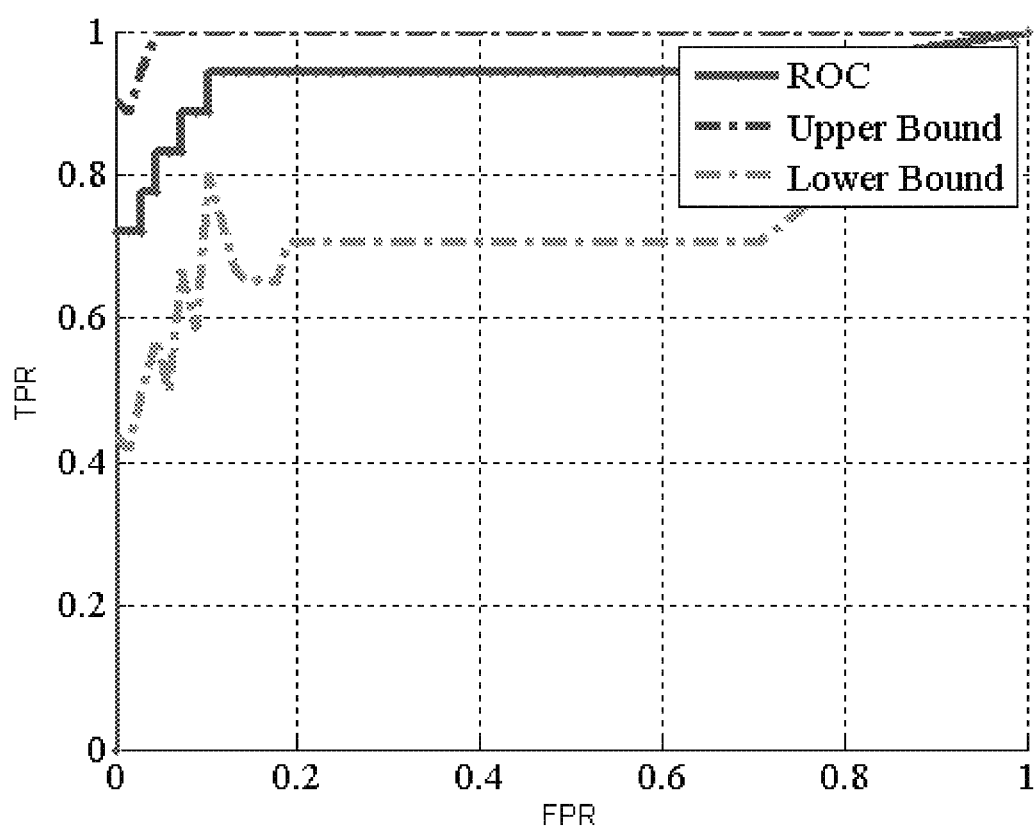
FIGS. 16a-16b show charts illustrating confidence interval for detection of errors in treatment plans, in an example of the present disclosure.

For these example experiments training was done for a single treatment plan class at a time. In FIG. 16a the treatment plan class was BreastLeftCavityIMRT. On a quality estimate threshold of 0.45, leave-one-out, validation was done on 86 breast plans (68 clinically acceptable plans and 18 rejected plans with errors, 10 of which were simulated errors). The TPR and FPR were 0.9444 and 0.1029, respectively. The ROC curve for different thresholds, using an example of the disclosed method, is shown in FIG. 16a, using bootstrapping and averaging over the FPR to compute a 95% confidence band. Based on the ROC curve a threshold of 45% was selected for illustrating example true and false positives.

Figure 16B:
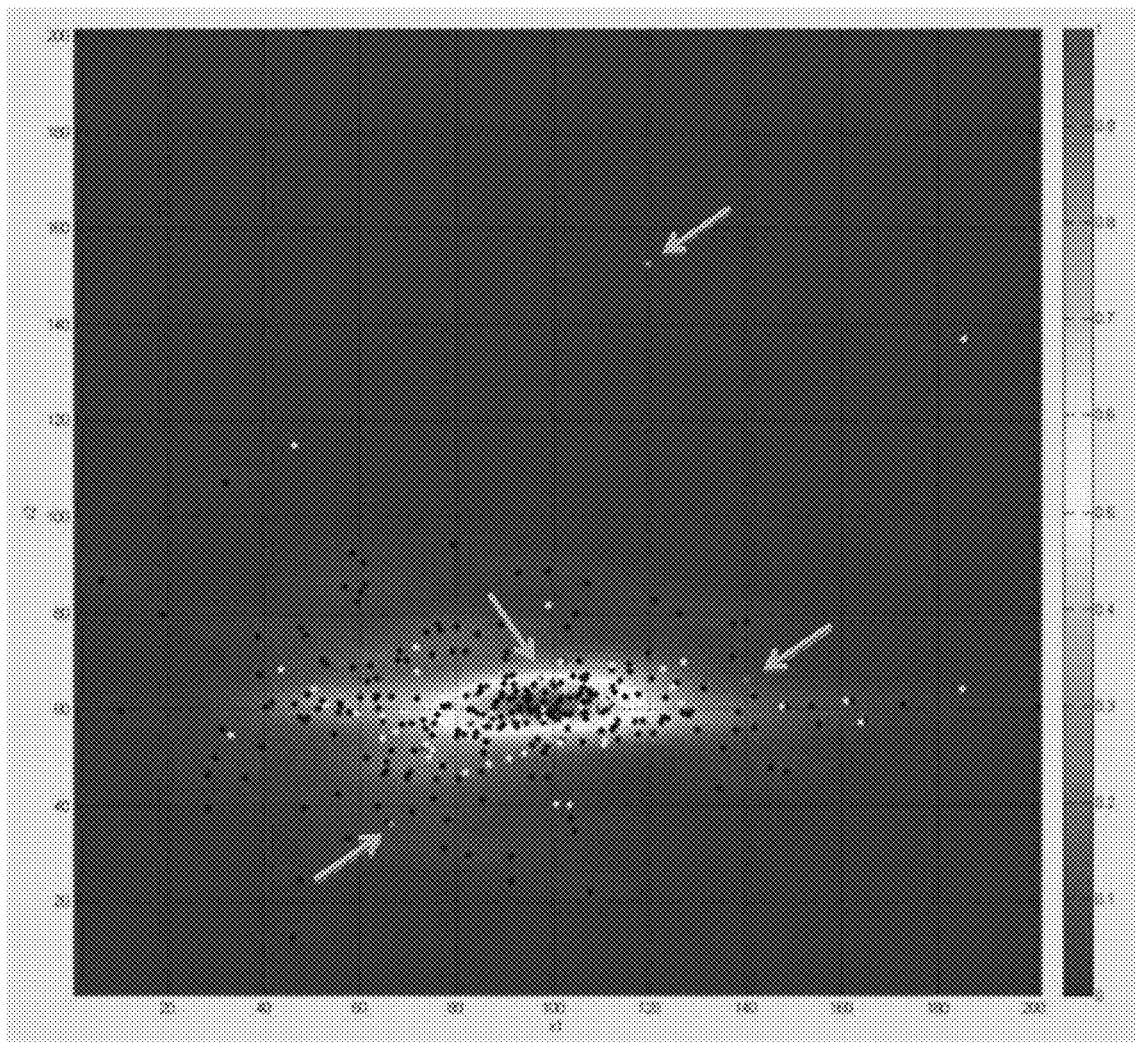

In FIG. 16b the treatment plan class was GUProstateVMAT. Visualizing the quality estimation space of prostate plans using multidimensional scaling [71] to reduce the feature space to two dimensions, x1, and x2, followed by kernel density estimation [46]. The data shows 273 treatment plans for training (black circles) and 61 treatment plans for testing (white circles). For this plan class there were 4 clinical errors (grey circles highlighted by errors).
Example Automated Dose Inference Results FIGS. 22a-22c show example CT images. FIG. 22a shows example CT images for a typical BreastLeftBreastTangent (Top) and GUProstateVMAT (Bottom) RT plan. Also shown are the corresponding automated inferred dose maps (FIG. 22b) and clinical dose maps (FIG. 22c) over the entire image. The dose scale shows fraction of the prescription dose. For both automated plans, the dose map predicted was based on images only and did not include any delineated ROIs.

Table 10, FIG. 23 shows a summary of results from the example treatment plan classes of FIGS. 22a-22c showing validation of dose map inference for automated treatment planning in 20 novel patients of each class. The correlation between predicted and clinical dose maps is shown for the BreastLeftBreastTangent and GUProstateVMAT treatment plan classes.
Possible Variations and Applications Some example variations and applications of the present disclosure are discussed below for the purpose of illustration. Other variations and applications may be possible.

The present disclosure may be useful for automated treatment planning and/or data mining applications, among others, as discussed below.

The present disclosure can be used for education and training of trainees i.e. radiation oncology residents, radiation oncology fellows, radiation physics residents and RT technology students, and for RT staff i.e. radiation oncologists, radiation (medical) physicists and RT technologists. For example, the disclosed systems and methods can be used such that a user may perform any task during treatment planning (e.g., target and organ delineation, generating treatment plans, etc.) and may receive as output a report on the acceptability of the individual volume delineations or treatment plans compared with historical plans. In some examples, this may be provided as remote learning in which users can receive feedback without having to sit down with a particular expert. The example system can use a remote database and may be system independent.

Using the same historical data that the example system is built on to do QA verification, the example system can also provide an optimized treatment plan and regions of interest for a particular plan class. The example system may produce the treatment plan class based on the particular features from the plan and compare the new plan with the expected plan class to see if it matches. This could also apply to ROIs. Thus, the example system can be used for image segmentation.

The present disclosure may be suited to the clinical trial environment. Examples of the disclosed methods and systems may accept data from remote sources, interrogate the data and provide an automated analysis. This may help to ensure clinical trial compliance and provide participating institutions rapid review of their submission to facilitate real-time review.

There may be many options for incorporating the disclosed methods and systems into a clinical workflow. For example, the clinician may use an example of the disclosed methods and systems to verify ROIs manually, semi-automatically or automatically generated before treatment planning; the planner may use an example of the disclosed methods and systems to verify and provide a pre-QA of an entire treatment plan before it goes for review to oncology and physics; or the physicist and oncologist may use an example of the disclosed methods and systems to perform QA and approve/reject completed treatment plans generated from a planner. These example options may be non-exclusive. All options can be used for a plan review.

Data-mining may be another application of this disclosure. Clinical databases are often fraught with errors such as mislabelled ROIs, and un-classified data. However, it may be desirable to retrospectively search a clinical database and find all of the lung ROIs, or all of the lung treatment plans, or ever lung treatment plan with a heart ROI, for example. A challenge in doing so is that databases often contain incorrect or inconsistent labels, for example the left lung ROIs might be labelled "Left Lung", "L Lung", "Lung Left", "LLung", or even labelled "heart" by mistake. The present disclosure may enable users to automatically search a database for all items of a particular class, regardless of the label, and thus find all lungs, for example, regardless of the used nomenclature. Once processed by the example system, the data can be used for other research studies.

Another possible application may be the ability to use the disclosed automated QA system to triage or flag plans that have been scored poorly and then focus the review to these plans. As evidence by a recent poll of academic institutions [11], the implementation and conduct of peer review rounds may be inconsistent across academic institutions with relatively little time spent reviewing individual patients. Patient history, patient chart documentation, and dose prescription may be peer reviewed whereas dosimetric details related to the treatment plans including target coverage and normal tissue doses and technical parameters related to the treatment plans may be typically reviewed in only half of the cases. Therefore, an example of the disclosed QA system may provide a better use of time by allowing the team to focus on potential problems flagged by the example system.

Although the present disclosure describes methods and processes with steps in a certain order, one or more steps of the methods and processes may be omitted or altered as appropriate. One or more steps may take place in an order other than that in which they are described, as appropriate.

While the present disclosure is described, at least in part, in terms of methods, a person of ordinary skill in the art will understand that the present disclosure is also directed to the various components for performing at least some of the aspects and features of the described methods, be it by way of hardware components, software or any combination of the two, or in any other manner. Moreover, the present disclosure is also directed to a pre-recorded storage device or other similar non-transient computer readable medium including program instructions stored thereon for performing the methods described herein, including DVDs, CDs, volatile or non-volatile memories, or other storage media, for example.

The present disclosure may be embodied in other specific forms without departing from the subject matter of the claims. The described example embodiments are to be considered in all respects as being only illustrative and not restrictive. Selected features from one or more of the above-described embodiments may be combined to create alternative embodiments not explicitly described, features suitable for such combinations being understood within the scope of this disclosure.

All values and sub-ranges within disclosed ranges are also disclosed. Also, while the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. The subject matter described herein intends to cover and embrace all suitable changes in technology. All references mentioned are hereby incorporated by reference in their entirety.

REFERENCES

[1] Canadian Cancer Society I Statistics Canada. Canadian Cancer Statistics. 2013.

[2] Cancer Quality Council of Ontario. Radiation Treatment Utilization. Canadian Quality Council of Ontario; 2013.

[3] Schilling E G, Neubauer D V. Acceptance sampling in quality control. 2nd ed. CRC Press; 2009.

[4] Bissonnette J-P, Medlam G. Trend analysis of radiation therapy incidents over seven years. Radiother Oncol 2010; 96:139-44.

[5] Huang G, Medlam G, Lee J, Billingsley S, Bissonnette J P, Ringash J, et al. Error in the delivery of radiation therapy: results of a quality assurance review. Int J Radiat Oncol Biol Phys 2005; 61:1590-5.

[6] Peters L J, O'Sullivan B, Giralt J, Fitzgerald T J, Trotti A, Bernier J, et al. Critical impact of radiotherapy protocol compliance and quality in the treatment of advanced head and neck cancer: results from TROG 02.02. J Clin Oncol 2010; 28:2996-3001.

[7] Abrams R A, Winter K A, Regine W F, Safran H, Hoffman J P, Lustig R, et al. Failure to adhere to protocol specified radiation therapy guidelines was associated with decreased survival in RTOG 9704—a phase III trial of adjuvant chemotherapy and chemoradiotherapy for patients with resected adenocarcinoma of the pancreas. Int 3 Radiat Oncol Biol Phys 2012; 82:809-16.

[8] Purdy J a. Quality assurance issues in conducting multi-institutional advanced technology clinical trials. Int 3 Radiat Oncol Biol Phys 2008; 71:S66-70.

[9] Ellerbroek N A, Brenner M, Hulick P, Cushing T. Practice accreditation for radiation oncology: quality is reality. J Am Coll Radiol 2006; 3:787-92.

[10] Hulick P R, Ascoli F a. Quality assurance in radiation oncology. J Am Coll Radiol 2005; 2:613-6.

[11] Lawrence Y R, Whiton M a, Symon Z, Wuthrick E J, Doyle L, Harrison A S, et al. Quality Assurance Peer Review Chart Rounds in 2011: A Survey of Academic Institutions in the United States. Int J Radiat Oncol Biol Phys 2012; 84:590-5.

[12] Moore K L, Brame R S, Low D a, Mutic S. Quantitative metrics for assessing plan quality. Semin Radiat Oncol 2012; 22:62-9.

[13] Ishikura S. Quality assurance of radiotherapy in cancer treatment: toward improvement of patient safety and quality of care. Jpn J Clin Oncol 2008; 38:723-9.

[14] Marks L B, Jackson M, Xie L, Chang S X, Burkhardt K D, Mazur L, et al. The challenge of maximizing safety in radiation oncology. Pract Radiat Oncol 2011; 1:2-14.

[15] Esch A Van, Bogaerts R, Kutcher G J, Van Esch A, Huyskens D. Quality assurance in radiotherapy by identifying standards and monitoring treatment preparation. Radiother Oncol 2000; 56:109-15.

[16] Hendee W. Patient safety and the medical physicist. Med Phys 2011; 38:i-ii

[17] Hendee W R, Herman M G. Improving patient safety in radiation oncology. Med Phys 2011; 38:78-82.

[18] Ford E C, Terezakis S. How safe is safe? Risk in radiotherapy. Int J Radiat Oncol Biol Phys 2010; 78:321-2.

[19] Huq M S, Fraass B a, Dunscombe P B, Gibbons J P, Ibbott G S, Medin P M, et al. A method for evaluating quality assurance needs in radiation therapy. Int J Radiat Oncol Biol Phys 2008; 71:S170-3.

[20] Furhang E E, Dolan J, Sillanpaa J K, Harrison L B. Automating the initial physics chart checking process. J Appl Clin Med Phys 2009; 10:2855.

[21] Yang D, Moore K L. Automated radiotherapy treatment plan integrity verification. Med Phys 2012; 39:1542-51.

[22] Zhao B, Joiner M C, Orton C G, Burmeister J. "SABER": A new software tool for radiotherapy treatment plan evaluation. Med Phys 2010; 37:5586-92.

[23] Azmandian F, Kaeli D, Dy J G, Hutchinson E, Ancukiewicz M, Niemierko A, et al. Towards the development of an error checker for radiotherapy treatment plans: a preliminary study. Phys Med Biol 2007; 52:6511-24.

[24] Nelms B E, Tome W a, Robinson G, Wheeler J. Variations in the contouring of organs at risk: test case from a patient with oropharyngeal cancer. Int J Radiat Oncol Biol Phys 2012; 82:368-78.

[25] Nelms B E, Robinson G, Markham J, Velasco K, Boyd S, Narayan S, et al. Variation in external beam treatment plan quality: An inter-institutional study of planners and planning systems. Pract Radiat Oncol 2012; 2:296-305.

[26] Moore K L, Kagadis G C, McNutt T R, Moiseenko V, Mutic S. Vision 20/20: Automation and advanced computing in clinical radiation oncology. Med Phys 2014; 41:010901.

[27] Purdie T G, Dinniwell R E, Letourneau D, Hill C, Sharpe M B. Automated planning of tangential breast intensity-modulated radiotherapy using heuristic optimization. Int J Radiat Oncol Biol Phys 2011; 81:575-83.

[28] Good D, Lo J, Lee W R, Wu Q J, Yin F-F, Das S K. A knowledge-based approach to improving and homogenizing intensity modulated radiation therapy planning quality among treatment centers: an example application to prostate cancer planning. Int J Radiat Oncol Biol Phys 2013; 87:176-81.

[29] Ghobadi K, Ghaffari H R, Aleman D M, Jaffray D A, Ruschin M. Automated treatment planning for a dedicated multi-source intracranial radiosurgery treatment unit using projected gradient and grassfire algorithms. Med Phys 2012; 39:3134-41.

[30] Voet P W J, Dirkx M L P, Breedveld S, Al-Mamgani A, Incrocci L, Heijmen B J M. Fully automated volumetric modulated arc therapy plan generation for prostate cancer patients. Int J Radiat Oncol Biol Phys 2014; 88:1175-9.

[31] Zhao X, Kong D, Jozsef G, Chang J, Wong E K, Formenti S C, et al. Automated beam placement for breast radiotherapy using a support vector machine based algorithm. Med Phys 2012; 39:2536-43.

[32] Xhaferllari I, Wong E, Bzdusek K, Lock M, Chen J. Automated IMRT planning with regional optimization using planning scripts. J Appl Clin Med Phys 2013; 14.

[33] Kazhdan M, Simari P, McNutt T, Wu B, Jacques R, Chuang M, et al. A shape relationship descriptor for radiation therapy planning. Lect Notes Comput Sci 2009; 5762:100-8.

[34] Wu B, Ricchetti F, Sanguineti G, Kazhdan M, Simari P, Chuang M, et al. Patient geometry-driven information retrieval for IMRT treatment plan quality control. Med Phys 2009; 36:5497.

[35] Webb S. Intensity-modulated radiation therapy. CRC Press; 2001.

[36] Lee T, Hammad M, Chan T C Y, Craig T, Sharpe M B. Predicting objective function weights from patient anatomy in prostate IMRT treatment planning. Med Phys 2013; 40:121706.

[37] Ehrgott Güler ç, Hamacher H W, Shao L. Mathematical optimization in intensity modulated radiation therapy. 4O R 2008; 6:199-262.

[38] Marčelja S. Mathematical description of the responses of simple cortical cells*. JOSA 1980:1297-300.

[39] Fedkiw S O R. Level set methods and dynamic implicit surfaces. Springer; 2003.

[40] Goshtasby A A. 2-D and 3-D image registration: for medical, remote sensing, and industrial applications. John Wiley & Sons; 2005.

[41] Drucker H, Burges C J C, Kaufman L, Smola A, Vapnik V. Support vector regression machines. Adv Neural Inf Process Syst 1997; 9:155-61.

[42] Breiman L. Random Forests. Mach Learn 2001; 45:5-32.

[43] Wu G, Wang Q, Zhang D, Shen D. Robust patch-based multi-atlas labeling by joint sparsity regularization. MICCAI Work. STMI, 2012.

[44] Gee J C, Reivich M, Bajcsy R. Elastically deforming 3D atlas to match anatomical brain images. J Comput Assist Tomogr 1993; 17:225-36.

[45] Zikic D, Glocker B, Criminisi A. Atlas encoding by randomized forests for efficient label propagation. Med. Image Comput. Comput. Interv. 2013, Springer; 2013, p. 66-73.

[46] Bishop C M. Pattern Recognition and Machine Learning (Information Science and Statistics). Springer-Verlag New York, Inc.; 2006.

[47] Vincent P, Larochelle H, Lajoie I, Bengio Y, Manzagol P-A. Stacked denoising autoencoders: Learning useful representations in a deep network with a local denoising criterion. J Mach Learn Res 2010; 9999:3371-408.

[48] McIntosh C, Svistoun I, Purdie T G. Groupwise conditional random forests for automatic shape classification and contour quality assessment in radiotherapy planning. IEEE Trans Med Imaging 2013; 32:1043-57.

[49] Yang L, Jin R. Distance metric learning: A comprehensive survey. Michigan State Universiy 2006; 2.

[50] Osher S, Sethian J A. Fronts Propagating with Curvature Dependent Speed: Algorithms Based on Hamilton-Jacobi Formulations. J Comput Phys 1988; 79:12-49.

[51] Criminisi A, Shotton J, Konukoglu E. Decision forests for classification, regression, density estimation, manifold learning and semi-supervised learning. Microsoft Res Cambridge, Tech . . . 2011.

[52] Lafferty J D, McCallum A, Pereira F C N. Conditional Random Fields: Probabilistic Models for Segmenting and Labeling Sequence Data. ICML 2001:282-9.

[53] Kolmogorov V, Rother C. Minimizing Nonsubmodular Functions with Graph Cuts-A Review. IEEE Trans Pattern Anal Mach Intell 2007; 29:1274-9.

[54] Boykov Y, Funka-Lea G. Graph Cuts and Efficient N-D Image Segmentation. Int J Comput Vis 2006; 70:109-31.

[55] Boykov Y Y, Jolly M-P. Interactive graph cuts for optimal boundary & region segmentation of objects in N-D images. Comput Vision, 2001 ICCV 2001 Proceedings Eighth IEEE Int Conf 2001; 1:105-12.

[56] Papadimitriou C H, Steiglitz K. Combinatorial optimization: algorithms and complexity. Dover Publications Inc., Mineola, N.Y.; 1998.

[57] Pati Y C, Rezaiifar R, Krishnaprasad P S. Orthogonal matching pursuit: Recursive function approximation with applications to wavelet decomposition. Signals, Syst. Comput. 1993. 1993 Conf. Rec. Twenty-Seventh Asilomar Conf., IEEE; 1993, p. 40-4.

[58] Olshausen B A, Field D J. Sparse coding with an overcomplete basis set: a strategy employed by V1? Vision Res 1997; 37:3311-25.

[59] Wu T T, Lange K. Coordinate descent algorithms for lasso penalized regression. Ann Appl Stat 2008:224-44.

[60] Mairal J, Bach F, Ponce J, Sapiro G, Zisserman A. Supervised dictionary learning 2008.

[61] Blumensath T, Davies M E. On the difference between orthogonal matching pursuit and orthogonal least squares 2007.

[62] LeCun Y, Bottou L, Bengio Y, Haffner P. Gradient-based learning applied to document recognition. Proc IEEE 1998; 86:2278-324.

[63] Hinton G E, Osindero S, Teh Y-W. A fast learning algorithm for deep belief nets. Neural Comput 2006; 18:1527-54.

[64] Salakhutdinov R, Hinton G E. Deep boltzmann machines. Int. Conf. Artif. Intell. Stat., 2009, p. 448-55.

[65] Lee H, Grosse R, Ranganath R, Ng A Y. Convolutional deep belief networks for scalable unsupervised learning of hierarchical representations. Proc. 26th Annu. Int. Conf. Mach. Learn., ACM; 2009, p. 609-16.

[66] Coates A, Ng A Y. The importance of encoding versus training with sparse coding and vector quantization. Proc. 28th Int. Conf. Mach. Learn., 2011, p. 921-8.

[67] Qazi A A, Pekar V, Kim J, Xie J, Breen S L, Jaffray D A. Auto-segmentation of normal and target structures in head and neck C T images: a feature-driven model-based approach. Med Phys 2011; 38:6160-70.

[68] Pekar V, McNutt T R, Kaus M R. Automated model-based organ delineation for radiotherapy planning in prostatic region. Int 3 Radiat Oncol Biol Phys 2004; 60:973-80.

[69] Chang C-C, Lin C-J. LIBSVM: A library for support vector machines. ACM Trans Intell Syst Technol 2011; 2:27:1-27:27.

[70] Mohri C C M. Confidence intervals for the area under the ROC curve. Adv Neural Inf Process Syst 17 Proc 2004 Conf 2005; 17:305.

[71] Borg I, Groenen P J F. Modern multidimensional scaling: Theory and applications. Springer; 2005.

The invention claimed is:

1. A method for evaluating an aspect of a proposed treatment plan for radiation therapy the method comprising:
obtaining the aspect of a proposed radiation therapy treatment plan defining radiation therapy treatment for at least one treatment site, and a set of patient data for a patient using a processor that communicates with one or more memories storing the proposed treatment plan and the set of patient data, the set of patient data comprising at least one set of image data for the at least one treatment site or data derived from the at least one set of image data;
generating a quality assessment output of a calculated quality estimate for the aspect of the proposed radiation therapy treatment plan using the processor to access the proposed radiation therapy treatment plan and the set of patient data stored in the one or more memories and extract one or more plan features from the aspect of the proposed treatment plan and one or more patient features from the set of patient data to evaluate the aspect of the proposed treatment plan according to a quality assurance model of one or more machine-learned rules for automated quality assessment stored in the one or more memories, the machine-learned rules defining expected relationships between the one or more plan features, and the one or more patient features derived from the set of patient data;

generating the quality assurance model of the one or more machine-learned rules for automated quality assessment by one or more of methods selected from the group of: artificial neural networks, tree-based models, support vector machines, K-means, naïve Bayes, deep learning models, and non-linear, multivariate classification or regression models; and wherein the quality assurance model of the one or more machine-learned rules for automated quality assessment stored in the one or more memories were developed or refined by machine learning trained on features extracted from a plurality of radiation therapy treatment plans.

2. The method of claim 1, wherein generating the output further comprises:

evaluating the aspect of the proposed treatment plan according to the one or more rules defining expected relationships between a treatment plan characterization and one or more of: the one or more plan features, and the one or more patient features defined in the set of patient data.

3. The method of claim 2, further comprising:

determining the treatment plan characterization by automatically characterizing the aspect of the proposed treatment plan according to the one or more plan features;

wherein characterizing the aspect of the proposed treatment plan comprises determining a treatment plan class for the proposed treatment plan according to one of a plurality of predefined treatment plan classes, using an automated classification process.

4. The method of claim 3, wherein the automated classification process involves rules developed or refined by machine learning using plan features and patient features extracted by the processor from historical data derived from historical treatment plans, a mathematical function, or a general rule governing treatment plans irrespective of the proposed treatment plan and irrespective of the set of patient data.

5. The method of claim 3, wherein the automated classification process is based on determining similarity of features of the proposed treatment plan to features of plans associated with a predefined treatment plan class.

6. The method of claim 1, wherein the plurality of aspects of the proposed treatment plan comprises a set of region of interest (ROI) data delineating at least one ROI in the set of image data; and wherein the method further comprises automatically characterizing the at least one ROI according to one or more features to determine at least one ROI characterization;

wherein generating the output for the aspect of the proposed treatment plan includes evaluating the aspect of the proposed treatment plan according to one or more rules defining expected relationships between one or more of: the one or more plan features, one or more patient features, the treatment plan characterization, and the at least one ROI characterization.

7. The method of claim 6, wherein characterizing the at least one ROI comprises determining at least one ROI class respectively for the at least one ROI, according to one of a plurality of predefined ROI classes, using an automated classification algorithm.

8. The method of claim 6, further comprising, for each of the at least one ROI, calculating a quality estimate that a given ROI belongs to a given ROI characterization, based on predefined expected features of the given ROI characterization.

9. The method of claim 6, wherein the at least one ROI characterization is determined based on shape and density value of a given ROI.

10. The method of claim 6, wherein the at least one ROI is characterized according to ROI features including one or more of: anatomical correspondence, tumours, dosage, regions to avoid, regions for dose evaluation, reference structures and structures to facilitate treatment planning.

11. The method of claim 6, wherein obtaining the set of ROI data comprises automatically segmenting the at least one ROI from the image data.

12. The method of claim 1, wherein the one or more patient features comprise at least one of: a patient characteristic, a patient history, a patient diagnosis, and an imaged feature.

13. The method of claim 1, wherein the output comprises one or more of:

a confidence measure for the treatment plan characterization;

a probability of error for the aspect of the proposed treatment plan;

a confidence level for the aspect of the proposed treatment plan;

an automatic quality estimate score;

one or more suggestions for modifying the aspect of the proposed treatment plan in order to improve the quality estimate;

and one or more features of the treatment plan characterization that is relevant to the quality estimate.

14. The method of claim 1, wherein the one or more rules defining expected relationships include at least one rule generated by machine learning based on one or more of:

historical suitability of a given treatment plan characterization for historical patients;

historical treatment outcome of a given treatment plan characterization for historical patients;

historical treatment plans for a specific patient;

historical treatment outcomes for the specific patient;

a mathematical function; and a rule governing treatment plans irrespective of the treatment plan characterization and irrespective of the patient data.

15. The method of claim 1, wherein providing the output comprises displaying, on an output device, an indication of one or more plan features or one or more patient features giving rise to a quality estimate of a particular value or within a particular value range.

16. The method of claim 1 wherein the proposed treatment plan is characterized according to treatment plan features including one or more of: number of beams, beam parameters, an anatomical site, a tumour histology, a prescription dose, a treatment technique, and a treatment intent.

17. The method of claim 1, wherein evaluating the proposed treatment plan according to one or more rules defining expected relationships between the one or more patient features comprises evaluating similarity of the one or more patient features for the patient to one or more patient features for another patient.

18. The method of claim 1 further comprising:

displaying a visualization of the aspect of the proposed treatment plan on a display device and providing an interface for receiving user input on the quality assessment output.

19. The method of claim 1 wherein the machine-learned rules are based on historical data of historical treatment plans, wherein the machine learning is ongoing as additional historical data becomes available such that the machine-learned rules are refined over time.

20. The method of claim 1 wherein the patient is a new patient, wherein the proposed radiation therapy treatment plan is for a new proposed plan, wherein the machine learning is trained on features extracted from the plurality of radiation therapy treatment plans that relate to different patients than the new patient, wherein the quality assessment output of the calculated quality estimate for the aspect of the proposed radiation therapy treatment plan indicates a quality of the new proposed plan for the new patient.

21. The method of claim 1 wherein the plurality of radiation therapy treatment plans are a collection of radiation therapy treatment plans of known quality and safety that meet a quality threshold to provide quality training data for the machine learning for developing or refining the one or more machine-learned rules for automated quality assessment.

22. The method of claim 1 wherein the quality assessment output of the calculated quality estimate for the aspect of the proposed radiation therapy treatment plan comprises a determination of how well certain plan features match with expected plan characteristics.

23. The method of claim 1 further comprising generating an error message if the calculated quality estimate is below a threshold value and providing the error message to the interface.

24. The method of claim 6 wherein the quality assessment output of the calculated quality estimate for the aspect of the proposed radiation therapy treatment plan is based on an integrated consideration of the one or more plan features, ROI features, the one or more patient features, and patient treatment requirements.

25. The method of claim 1 wherein the aspect of the proposed radiation therapy treatment plan involves a treatment dose distribution or beam geometry, wherein the quality assessment output of the calculated quality estimate for the aspect of the proposed radiation therapy treatment plan comprises a quality estimate for the treatment dose distribution or the beam geometry.

26. The method of claim 1 wherein the quality assessment output of the calculated quality estimate for the aspect of the proposed radiation therapy treatment plan comprises one or more suggestions for modifying the aspect of the proposed treatment plan in order to improve the quality estimate, or one or more suggestions of what should remain unchanged in the aspect of the proposed treatment plan in order to improve the quality estimate.

27. The method of claim 1 wherein the one or more machine-learned rules receive as input the one or more plan features for the aspect of the proposed radiation therapy treatment plan and the one or more patient features, and generate as output a quality estimate as an estimate of the overall plan quality based on both the one or more plan features and the one or more patient features.

28. The method of claim 1 wherein the quality assessment output of the calculated quality estimate for the aspect of the proposed radiation therapy treatment plan involves the one or more patient features in conjunction with a beam geometry or dose distribution of the aspect of the proposed radiation therapy treatment plan.

29. The method of claim 1 further comprising providing the quality assessment output of the calculated quality estimate for the aspect of the proposed radiation therapy treatment plan to an interface to one or more of a plan review and approval system, a visualization system, a database accessed by a radiation treatment system, and the one or more memories.

30. The method of claim 1 further comprising providing, to an interface or the one or more memories, the quality assessment output of the calculated quality estimate for the aspect of the proposed radiation therapy treatment plan and guidelines for improving the quality estimate.

31. The method of claim 1 further comprising retrospectively searching a clinical database of treatment plans to obtain the aspect of the proposed radiation therapy treatment plan defining radiation therapy treatment for at least one treatment site.

32. The method of claim 1 further comprising generating the quality assurance model of the one or more machine-learned rules for automated quality assessment by machine learning for automated classification and/or regression, training the quality assurance model, and updating the quality assurance model with additional data.

33. The method of claim 1 further comprising displaying a visualization of the quality assessment output of the calculated quality estimate for the aspect of the proposed radiation therapy treatment plan on a display device.

34. A method for evaluating at least one delineated region of interest (ROI) for radiation therapy, the method comprising:
    obtaining a set of ROI data delineating the at least one ROI for at least one treatment site in a set of image data, and a set of patient data for a patient using a processor that communicates with one or more memories storing a proposed radiation therapy treatment plan and the set of patient data;
    generating a quality assessment output of a calculated quality estimate for the aspect of the proposed radiation therapy treatment plan using the processor to access the proposed radiation therapy treatment plan and the set of patient data stored in the one or more memories and extract one or more plan features from the aspect of the proposed radiation therapy treatment plan and one or more patient features from the set of patient data to compute a quality estimate for the at least one ROI by evaluating the at least one ROI according to a quality assurance model of one or more machine-learned rules for automated quality assessment defining expected relationships between one or more ROI features, and one or more patient features defined in the set of patient data;
    generating the quality assurance model of the one or more machine-learned rules for automated quality assessment by one or more of methods selected from the group of: artificial neural networks, tree-based models, support vector machines, K-means, naïve Bayes, deep learning models, and non-linear, multivariate classification or regression models; and
    wherein the one or more machine-learned rules for automated quality assessment stored in the one or more memories were developed or refined by machine learning trained on features extracted from a plurality of radiation therapy treatment plans.

35. The method of claim 34, wherein the ROI is characterized according to one or more ROI features including one or more of: anatomical correspondence, tumours, dosage, regions to avoid, regions for dose evaluation, and a reference structure.

36. A computer system for evaluating an aspect of a proposed treatment plan for radiation therapy, the system comprising:
- one or more memories storing a proposed radiation therapy treatment plan and the set of patient data; and one or more machined-learned rules;
- a processor that communicates with the one or more memories to:
    - obtain the aspect of the proposed radiation therapy treatment plan defining radiation therapy treatment for at least one treatment site, and a set of patient data for a patient;
    - generate a quality assessment output of a calculated quality estimate for the aspect of the proposed radiation therapy treatment plan by evaluating the aspect of the proposed radiation therapy treatment plan according to a quality assurance model of the one or more machine-learned rules for automated quality assessment defining expected relationships between one or more plan features, and one or more patient features defined in the set of patient data;
    - generate the quality assurance model of the one or more machine-learned rules for automated quality assessment by one or more of methods selected from the group of: artificial neural networks, tree-based models, support vector machines, K-means, naïve Bayes, deep learning models, and non-linear, multivariate classification or regression models; and
- wherein the quality assurance model of the one or more machine-learned rules for automated quality assessment stored in the one or more memories were developed or refined by machine learning trained on features extracted from a plurality of radiation therapy treatment plans.

* * * * *